United States Patent
Berti et al.

(10) Patent No.: US 9,562,894 B2
(45) Date of Patent: Feb. 7, 2017

(54) METHOD OF DETECTING THE PRESENCE OF AN ANTIBODY IN A SAMPLE

(71) Applicant: GlaxoSmithKline Biologicals SA, Rixensart (BE)

(72) Inventors: Francesco Berti, Colle Val d'Elsa (IT); Carl E. Frasch, Martinsburg, WV (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/363,383

(22) PCT Filed: Dec. 12, 2012

(86) PCT No.: PCT/IB2012/057253
§ 371 (c)(1),
(2) Date: Jun. 6, 2014

(87) PCT Pub. No.: WO2013/088378
PCT Pub. Date: Jun. 20, 2013

(65) Prior Publication Data
US 2014/0335544 A1    Nov. 13, 2014

(30) Foreign Application Priority Data
Dec. 12, 2011   (GB) .................................. 1121301.4

(51) Int. Cl.
| | | |
|---|---|---|
| *G01N 33/569* | (2006.01) | |
| *G01N 33/543* | (2006.01) | |
| *C07K 16/12* | (2006.01) | |
| *G01N 33/68* | (2006.01) | |
| *A61K 39/40* | (2006.01) | |
| *A61K 39/00* | (2006.01) | |

(52) U.S. Cl.
CPC ..... *G01N 33/54306* (2013.01); *C07K 16/1275* (2013.01); *G01N 33/6854* (2013.01); *A61K 39/40* (2013.01); *A61K 2039/6037* (2013.01); *A61K 2039/627* (2013.01); *G01N 2400/40* (2013.01)

(58) Field of Classification Search
None
See application file for complete search history.

(56) References Cited

FOREIGN PATENT DOCUMENTS

WO    2012035519 A1    3/2012

OTHER PUBLICATIONS

Guttormsen et al. JID vol. 173, pp. 142-150 ,1996.*
Lancaster et al. Vaccine, vol. 29, No. 17, pp. 3213-3221, Feb. 12, 2011.*
Wessels et al. J. Clin. Invset. , vol. 86, pp. 1428-1433, 1990.*
Gamoh et al., "Establishment of a Potency Test by ELISA for a Rabies Vaccine for Animal Use in Japan, Journal of Veterinary Medical Science," 2003, vol. 65, No. 6, pp. 685-688.
International Search Report for PCT/IB2012/057253 mailed Mar. 14, 2014.
Lancaster et al., "Immunogenicity and physico-chemical characterisation of a candidate conjugate vaccine against group B *Streptococcus* serotypes Ia, Ib and III," Vaccine, 2011, vol. 29, No. 17, pp. 3213-3221.
Shen et al., "Group B *Streptococcus* capsular polysaccharide-cholera toxin B subunit conjugate vaccines prepaed by different methods for intranasal immunization," Infection and Immunity, 2001, vol. 69, No. 1, pp. 297-306.
Sutton et al., "An avidin-biotin based ELISA for quantitation of antibody to bacterial polysaccharides," Journal of Immunological Methods, 1985, vol. 82, No. 2, pp. 215-224.

* cited by examiner

*Primary Examiner* — J. Hines
*Assistant Examiner* — Khatol Shahnan Shah
(74) *Attorney, Agent, or Firm* — Virginia G. Campen

(57) ABSTRACT

Methods for detecting in a sample the presence of an antibody to a conjugate of an antigen associated with a first carrier by a first association are disclosed. The method comprises contacting a conjugate of the antigen associated with a second carrier by a second association with said sample under conditions that allow binding of the antibody to the antigen; and introducing an agent to detect the presence of the antibody bound to said antigen. The first association and the second association are covalent associations and the first association is different from the second association. Also provided are kits, multiwell plates and conjugates that are useful in the method and further uses of the method. Also provided is a method of releasing a batch of a vaccine comprising a conjugate of an antigen associated with a first carrier by a first association and antibodies useful in this method.

18 Claims, 31 Drawing Sheets

HSAadh Lot1
Gel 3-8% Tris-Acetate
1. Marker
2. HSA
3. HSAadh

HSAadh LotMR1204
Gel 3-8% Tris-Acetate
1. HSA
2. Marker
3. HSAadh

Gel 3-8% Tris-Acetate
1. Marker
2. HSA
3. HSAadh
4. Ia-HSAadh postHA
5. Ib-HSAadh postHA
6. III-HSAadh postHA Gel 3-8% Tris-Acetate
1. Marker
2. HSAadh
3. Ib-HSAadh, (i) postS400
4. Ib-HSAadh, (ii) postS400
5. Ib-HSAadh, (iii) postS400
6. Ib-HSAadh, (iv) postS400

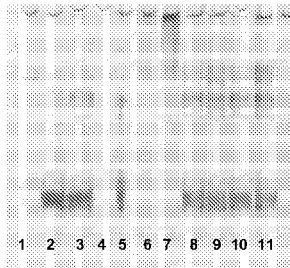
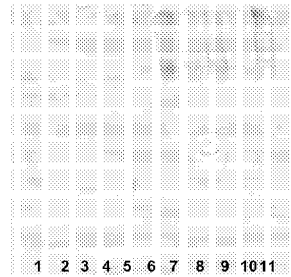
Figure 8a      Figure 8b
Gel 7% Tris-Acetate
1. Marker
2. HSA
3. HSAadh
4. PSIb
5. PSIb + HSAadh
6. Conj Ib-1523/80
7.
8. Conj Ib-HSAadh, *4* crude
9. Conj Ib-HSAadh, *2* crude
10. Conj Ib-HSAadh, *3* crude
11. Conj Ib-HSAadh, *1* crude
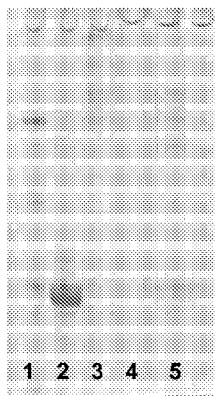
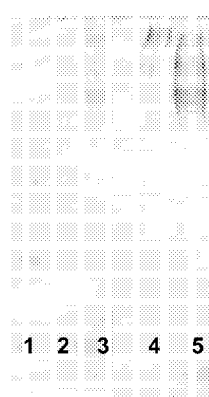
Figure 8c      Figure 8d
Gel 7% Tris-Acetate
1. Marker
2. HSA
3. Conj Ib-1523/80
4. Conj Ib-HSAadh, fraction from SEC
5. Conj Ib-HSAadh, fraction from SEC
Primary Ab: rabbit serum 1:3000 antiIb-CRM.

a GBS Ib-HSAADH Lot MR1204
b GBS Ib-HSAADH Lot MR1204+spike 60 µg/ml PS Ib
c Ib std 50 µg/ml a GBS Ib-HSAADH TN 1504
b GBS Ib-HSAADH TN 1504 +spike 60 µg/ml
c Ib std 50 µg/ml a GBS Ib-HSAADH Lot TN Feb10
b GBS Ib-HSAADH Lot TN Feb10+ spike PS Ib 50 mg/ml
c GBS Ib std 50 mg/ml

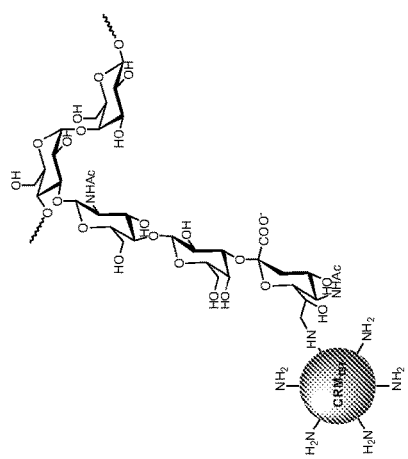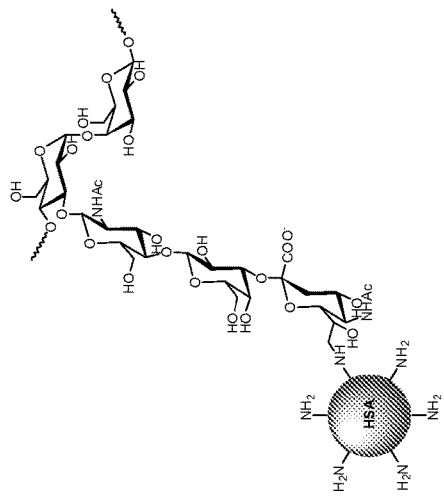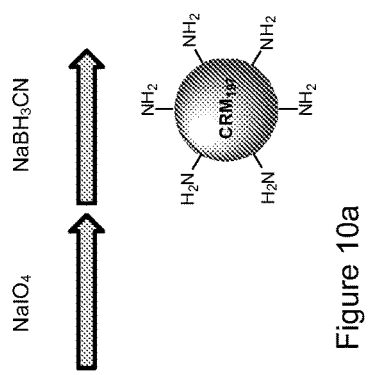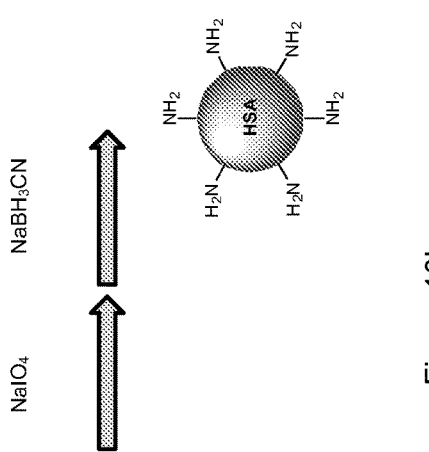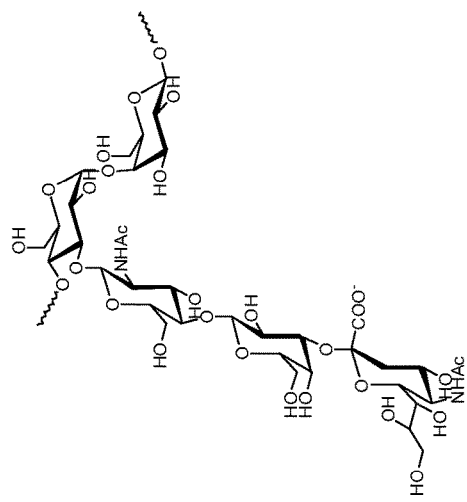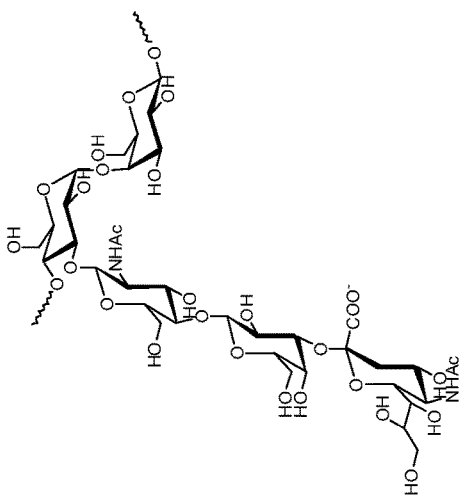
Figure 10a
Figure 10b

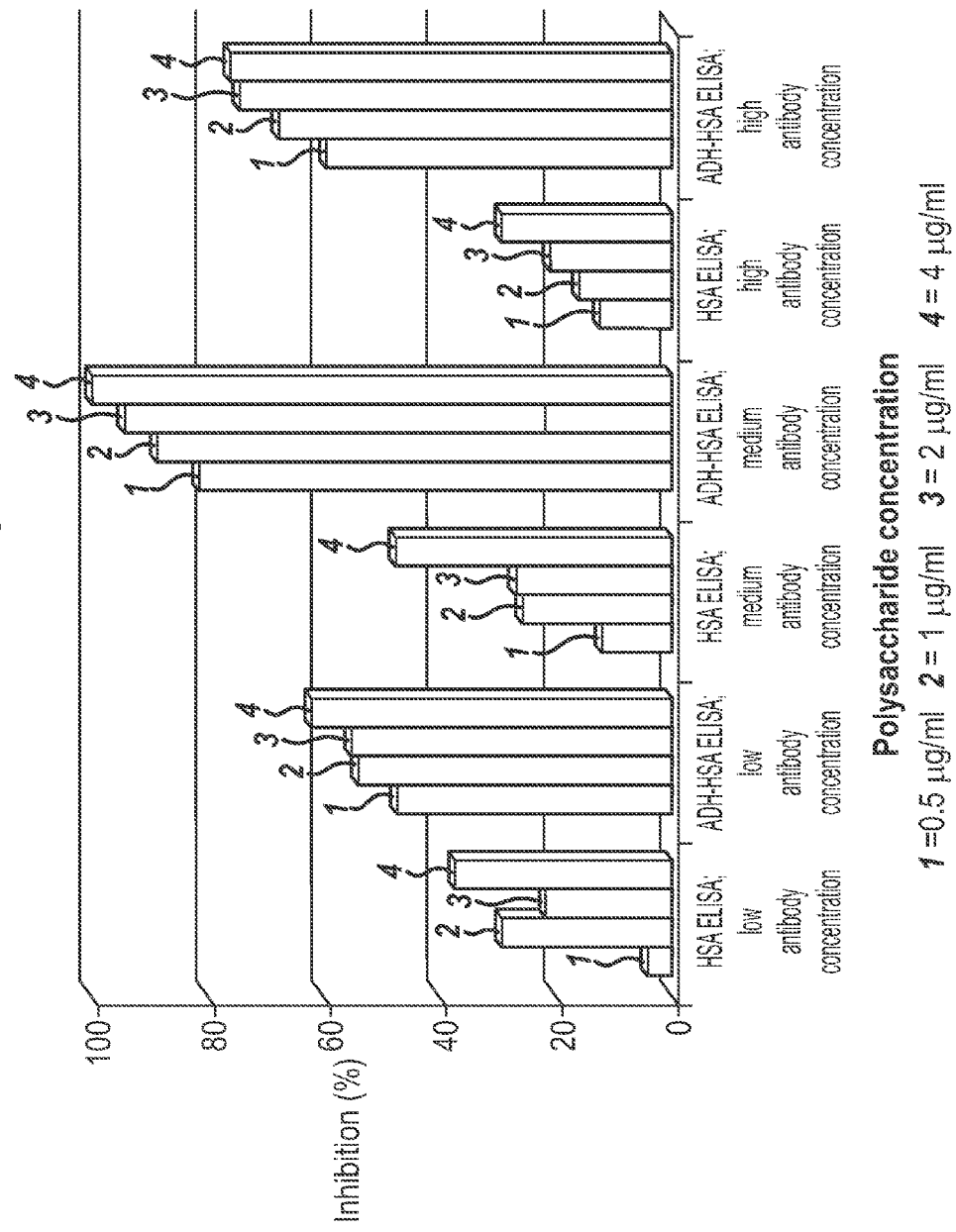

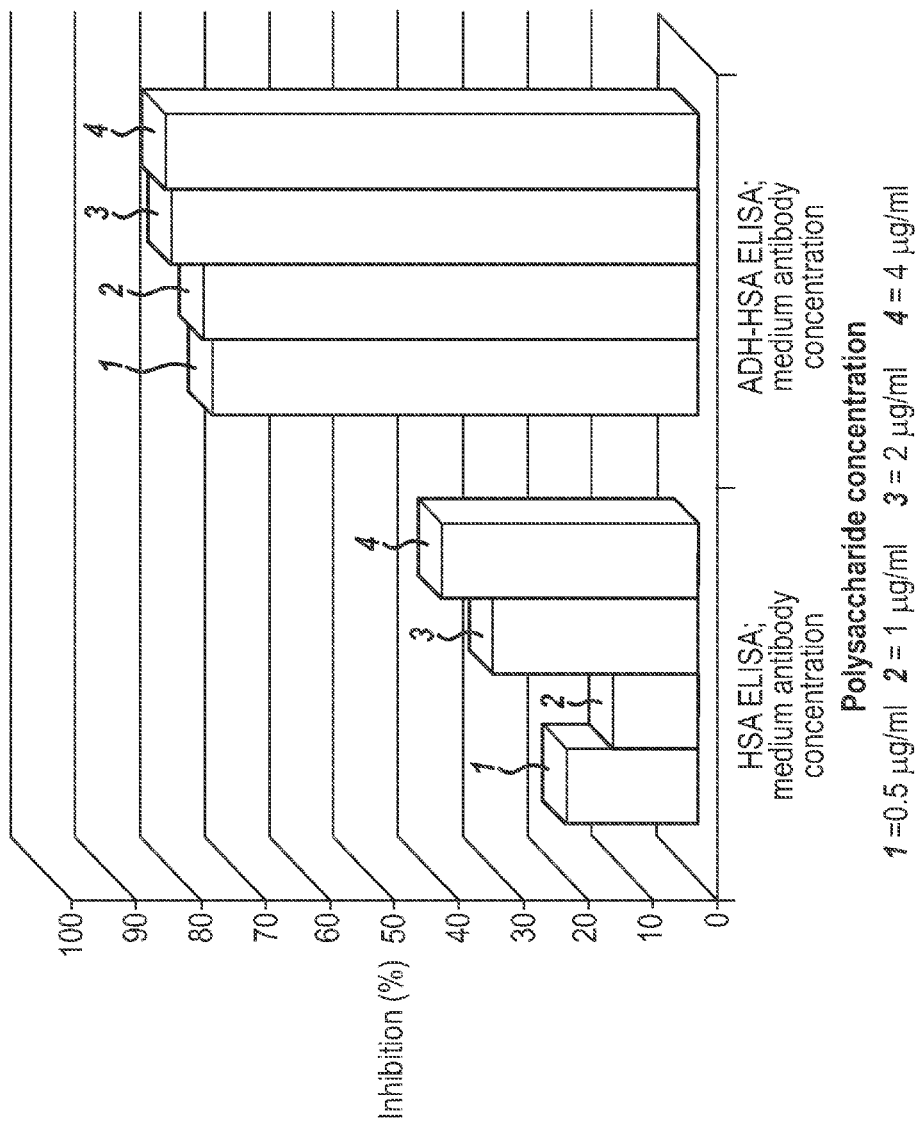

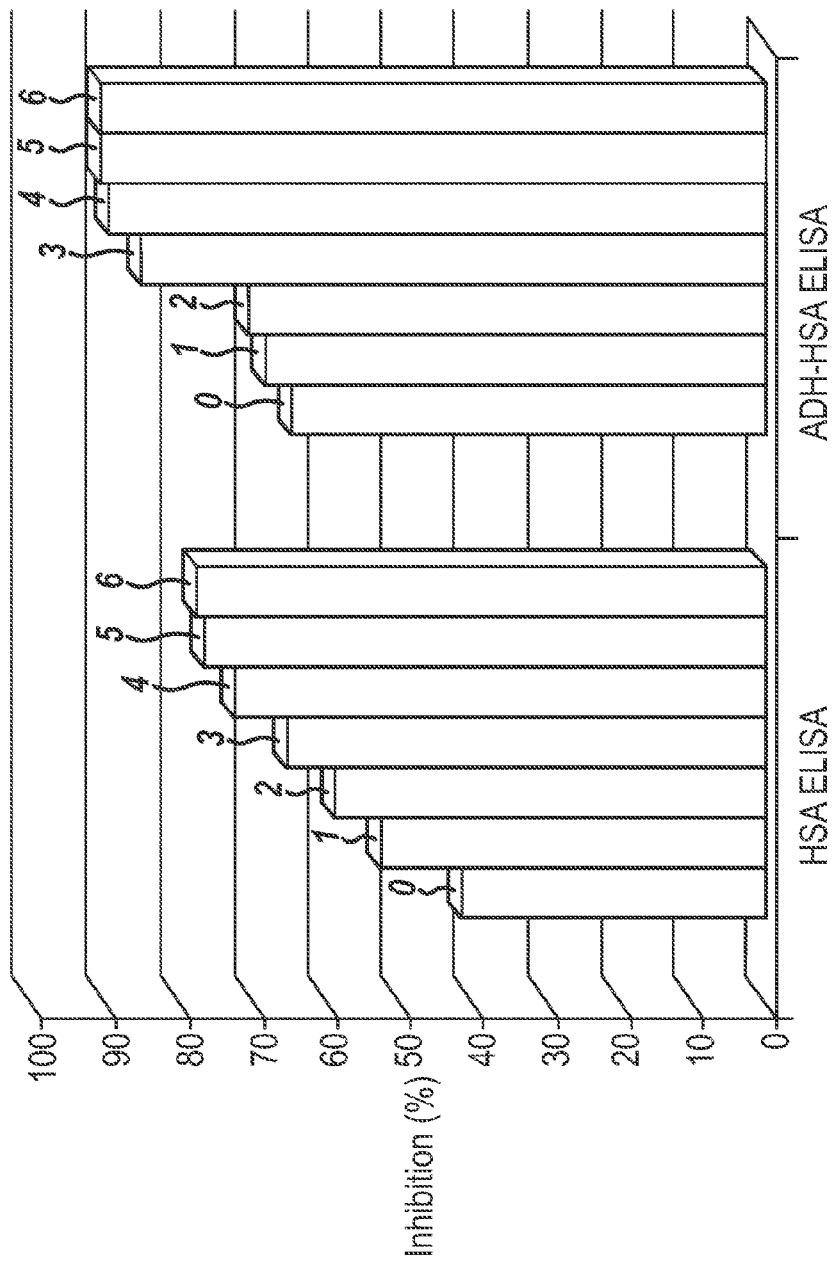

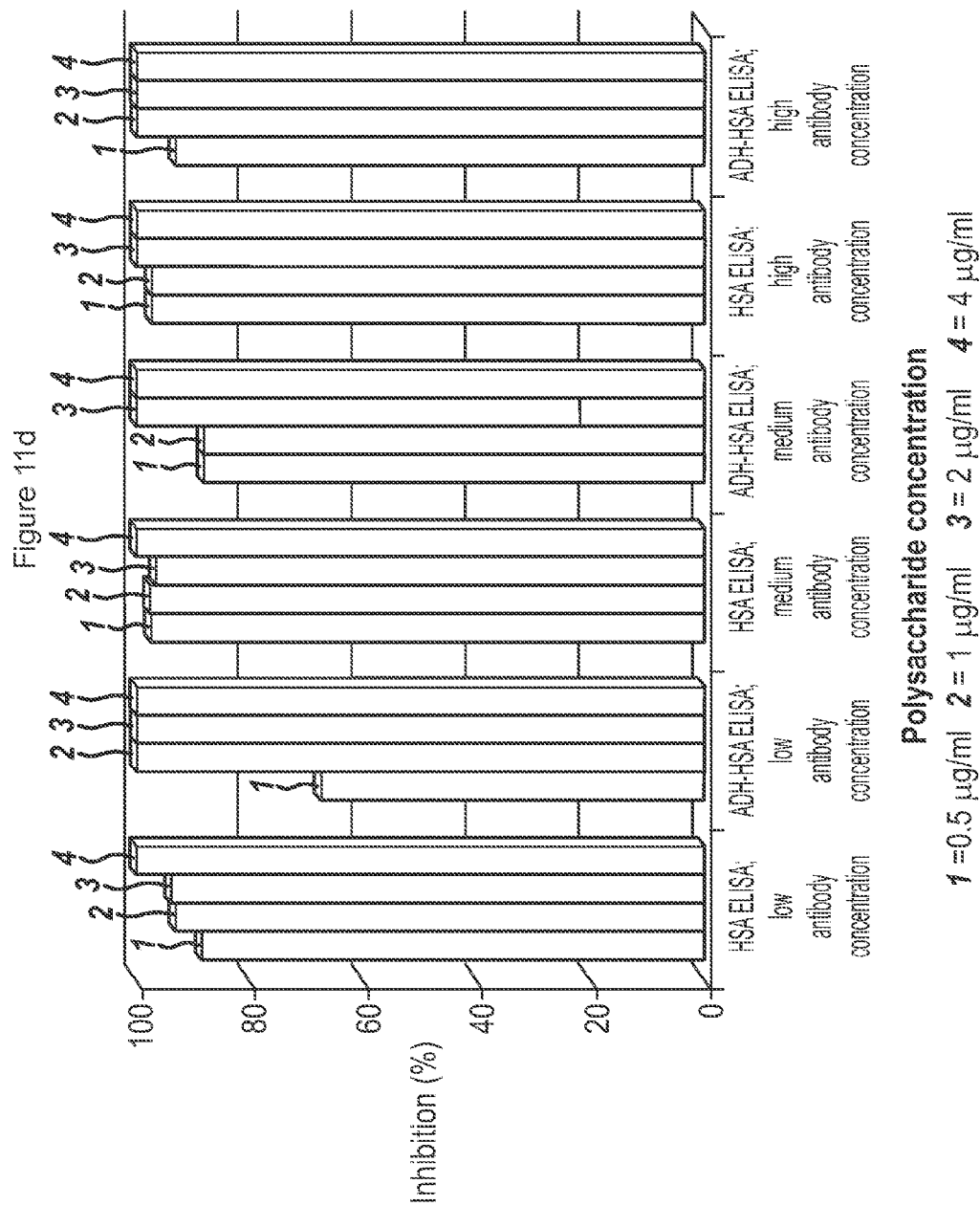

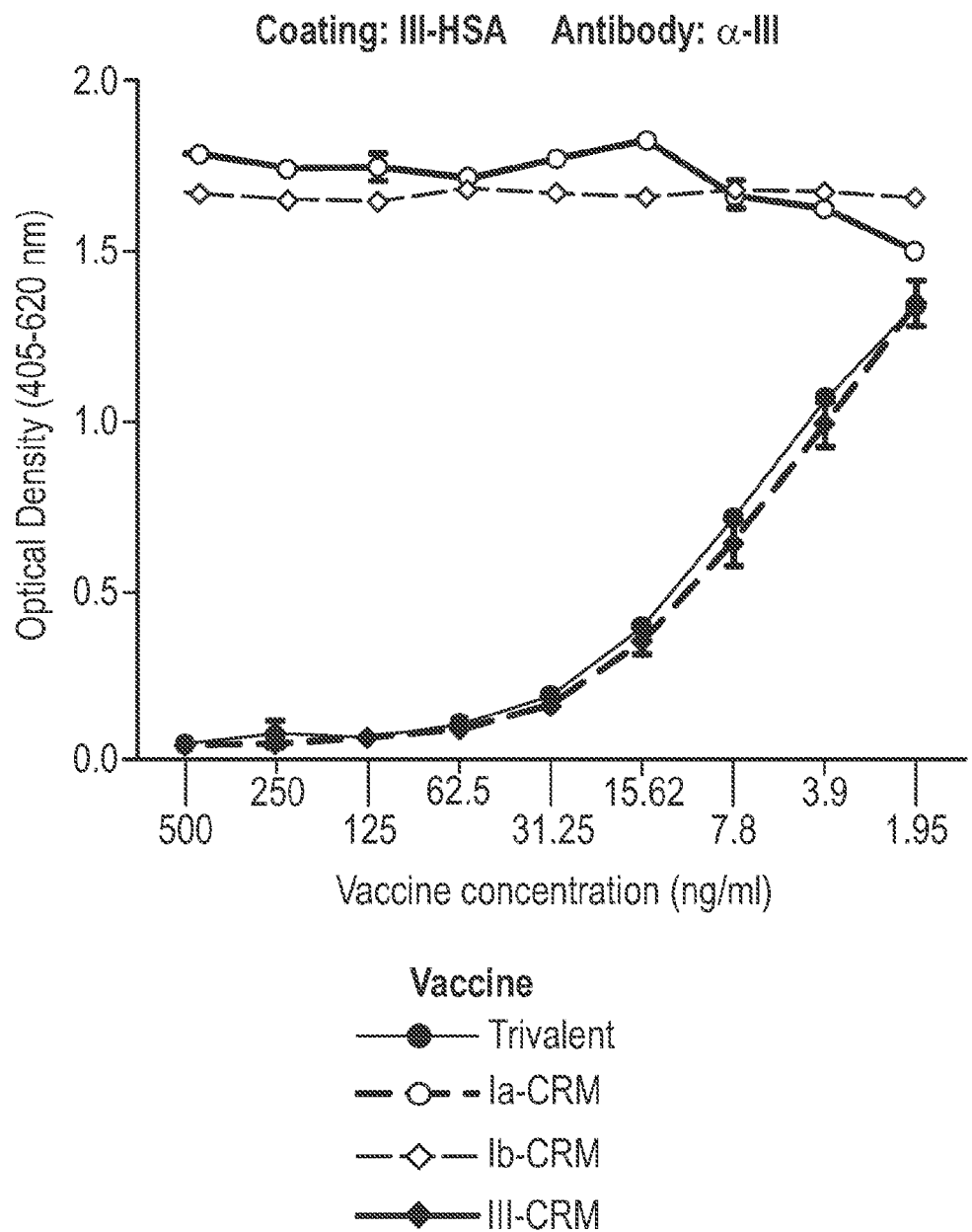
Figure 16(contd)

GBS type III - mAb 27C6C10

○ 50-100% Signals from PS regions with high antibody-binding
◌ 10-50% Signals from PS regions with medium antibody-binding
⋯ <10% Signals from PS regions with no antibody-binding
(% of signal with maximum difference)

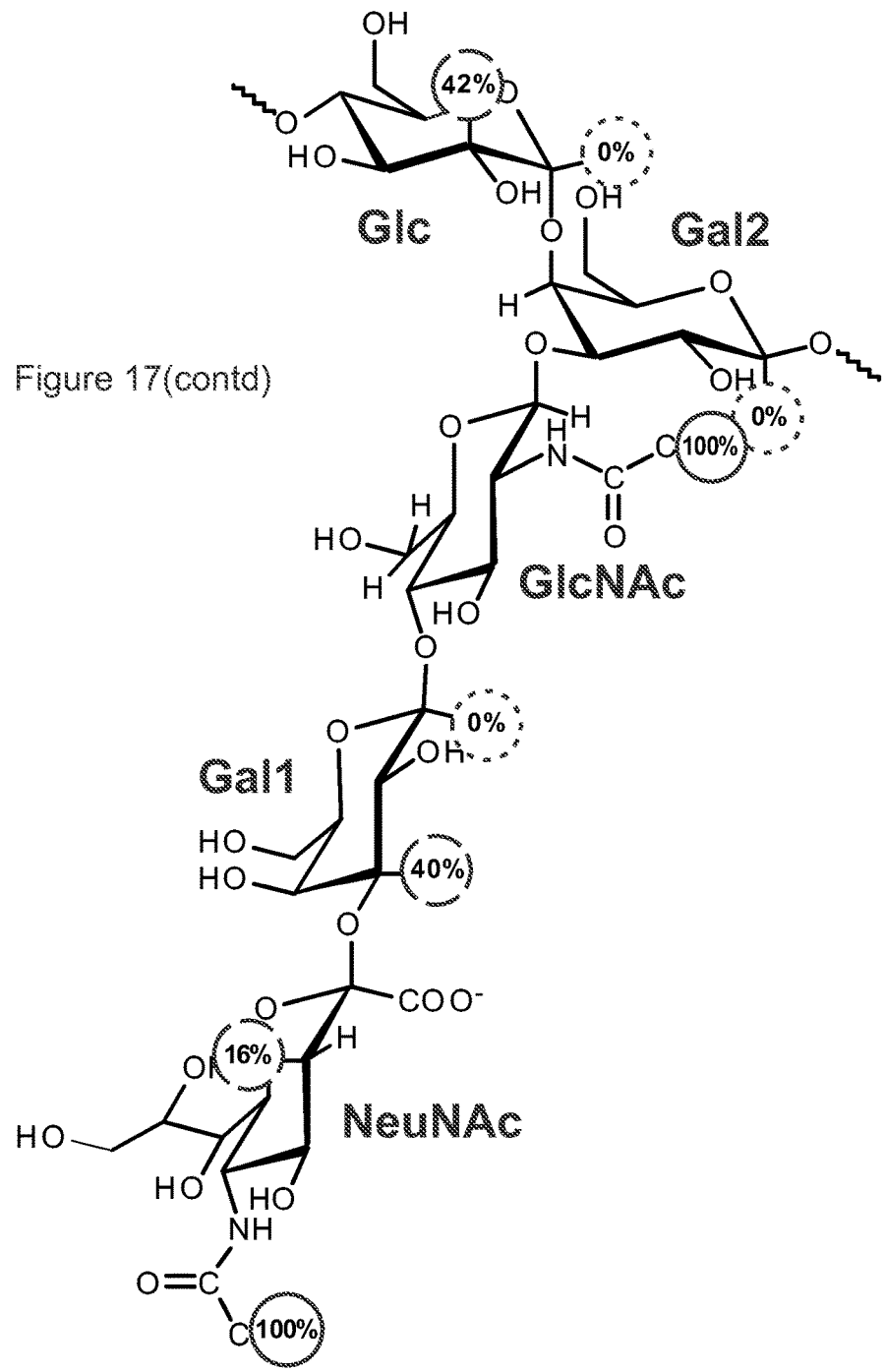
Figure 17(contd)

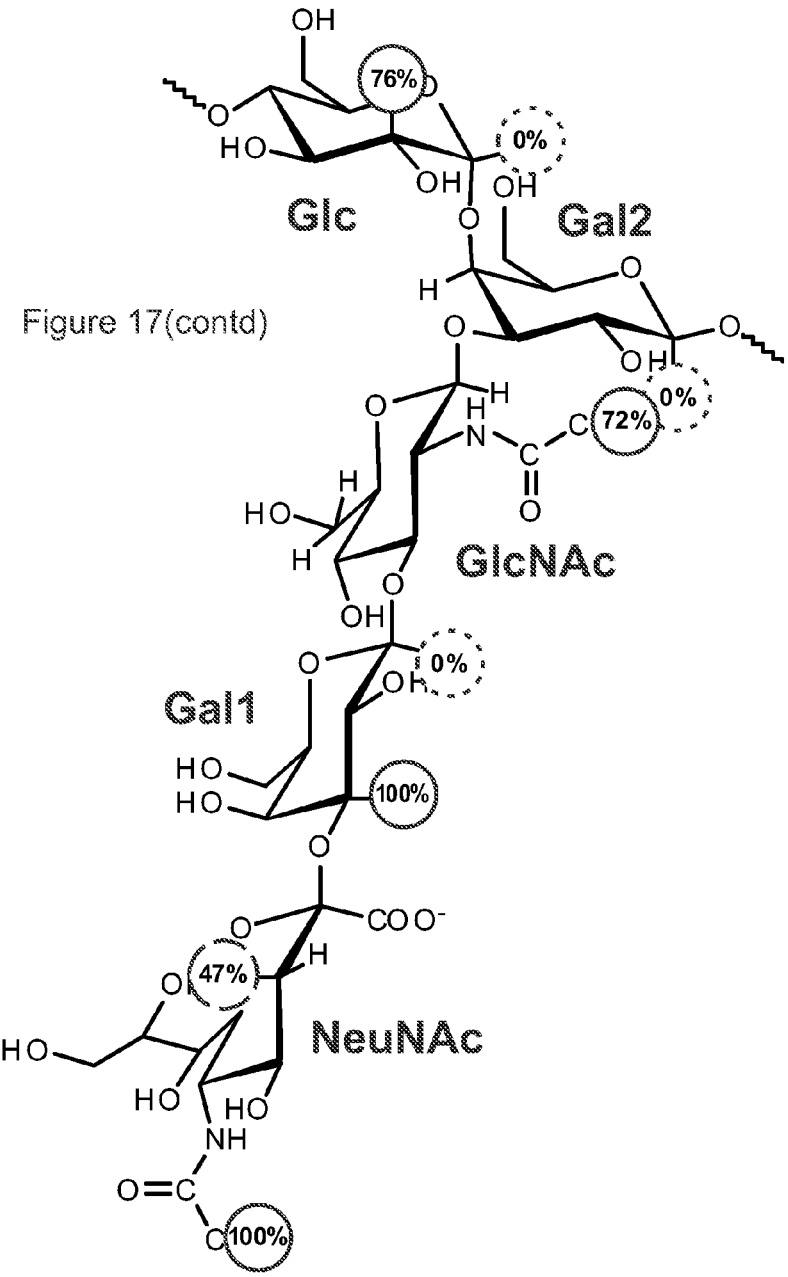
Figure 17(contd)

SEQUENCE LISTING

<160> NUMBER OF SEQ ID NOS: 36

<210> SEQ ID NO 1
<211> LENGTH: 436
<212> TYPE: DNA
<213> ORGANISM: Mus musculus

<400> SEQUENCE: 1

```
catgaagttg cctgttaggc tgttggtgct gatgttctgg attcctgttt ccagcagtga        60
tgctgtgatg acccaaactc cactctccct gcctgtcagt cttggagatc aagcctccat       120
ctcctgcagg tctagtcaga gccttgaaaa cactgatgga agcacctatt tgaactggta       180
cctccagaaa ccaggccagt ctccacagct cctgatctac agggtttcca cccgattttc       240
tggggtccta gacaggttca gtggtagtgg atcagggaca gatttcacac tgaaaatcag       300
cagagtggag gctgaggatt tgggagttta tttctgcctc caacttacac atgtcccgta       360
cacgttcgga gggggaccaa gctggaaat aaaacgggct gatgctgcac caactgtatc       420
catcttccca ccatcc                                                       436
```

<210> SEQ ID NO 2
<211> LENGTH: 146
<212> TYPE: PRT
<213> ORGANISM: Mus musculus

<400> SEQUENCE: 2

```
Met Lys Leu Pro Val Arg Leu Leu Val Leu Met Phe Trp Ile Pro Val
1               5                   10                  15

Ser Ser Ser Asp Ala Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Glu Asn Thr Asp Gly Ser Thr Tyr Leu Asn Trp Tyr Leu Gln Lys Pro
    50                  55                  60

Gly Gln Ser Pro Gln Leu Leu Ile Tyr Arg Val Ser Thr Arg Phe Ser
65                  70                  75                  80

Gly Val Leu Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Leu Gln Leu Thr His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser
145
```

<210> SEQ ID NO 3
<211> LENGTH: 436
<212> TYPE: DNA
<213> ORGANISM: Mus musculus

<400> SEQUENCE: 3

```
atggctgtct tagggctgtt cttctgcctg gtgacattcc caagctgtgt cctatcccag      60
gtgcagctga agcagtcagg acctggccta gtgcagccct cacagagcct gtccatcacc     120
tgcacagtct ctggtttctc attaactagc tatggtgtac actgggttcg ccagtctcca     180
ggaaagggtc tggagtggct gggagtgata tggaatggtg gaagcacaga ctataatgca     240
gctttcatat ccagactaaa catcatcaag gacaattcca agagccaagt tttctttaag     300
atgaacaatc ttcaagctga tgacacagcc acatattact gtgtcagaaa ctgggactac     360
tggggccaag gcaccactct cacagtctcc tcagctacaa caacagcccc atctgtctat     420
cccctggccc ctggaa                                                     436
```

<210> SEQ ID NO 4
<211> LENGTH: 145
<212> TYPE: PRT
<213> ORGANISM: Mus musculus

<400> SEQUENCE: 4

```
Met Ala Val Leu Gly Leu Phe Phe Cys Leu Val Thr Phe Pro Ser Cys
1               5                   10                  15
Val Leu Ser Gln Val Gln Leu Lys Gln Ser Gly Pro Gly Leu Val Gln
            20                  25                  30
Pro Ser Gln Ser Leu Ser Ile Thr Cys Thr Val Ser Gly Phe Ser Leu
        35                  40                  45
Thr Ser Tyr Gly Val His Trp Val Arg Gln Ser Pro Gly Lys Gly Leu
    50                  55                  60
Glu Trp Leu Gly Val Ile Trp Asn Gly Gly Ser Thr Asp Tyr Asn Ala
65                  70                  75                  80
Ala Phe Ile Ser Arg Leu Asn Ile Ile Lys Asp Asn Ser Lys Ser Gln
                85                  90                  95
Val Phe Phe Lys Met Asn Asn Leu Gln Ala Asp Asp Thr Ala Thr Tyr
            100                 105                 110
Tyr Cys Val Arg Asn Trp Asp Tyr Trp Gly Gln Gly Thr Thr Leu Thr
        115                 120                 125
Val Ser Ser Ala Thr Thr Thr Ala Pro Ser Val Tyr Pro Leu Ala Pro
    130                 135                 140
Gly
145
```

<210> SEQ ID NO 5
<211> LENGTH: 449
<212> TYPE: DNA
<213> ORGANISM: Mus musculus

<400> SEQUENCE: 5

```
atgaagttgc ctgttaggct gttggtgctg atgttctgga ttcctgcttc cagcagtgat      60
gttttgatga cccaatctcc actctccctg cctgtcagtc ttggagatca agcctccatc     120
tcttgcagat ctagtcagat cattgtacat agtaatggaa acacctattt agagtggtac     180
ctgcagaaac caggccagtc tccaaagctc ctgatctaca gagtttccaa ccgattttct     240
ggggtcccag acaggttcag tggcagtgga tcagggacag atttcacact caagatcagc     300
```

```
agagtggagg ctgaggatct gggagtttat tactgctttc aaggttcaca tgttccgtac    360
acgttcggag gggggaccaa gctggaaata aaacgggctg atgctgcacc aactgtatcc    420
atcttcccac catccagtaa agcttggga                                      449
```

<210> SEQ ID NO 6
<211> LENGTH: 149
<212> TYPE: PRT
<213> ORGANISM: Mus musculus

<400> SEQUENCE: 6

```
Met Lys Leu Pro Val Arg Leu Leu Val Leu Met Phe Trp Ile Pro Ala
1               5                   10                  15

Ser Ser Ser Asp Val Leu Met Thr Gln Ser Pro Leu Ser Leu Pro Val
            20                  25                  30

Ser Leu Gly Asp Gln Ala Ser Ile Ser Cys Arg Ser Ser Gln Ile Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Arg Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Lys Ala Trp
145
```

<210> SEQ ID NO 7
<211> LENGTH: 464
<212> TYPE: DNA
<213> ORGANISM: Mus musculus

<400> SEQUENCE: 7

```
catgggcagg cttactttt cattcttgct actgattgtc cctgcatatg tcctgtgcca     60
ggttactctg aaagagtctg gcccggggat attgcagccc tcccagaccc tcagtctgac    120
ttgttctttc tctgggtttt cactgagcac ttctaatatg ggtgtaggct ggattcgtca    180
gccttcaggg aagggtctgg agtggctctt acacattttg tggaatgata gtaagtacta    240
taatccagcc ctgaagagcc ggctcacaat ctccaaggat acctacaaca caaggtatt    300 cctcaagatc gccaatgtgg acactgcaga ttctgccaca tactactgtg ttcgattccc    360
ccatgatggt tacaaagtta tggactactg gggtcaagga acctcagtca ccgtctcctc    420
agccaaaacg acacccccat ctgtctatcc cctggcccct ggaa                     464
```

<210> SEQ ID NO 8
<211> LENGTH: 154
<212> TYPE: PRT
<213> ORGANISM: Mus musculus

<400> SEQUENCE: 8

```
Met Gly Arg Leu Thr Phe Ser Phe Leu Leu Leu Ile Val Pro Ala Tyr
1               5                   10                  15
```

-continued

```
Val Leu Cys Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Asn Met Gly Val Gly Trp Ile Arg Gln Pro Ser Gly Lys
 50                  55                  60

Gly Leu Glu Trp Leu Leu His Ile Leu Trp Asn Asp Ser Lys Tyr Tyr
 65                  70                  75                  80

Asn Pro Ala Leu Lys Ser Arg Leu Thr Ile Ser Lys Asp Thr Tyr Asn
                85                  90                  95

Asn Lys Val Phe Leu Lys Ile Ala Asn Val Asp Thr Ala Asp Ser Ala
            100                 105                 110

Thr Tyr Tyr Cys Val Arg Phe Pro His Asp Gly Tyr Lys Val Met Asp
            115                 120                 125

Tyr Trp Gly Gln Gly Thr Ser Val Thr Val Ser Ser Ala Lys Thr Thr
130                 135                 140

Pro Pro Ser Val Tyr Pro Leu Ala Pro Gly
145                 150
```

<210> SEQ ID NO 9
<211> LENGTH: 477
<212> TYPE: DNA
<213> ORGANISM: Mus musculus

<400> SEQUENCE: 9

```
tactagtcga catgggcttc aagatgaagt cacagtccca ggttcttatg ttactgctgc    60
tatgggtatc tggtacctgt ggggacattg tgatgtcaca gtctccatcc tccctaactg   120
tgtcagttgg agagaaggtt actatgagct gcaagtccag tcagagcctt ttatatagta   180
gcaatcaaaa gaactacttg gcctggtacc agcagaaacc agggcagtct cctaaactgc   240
tgatttactg ggcatccact agggattctg ggtccctga tcgcttcaca ggcagtggat   300
ctgggacaga tttcactctc accatcagca gtgtgaaggc tgaagacctg gcagtttatt   360
actgtcagca atattatagc atccgtaca cgttcggagg ggggaccaag ctggaaataa   420
aacgggctga tgctgcacca actgtatcca tcttcccacc atccagtaag cttggga     477
```

<210> SEQ ID NO 10
<211> LENGTH: 158
<212> TYPE: PRT
<213> ORGANISM: Mus musculus

<400> SEQUENCE: 10

```
Leu Val Asp Met Gly Phe Lys Met Lys Ser Gln Ser Gln Val Leu Met
 1               5                  10                  15

Leu Leu Leu Leu Trp Val Ser Gly Thr Cys Gly Asp Ile Val Met Ser
            20                  25                  30

Gln Ser Pro Ser Ser Leu Thr Val Ser Val Gly Glu Lys Val Thr Met
        35                  40                  45

Ser Cys Lys Ser Ser Gln Ser Leu Leu Tyr Ser Ser Asn Gln Lys Asn
 50                  55                  60

Tyr Leu Ala Trp Tyr Gln Gln Lys Pro Gly Gln Ser Pro Lys Leu Leu
 65                  70                  75                  80

Ile Tyr Trp Ala Ser Thr Arg Asp Ser Gly Val Pro Asp Arg Phe Thr
                85                  90                  95

Gly Ser Gly Ser Gly Thr Asp Phe Thr Leu Thr Ile Ser Ser Val Lys
            100                 105                 110
```

```
Ala Glu Asp Leu Ala Val Tyr Tyr Cys Gln Gln Tyr Tyr Ser Tyr Pro
        115                 120                 125

Tyr Thr Phe Gly Gly Gly Thr Lys Leu Glu Ile Lys Arg Ala Asp Ala
    130                 135                 140

Ala Pro Thr Val Ser Ile Phe Pro Pro Ser Ser Lys Leu Gly
145                 150                 155

<210> SEQ ID NO 11
<211> LENGTH: 444
<212> TYPE: DNA
<213> ORGANISM: Mus musculus

<400> SEQUENCE: 11
cttgattttc cttgccctca ttttaaaagg tgtccagtgt gaggtgcagc tggtggagtc      60
tgggggagac ttagtgaagc ctggagggtc cctgaaactc tcctgtgcag cctctggatt    120
cactttcagt agctctggca tgtcttgggt tcgccagact ccagacaaga ggctggagtg    180
ggtcgcaatt gttactagtg gtggtagtta cacctactgt ccagacagtg tgaaggggcg    240
attcaccatc tccagagaca atgccaagca caccctgtac ctgcaaatga gcagtccgaa    300
gtctgaggac acagccatgt tttactgtgc aagacatggg gtctactata ggtttgacta    360
ctggggccaa ggcaccactc tcacagtctc ctcagccaaa acaacacccc catcagtcta    420 tccccctggcc cctggaagct tggg                                          444

<210> SEQ ID NO 12
<211> LENGTH: 147
<212> TYPE: PRT
<213> ORGANISM: Mus musculus

<400> SEQUENCE: 12

Leu Ile Phe Leu Ala Leu Ile Leu Lys Gly Val Gln Cys Glu Val Gln
1               5                   10                  15

Leu Val Glu Ser Gly Gly Asp Leu Val Lys Pro Gly Gly Ser Leu Lys
            20                  25                  30

Leu Ser Cys Ala Ala Ser Gly Phe Thr Phe Ser Ser Ser Gly Met Ser
        35                  40                  45

Trp Val Arg Gln Thr Pro Asp Lys Arg Leu Glu Trp Val Ala Ile Val
    50                  55                  60

Thr Ser Gly Gly Ser Tyr Thr Tyr Cys Pro Asp Ser Val Lys Gly Arg
65                  70                  75                  80

Phe Thr Ile Ser Arg Asp Asn Ala Lys His Thr Leu Tyr Leu Gln Met
                85                  90                  95

Ser Ser Pro Lys Ser Glu Asp Thr Ala Met Phe Tyr Cys Ala Arg His
            100                 105                 110

Gly Val Tyr Tyr Arg Phe Asp Tyr Trp Gly Gln Gly Thr Thr Leu Thr
        115                 120                 125

Val Ser Ser Ala Lys Thr Thr Pro Pro Ser Val Tyr Pro Leu Ala Pro
    130                 135                 140

Gly Ser Leu
145

<210> SEQ ID NO 13
<211> LENGTH: 112
<212> TYPE: PRT
<213> ORGANISM: Mus musculus

<400> SEQUENCE: 13
```

```
Val Met Thr Gln Thr Pro Leu Ser Leu Pro Val Ser Leu Gly Asp Gln
1               5                   10                  15

Ala Ser Ile Ser Cys Arg Ser Ser Gln Ser Leu Glu Asn Thr Asp Gly
            20                  25                  30

Ser Thr Tyr Leu Asn Trp Tyr Leu Gln Lys Pro Gly Gln Ser Pro Gln
        35                  40                  45

Leu Leu Ile Tyr Arg Val Ser Thr Arg Phe Ser Gly Val Leu Asp Arg
50                  55                  60

Phe Ser Gly Ser Gly Ser Gly Thr Asp Phe Thr Leu Lys Ile Ser Arg
65                  70                  75                  80

Val Glu Ala Glu Asp Leu Gly Val Tyr Phe Cys Leu Gln Leu Thr His
                85                  90                  95

Val Pro Tyr Thr Phe Gly Gly Gly Thr Lys Leu Glu Ile Lys Arg Ala
            100                 105                 110

<210> SEQ ID NO 14
<211> LENGTH: 112
<212> TYPE: PRT
<213> ORGANISM: Mus musculus

<400> SEQUENCE: 14

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Asn Gly Gly Ser Thr Asp Tyr Asn Ala Ala Phe Ile
50                  55                  60

Ser Arg Leu Asn Ile Ile Lys Asp Asn Ser Lys Ser Gln Val Phe Phe
65                  70                  75                  80

Lys Met Asn Asn Leu Gln Ala Asp Asp Thr Ala Thr Tyr Tyr Cys Val
                85                  90                  95

Arg Asn Trp Asp Tyr Trp Gly Gln Gly Thr Thr Leu Thr Val Ser Ser
            100                 105                 110

<210> SEQ ID NO 15
<211> LENGTH: 113
<212> TYPE: PRT
<213> ORGANISM: Mus musculus

<400> SEQUENCE: 15

Val Leu Met Thr Gln Ser Pro Leu Ser Leu Pro Val Ser Leu Gly Asp
1               5                   10                  15

Gln Ala Ser Ile Ser Cys Arg Ser Ser Gln Ile Ile Val His Ser Asn
            20                  25                  30

Gly Asn Thr Tyr Leu Glu Trp Tyr Leu Gln Lys Pro Gly Gln Ser Pro
        35                  40                  45

Lys Leu Leu Ile Tyr Arg Val Ser Asn Arg Phe Ser Gly Val Pro Asp
50                  55                  60

Arg Phe Ser Gly Ser Gly Ser Gly Thr Asp Phe Thr Leu Lys Ile Ser
65                  70                  75                  80

Arg Val Glu Ala Glu Asp Leu Gly Val Tyr Tyr Cys Phe Gln Gly Ser
                85                  90                  95

His Val Pro Tyr Thr Phe Gly Gly Gly Thr Lys Leu Glu Ile Lys Arg
            100                 105                 110
```

Ala

<210> SEQ ID NO 16
<211> LENGTH: 121
<212> TYPE: PRT
<213> ORGANISM: Mus musculus

<400> SEQUENCE: 16

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Asn Met Gly Val Gly Trp Ile Arg Gln Pro Ser Gly Lys Gly Leu Glu
        35                  40                  45

Trp Leu Leu His Ile Leu Trp Asn Asp Ser Lys Tyr Tyr Asn Pro Ala
    50                  55                  60

Leu Lys Ser Arg Leu Thr Ile Ser Lys Asp Thr Tyr Asn Asn Lys Val
65                  70                  75                  80

Phe Leu Lys Ile Ala Asn Val Asp Thr Ala Asp Ser Ala Thr Tyr Tyr
                85                  90                  95

Cys Val Arg Phe Pro His Asp Gly Tyr Lys Val Met Asp Tyr Trp Gly
            100                 105                 110

Gln Gly Thr Ser Val Thr Val Ser Ser
        115                 120
```

<210> SEQ ID NO 17
<211> LENGTH: 113
<212> TYPE: PRT
<213> ORGANISM: Mus musculus

<400> SEQUENCE: 17

```
Val Met Ser Gln Ser Pro Ser Ser Leu Thr Val Ser Val Gly Glu Lys
1               5                   10                  15

Val Thr Met Ser Cys Lys Ser Ser Gln Ser Leu Leu Tyr Ser Ser Asn
            20                  25                  30

Gln Lys Asn Tyr Leu Ala Trp Tyr Gln Gln Lys Pro Gly Gln Ser Pro
        35                  40                  45

Lys Leu Leu Ile Tyr Trp Ala Ser Thr Arg Asp Ser Gly Val Pro Asp
    50                  55                  60

Arg Phe Thr Gly Ser Gly Ser Gly Thr Asp Phe Thr Leu Thr Ile Ser
65                  70                  75                  80

Ser Val Lys Ala Glu Asp Leu Ala Val Tyr Tyr Cys Gln Gln Tyr Tyr
                85                  90                  95

Ser Tyr Pro Tyr Thr Phe Gly Gly Gly Thr Lys Leu Glu Ile Lys Arg
            100                 105                 110

Ala
```

<210> SEQ ID NO 18
<211> LENGTH: 117
<212> TYPE: PRT
<213> ORGANISM: Mus musculus

<400> SEQUENCE: 18

```
Val Gln Leu Val Glu Ser Gly Gly Asp Leu Val Lys Pro Gly Gly Ser
1               5                   10                  15

Leu Lys Leu Ser Cys Ala Ala Ser Gly Phe Thr Phe Ser Ser Ser Gly
            20                  25                  30
```

```
Met Ser Trp Val Arg Gln Thr Pro Asp Lys Arg Leu Glu Trp Val Ala
            35                  40                  45
Ile Val Thr Ser Gly Gly Ser Tyr Thr Tyr Cys Pro Asp Ser Val Lys
 50                  55                  60
Gly Arg Phe Thr Ile Ser Arg Asp Asn Ala Lys His Thr Leu Tyr Leu
 65                  70                  75                  80
Gln Met Ser Ser Pro Lys Ser Glu Asp Thr Ala Met Phe Tyr Cys Ala
                 85                  90                  95
Arg His Gly Val Tyr Tyr Arg Phe Asp Tyr Trp Gly Gln Gly Thr Thr
            100                 105                 110
Leu Thr Val Ser Ser
        115

<210> SEQ ID NO 19
<211> LENGTH: 17
<212> TYPE: PRT
<213> ORGANISM: Mus musculus

<400> SEQUENCE: 19

Lys Ser Ser Gln Ser Leu Leu Tyr Ser Ser Asn Gln Lys Asn Tyr Leu
 1               5                  10                  15
Ala

<210> SEQ ID NO 20
<211> LENGTH: 7
<212> TYPE: PRT
<213> ORGANISM: Mus musculus

<400> SEQUENCE: 20

Trp Ala Ser Thr Arg Asp Ser
 1               5

<210> SEQ ID NO 21
<211> LENGTH: 9
<212> TYPE: PRT
<213> ORGANISM: Mus musculus

<400> SEQUENCE: 21

Gln Gln Tyr Tyr Ser Tyr Pro Tyr Thr
 1               5

<210> SEQ ID NO 22
<211> LENGTH: 10
<212> TYPE: PRT
<213> ORGANISM: Mus musculus

<400> SEQUENCE: 22

Gly Phe Ser Leu Thr Ser Tyr Gly Val His
 1               5                  10

<210> SEQ ID NO 23
<211> LENGTH: 9
<212> TYPE: PRT
<213> ORGANISM: Mus musculus

<400> SEQUENCE: 23

Val Ile Trp Asn Gly Gly Ser Thr Asp
 1               5

<210> SEQ ID NO 24
<211> LENGTH: 4
```

```
<212> TYPE: PRT
<213> ORGANISM: Mus musculus

<400> SEQUENCE: 24

Asn Trp Asp Tyr
1

<210> SEQ ID NO 25
<211> LENGTH: 16
<212> TYPE: PRT
<213> ORGANISM: Mus musculus

<400> SEQUENCE: 25

Arg Ser Ser Gln Ile Ile Val His Ser Asn Gly Asn Thr Tyr Leu Glu
1               5                   10                  15

<210> SEQ ID NO 26
<211> LENGTH: 7
<212> TYPE: PRT
<213> ORGANISM: Mus musculus

<400> SEQUENCE: 26

Arg Val Ser Asn Arg Phe Ser
1               5

<210> SEQ ID NO 27
<211> LENGTH: 9
<212> TYPE: PRT
<213> ORGANISM: Mus musculus

<400> SEQUENCE: 27

Phe Gln Gly Ser His Val Pro Tyr Thr
1               5

<210> SEQ ID NO 28
<211> LENGTH: 12
<212> TYPE: PRT
<213> ORGANISM: Mus musculus

<400> SEQUENCE: 28

Gly Phe Ser Leu Ser Thr Ser Asn Met Gly Val Gly
1               5                   10

<210> SEQ ID NO 29
<211> LENGTH: 9
<212> TYPE: PRT
<213> ORGANISM: Mus musculus

<400> SEQUENCE: 29

His Ile Leu Trp Asn Asp Ser Lys Tyr
1               5

<210> SEQ ID NO 30
<211> LENGTH: 11
<212> TYPE: PRT
<213> ORGANISM: Mus musculus

<400> SEQUENCE: 30

Phe Pro His Asp Gly Tyr Lys Val Met Asp Tyr
1               5                   10

<210> SEQ ID NO 31
<211> LENGTH: 16
<212> TYPE: PRT
<213> ORGANISM: Mus musculus
```

-continued

```
<400> SEQUENCE: 31

Arg Ser Ser Gln Ser Leu Glu Asn Thr Asp Gly Ser Thr Tyr Leu Asn
1               5                   10                  15

<210> SEQ ID NO 32
<211> LENGTH: 7
<212> TYPE: PRT
<213> ORGANISM: Mus musculus

<400> SEQUENCE: 32

Arg Val Ser Thr Arg Phe Ser
1               5

<210> SEQ ID NO 33
<211> LENGTH: 9
<212> TYPE: PRT
<213> ORGANISM: Mus musculus

<400> SEQUENCE: 33

Leu Gln Leu Thr His Val Pro Tyr Thr
1               5

<210> SEQ ID NO 34
<211> LENGTH: 10
<212> TYPE: PRT
<213> ORGANISM: Mus musculus

<400> SEQUENCE: 34

Gly Phe Thr Phe Ser Ser Ser Gly Met Ser
1               5                   10

<210> SEQ ID NO 35
<211> LENGTH: 10
<212> TYPE: PRT
<213> ORGANISM: Mus musculus

<400> SEQUENCE: 35

Ile Val Thr Ser Gly Gly Ser Tyr Thr Tyr
1               5                   10

<210> SEQ ID NO 36
<211> LENGTH: 9
<212> TYPE: PRT
<213> ORGANISM: Mus musculus

<400> SEQUENCE: 36

His Gly Val Tyr Tyr Arg Phe Asp Tyr
1               5
```

METHOD OF DETECTING THE PRESENCE OF AN ANTIBODY IN A SAMPLE

CROSS REFERENCE TO RELATED APPLICATIONS

This application is the U.S. National Phase of International Application No. PCT/IB2012/057253, filed Dec. 12, 2012 and published in English, which claims the benefit of GB 1121301.4, filed Dec. 12, 2011. The applications are incorporated herein by reference in their entirety.

SEQUENCE LISTING

This application includes a sequence listing that was filed with the PCT application as a part of the specification. The sequence listing is hereby incorporated by reference.

TECHNICAL FIELD

This invention relates to methods of detecting the presence of an antibody in a sample. The methods are particularly useful where the antibody binds to a conjugate of an antigen associated with a carrier protein.

BACKGROUND ART

Many vaccines take the form of conjugates of an antigen associated with a carrier. For example, saccharides from bacteria have been used for many years in vaccines. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib') [e.g. see chapter 14 of ref. [1]].

In assessing the immune response in a subject to a candidate conjugate vaccine, an assay may be used that detects the presence in a sample from the subject of an antibody raised in response to the conjugate. Such an assay usually comprises an immobilized substance that binds specifically to the antibody, for example, the antigen itself. Detection of bound antibody may then be achieved by use of, for example, chemical, biological or radioactive labelling. For example, detection of bound antibody may be achieved by use of a second antibody that recognizes antibodies from the subject, for example, where the assay is in an enzyme-linked immunosorbent assay (ELISA) format. Where the substance that binds specifically to the antibody is the antigen, a conjugate of the antigen associated with a protein may be used. The protein facilitates immobilization of the conjugate, for example to a multiwell plate. This facilitates detection of the antibody in the assay.

Use in the vaccine of a conjugate of the antigen associated with a protein can expose an artificial epitope that is a product of the conjugation. For example, such an artificial epitope may be present at the interface between the antigen and the protein. The candidate conjugate vaccine may therefore give rise to antibodies to this artificial epitope in addition to antibodies to the native antigen. Use in the assay of the conjugate of the antigen associated with a protein can also expose this artificial epitope, and as a result the assay will detect antibodies to this artificial epitope in addition to antibodies to the native antigen. This may give an inaccurate representation of the quantity of native antigen-specific antibodies in the sample being tested. Moreover, in some instances the immobilized conjugate can also cross-react with antibodies to other antigens [2].

In order to avoid detection of the artificial epitope, it is possible to simply use a physical mixture of the antigen and a protein [2]. However, where the antigen is hydrophilic, such as, for example, a saccharide, it can be difficult to immobilize the free antigen, for example to a plate. As a result, assays involving free antigens, either in physical mixture with a protein or alone, tend to have an inadequate level of sensitivity [3].

Development of a selective and sensitive method for detecting the presence of antibodies in a sample has been particularly problematic in the case of group B *streptococcus* (GBS; *Streptococcus agalactiae*). For example, in attempting to detect the presence of antibodies to a saccharide conjugate vaccine, some researchers have investigated an ELISA technique where the GBS saccharide is covalently linked to human serum albumin (HSA). The HSA component is intended to allow the conjugate to effectively bind to the ELISA plate and confer sufficient sensitivity on the assay [4].

However, other researchers have found that use of a conjugate in the assay exposes an artificial epitope (also present within the conjugate vaccine component) which is a product of the conjugation. The ELISA is therefore thought to detect antibodies to this epitope that are not antibodies to the native saccharide. The conjugate used in the assay can also cross-react with antibodies to pneumococcal saccharides [2]. Such a method is therefore insufficiently specific for antibodies to the GBS saccharide. In attempting to solve this problem, researchers have used a mixture of HSA and saccharide. However, this adversely affects the immobilization of the saccharide to the multiwell plate and the resulting assay is therefore insufficiently sensitive [3].

GBS infection constitutes a serious health threat to humans and animals. Of particular concern is the occurrence of GBS infections at the time of childbirth. Expectant mothers who are carriers of this bacterium are exposed to a risk of postpartum infection, and they may also transfer the infection to their child as the child passes through the birth canal. It is therefore useful to be able to determine whether maternal antibody levels are sufficient to protect against neonatal infection. Methods are therefore needed not only in the testing of a candidate conjugate vaccine but also in the surveillance of the effects of a vaccine in a patient, and in testing subjects for existing antibody levels to identify those subjects that may require vaccination. GBS infection is also a health threat to animals. For example, it is the cause of mastitis in dairy herds. Methods are therefore needed for testing and surveillance in veterinary contexts.

With the development of conjugate vaccines, and in particular conjugate vaccines based on GBS capsular saccharides, there is also a need for methods of assessing whether each batch of vaccine manufactured by a given process meets regulatory requirements, e.g. in terms of potency (e.g. immunogenicity). If the vaccine batch meets these requirements, then the vaccine should provide the expected immune response; ideally, there would be no need for further tests such as immunizing a test animal with a sample from the batch. Moreover, the requirements should be a more reliable assessment of potency than a physical characterization of the vaccine alone. The regulatory requirements for release of the vaccine are typically set by agencies such as the U.S. Food and Drug Administration (the FDA) in the United States and the European Medicines Agency (the EMEA) in Europe. It is therefore a further object of the invention to provide methods for assessing the potency of conjugate vaccines that meet these standards.

Accordingly, there remains a need for further and better methods for detecting the presence of antibodies in a sample, specifically of antibodies to a conjugate of an antigen associated with a carrier.

DISCLOSURE OF THE INVENTION

The invention is based on methods that can be used in place of the methods of the prior art for detecting the presence in a sample of an antibody that binds to a conjugate of an antigen and a carrier, in particular an antibody that binds to the antigen within the conjugate. These methods may be more specific and selective for the antibody in question than the prior art methods. For example, the methods of the present invention may have improved specificity as they avoid the problem of detection of antibodies to any artificial epitopes in a candidate conjugate vaccine. The methods of the invention may also allow greater sensitivity as a second carrier may be used that allows the antigen to be effectively immobilized to a surface. In developing these methods, the inventors have made use of an alternative conjugation method that will not expose any artificial epitopes that may be present within the conjugate of the antigen and the first carrier. Accordingly, the methods can be used to detect an antibody to a conjugate of an antigen of interest that is associated with a given carrier.

The invention therefore provides alternative or improved methods for detecting the presence in a sample of an antibody that binds to a conjugate. The invention also provides kits, multiwell plates and conjugates that are useful in the methods of the invention and further uses of the methods, for example, for establishing the efficacy of a vaccine so that it can be provided for use by physicians, for monitoring an immune response to the vaccine in a subject, or testing subjects for existing antibody levels to identify those that may require vaccination.

Accordingly, in a first aspect, the invention provides a method for detecting in a sample the presence of an antibody to a conjugate of an antigen associated with a first carrier by a first association, said method comprising the steps: (i) contacting a conjugate of the antigen associated with a second carrier by a second association with said sample under conditions that allow binding of the antibody to the antigen; and (ii) introducing an agent to detect the presence of the antibody bound to said antigen; wherein the first association is different from the second association. Typically, the first association and the second association are covalent associations.

The method of the first aspect of the invention can be applied to establishing the efficacy of a candidate conjugate vaccine so that it can be provided for use by physicians. For example, the method can be used to test samples obtained from a clinical trial of the vaccine.

Accordingly, in a second aspect, the invention provides a method of providing for use by physicians a vaccine comprising a conjugate of an antigen associated with a first carrier by a first association, comprising the steps of: (a) administering the vaccine to a plurality of subjects; (b) collecting samples from the subjects; (c) measuring the concentration of an antibody to the conjugate in each sample using a method according to the first aspect of the invention; (d) comparing the concentrations with a standard criterion for seroprotection for the antigen; and, if the comparison in step (d) indicates concentrations equal or superior to the criterion for seroprotection in a predetermined proportion of the subjects, (e) providing the vaccine for use by physicians. Typically, the first association and the second association are covalent associations.

The method of the first aspect of the invention can also be applied to assessing whether a batch of a vaccine meets regulatory requirements so that it can be released for use in patients. Instead of using the method to detect the presence or absence of an antibody in a clinical sample as described above, the sample is of a known antibody and the method is used to detect inhibition of the binding of this antibody by the vaccine batch. This inhibition is compared to the inhibition obtained using a reference vaccine of known potency, thereby allowing the potency of the vaccine batch to be assessed.

Accordingly, in a third aspect, the invention provides a method of releasing a batch of a vaccine comprising a conjugate of an antigen associated with a first carrier by a first association, comprising the steps of: (a) contacting, with an antibody to the conjugate in the presence of a portion of the vaccine batch, a conjugate of the antigen associated with a second carrier by a second association under conditions that allow binding of the antibody to the antigen; (b) introducing an agent to detect the presence of the antibody bound to the antigen associated with a second carrier by a second association; (c) determining the quantity of the bound antibody; (d) carrying out steps (a) to (c) with the portion of the vaccine batch substituted by a reference vaccine; (e) comparing the results of each step (c); and, if the comparison in step (e) indicates that the vaccine batch meets pre-determined requirements for release, (f) releasing the vaccine. Typically, the first association is different from the second association. However, in this third aspect of the invention, the problem of artificial epitopes discussed above can be avoided by the selection of an antibody that does not bind to any artificial epitopes and therefore it is less significant for the first association to be different from the second association. It is also typical for the first association and the second association to be covalent associations.

The invention also provides conjugates for use in the methods as described herein. Also provided in the present invention are kits for the methods of the first and second aspects of the invention. In particular, a kit is provided for detecting an antibody to a conjugate of an antigen associated with a first carrier by a first association, said kit comprising a conjugate of the antigen associated with a second carrier by a second association; wherein the first association is different from the second association. Typically, the first association and the second association are covalent associations. Also provided are kits for the method of the third aspect of the invention. In particular, the kit comprises the antibody and the conjugate of the antigen associated with a second carrier by a second association; wherein the first association is different from the second association. The kit may also comprise the agent to detect the presence of the antibody. Finally, a multiwell plate for use in the methods of the present invention is also provided.

The invention also provides antibodies that are useful for the third aspect of the invention.

The Sample

Suitably the sample is selected from the group comprising whole blood, serum and plasma, particularly serum. However, the sample may be a sample from any source. Thus, the sample may be produced in the laboratory or may be derived from a subject. The subject is typically an animal, such as a mammal or bird. Suitably the subject is a mammal such as a human. For example, the subject may be a pregnant mammal, typically a pregnant human. The sample may, for example, be a fluid (concentrated as may be necessary by known methods) such as milk, urine, or amniotic fluid. Alternatively, the sample may be a sample from gastric swabs, urogenital swabs or placental swabs.

The Antigen

Suitably the antigen is a saccharide, typically a saccharide that is a bacterial antigen, for example, a bacterial capsular saccharide. The capsular saccharide may, in particular, be a group B *streptococcus* capsular saccharide. The capsular saccharide is covalently associated with the peptidoglycan backbone of GBS, and is distinct from the group B antigen, which is another saccharide that is attached to the peptidoglycan backbone. As used herein, a saccharide includes a polysaccharide or an oligosaccharide. Oligosaccharides are conveniently formed by fragmentation of purified polysaccharide (e.g. by hydrolysis), which will usually be followed by purification of the fragments of the desired size. Oligosaccharides will typically be sized prior to conjugation. Where the invention includes a depolymerized saccharide, it is preferred that depolymerization precedes conjugation.

The invention is not limited to saccharides purified from natural sources, however, and the saccharides may be obtained by other methods, such as total or partial synthesis.

As noted above, particularly suitable to the present invention are saccharides produced by GBS, especially GBS capsular saccharide. The GBS capsular saccharides are chemically related, but are antigenically very different. All GBS capsular saccharides share the following trisaccharide core:

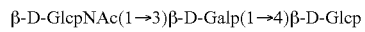

β-D-GlcpNAc(1→3)β-D-Galp(1→4)β-D-Glcp

The various GBS serotypes differ by the way in which this core is modified. The difference between serotypes Ia and III, for instance, arises from the use of either the GlcNAc (Ia) or the Gal (III) in this core for linking consecutive trisaccharide cores. Serotypes Ia and Ib both have a [α-D-NeupNAc(2→3)β-D-Galp-(1→] disaccharide associated with the GlcNAc in the core, but the association is either 1→4 (Ia) or 1→3 (Ib).

GBS-related disease arises primarily from serotypes Ia, Ib, II, III, IV, V, VI, VII, VIII and IX, with over 85% being caused by five serotypes: Ia, Ib, II, III & V. The invention preferably uses a saccharide from one or more of these five serotypes, particularly from one or more of serotypes: Ia, Ib & III. The capsular saccharides of each of these serotypes include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core. The saccharides include galactose residues within the trisaccharide core, but serotypes Ia, Ib, II & III also contain additional galactose residues in each repeating unit.

Saccharides can be purified by known techniques, as described in the references herein such as refs. [4] and [5]. A typical process for purifying GBS capsular saccharides involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful. As an alternative, the purification process described in reference [6] can be used. This involves base extraction, ethanol/CaCl₂ treatment, CTAB precipitation, and re-solubilisation. A further alternative process is described in reference [7].

Other saccharides may be used in the invention. In particular, other bacterial capsular saccharides may be used in the invention. These bacterial capsular saccharides may for example be from *N. meningitidis*, particularly serogroups A, C, W135 and Y; *S. pneumoniae*, particularly from serotypes: 1, 2, 3, 4, 5, 6A, 6B, 7F, 8, 9N, 9V, 10A, 11A, 12F, 14, 15B, 17F, 18C, 19A, 19F, 20, 22F, 23F and 33F; *S. agalactiae*, particularly serotypes Ia, Ib, and III; *Staphylococcus aureus*, particularly from *S. aureus* type 5 and type 8; *H. influenzae* Type b; *Salmonella enterica* Typhi Vi; saccharide antigens from *Staphyloccocus epidermidis* [e.g. type I, II and/or III capsular saccharide obtainable from strains ATCC-31432, SE-360 and SE-10 as described in refs. 8, 9 and 10; and *Clostridium difficile*. The invention may also use non-capsular bacterial saccharides. An exemplary non-capsular bacterial saccharide is the *Streptococcus pyogenes* GAS carbohydrate (also known as the GAS cell wall polysaccharide, or GASP). The invention may also use non-bacterial saccharides. For example, the invention may use glucans, e.g. from fungal cell walls. Representative glucans include laminarin and curdlan.

Additional antigens that may be used in the methods of the present invention include bacterial, viral or parasitic antigens.

In some embodiments, the antigen associated with the first carrier is not identical, e.g. in structure and/or purity, to the antigen associated with the second carrier. For example, when the antigen is a saccharide, the antigen associated with the first carrier may have a different average size and/or range of sizes compared with the antigen associated with the second carrier. Each antigen may be prepared by a different method and/or provided at a different level of purity. However, each antigen contains the epitope or epitopes to which the antibody binds, such that binding to the antigen associated with the second carrier is indicative of an ability to bind to the antigen associated with the first carrier.

The Carriers

The first carrier and/or the second carrier may be a carrier molecule such as a protein or a peptide. Typically both the first and the second carrier are proteins. Typically, the first carrier is different from the second carrier, e.g. the first carrier is one protein (typically diphtheria toxoid, tetanus toxoid, CRM₁₉₇ or protein D) and the second carrier is a different protein (typically human serum albumin). In particular, the second carrier is preferably selected so that it does not comprise any antibody-binding epitopes in common with the first carrier, such that antibodies to the conjugate that bind to the carrier within the conjugate are not detected in the method.

Useful proteins include bacterial toxins or toxoids, such as diphtheria toxoid or tetanus toxoid. Fragments of toxins or toxoids can also be used e.g. fragment C of tetanus toxoid [11]. The CRM₁₉₇ mutant of diphtheria toxin [12-14] is a particularly useful with the invention. Other suitable proteins include the *N. meningitidis* outer membrane protein [15], synthetic peptides [16,17], heat shock proteins [18,19], pertussis proteins [20,21], cytokines [22], lymphokines [22], hormones [22], growth factors [22], human serum albumin (preferably recombinant), artificial proteins comprising multiple human CD4⁺ T cell epitopes from various pathogen-derived antigens [23] such as N19 [24], protein D from *H. influenzae* [25,26], pneumococcal surface protein PspA [27], pneumolysin [28], iron-uptake proteins [29], toxin A or B from *C. difficile* [30], recombinant *Pseudomonas aeruginosa* exoprotein A (rEPA) [31], a GBS protein (particularly GBS67) [32], etc. Also useful as carriers are bacterial pili or fragments thereof, particularly those derived from GBS.

Other suitable proteins include the *N. meningitidis* outer membrane protein complex [33], synthetic peptides [34,35], heat shock proteins [36,37], pertussis proteins [38,39], cytokines [40], lymphokines [40], hormones [40], growth factors [40], artificial proteins comprising multiple human CD4+ T cell epitopes from various pathogen-derived antigens [41] such as N19 [42], protein D from *H. influenzae* [43-45], pneumolysin [46] or its non-toxic derivatives [47], pneumococcal surface protein PspA [48], iron-uptake proteins [49], toxin A or B from *C. difficile* [50], recombinant *P. aeruginosa* exoprotein A (rEPA) [51], etc.

It is possible to use mixtures of proteins. A single protein may carry multiple different saccharides [52].

Diphtheria toxoid, tetanus toxoid, $CRM_{197}$ and protein D are particularly envisaged for use in the conjugate of an antigen to the first carrier.

The invention involves the use of a conjugate of an antigen associated with a second carrier. The second carrier facilitates immobilization of the antigen and may ensure a good degree of detection of the antibody in the sample.

Proteins suitable for use in the conjugate of an antigen associated with the first carrier are also suitable for use in the conjugate of an antigen associated with the second carrier. The inventors have found that serum albumin, particularly human serum albumin, more particularly recombinant human serum albumin, is suitable for use in the conjugate of an antigen associated with the second carrier.

The Aassociation

A large number of types of associations between an antigen and a carrier are known in the art, particularly when the antigen is a saccharide and the carrier a protein, as detailed below. Associations may be covalent or non-covalent. Non-covalent associations include electrostatic interactions and physical mixtures. Covalent associations may be selected from the group comprising a linker group of one or more atoms, and a direct bond.

In the present invention, any associations may be used, provided that in the first and second aspects of the invention, and typically in the third aspect of the invention, the association between the antigen and the first carrier (which may also be referred to as "the first association") is different from the association between the antigen and the second carrier (which may also be referred to as "the second association"). For example:
  I. The first and second associations are both covalent associations but each comprises a different linker group, or one is a direct bond and the other comprises a linker group.
  II. The first and second associations are both covalent associations but each is formed between a different part of the carrier (for example, where the carrier is a protein, a different residue of the protein).
  III. The first and second associations are both covalent associations but each is formed between a different part of the antigen (for example, where the antigen is a saccharide, a different residue of the saccharide).
  IV. Either the first or the second association is a covalent association and the other association is a non-covalent association.

These options are not mutually exclusive and may be combined, e.g. options I, II and III above. Suitably, the first association and the second association are covalent associations. Typically, the first association is a first covalent association comprising a linker group, and the second association is a second covalent association comprising a different linker group from the first covalent association Suitably, the antigen is a saccharide and the first and/or second carrier is a protein. Various methods are known for the conjugation of saccharides to a protein. In the present invention, any suitable conjugation reaction can be used, with any suitable linker where necessary. As used herein, the term "linker" refers to a divalent group of one or more atoms covalently bound to the residue of the antigen and the residue of the carrier.

A commonly used method for conjugating an antigen to a carrier protein, wherein the antigen is a saccharide, involves formation of an association between an aldehyde group in the saccharide and an amine group on the side chain of an amino acid residue in the protein, suitably a lysine residue. The association may be formed by reductive amination as described in references [53] and [54] for example. The aldehyde group in the saccharide may be generated by oxidation, for example, periodate oxidation. In the case of GBS saccharide, the aldehyde group may be formed on the aliphatic side chain of one or more sialic acid residues. This method may result in a conjugate of the antigen associated with the carrier (typically the first carrier in the present invention) wherein the association between the antigen and the carrier is a covalent association comprising the linker —$NHCH_2$—. In this linker the secondary amino group is typically contributed by the carrier and the carbon atom is typically the remainder of the aldehyde group following reductive amination.

Such a conjugate may be produced by a method comprising the following steps:
  (i) providing a saccharide that comprises a vicinal diol, or other group oxidizable to form an aldehyde;
  (ii) oxidizing said saccharide using, for example, periodate to provide an aldehyde group;
  (iii) providing a protein that comprises a free amine group;
  (iv) linking the protein to the product of step (ii) by reductive amination Where this first association is used, the second association in the methods of the present invention may be any other association known in the art. Specifically, it may be a association through a different residue on the protein and/or through a different linker group, Alternatively, it may be a non-covalent interaction, as illustrated in the examples, particularly when the second carrier is a protein such as HSA derivatized with a linker precursor as defined herein.

The conjugate of the antigen associated with the second carrier may suitably (and particularly in the case where the first association is a covalent association comprising the linker —$NHCH_2$—) comprise an association that is a covalent association comprising the linker —C(O)NHNHC(O)$L^1$C(O)NHNHC(O)— or the linker —C(O)NHNHC(O)$L^1$NHNHC(O)—. Typically, the second association comprises the linker —C(O)NHNHC(O)$L^1$C(O)NHNHC(O)—. In these linkers the carbonyl groups at each end of the linker are typically contributed by the antigen and the carrier. $L^1$ is a divalent radical selected from the group comprising alkylene, alkenylene, arylene, heteroarylene, arylalkylene, alkarylene, or alkylenearylalkylene. Preferably, $L^1$ is $C_{4-8}$ alkylene or phenylene (i.e. para-phenylene, meta-phenylene or otho-phenylene). $L^1$ may be $C_4$ alkylene or $C_8$ alkylene. Suitably, $L^1$ is $C_4$ alkylene. Where $L^1$ is $C_4$ alkylene, the linker precursor is ADH.

Such a conjugate may be produced by a method comprising the following steps:
  (i) providing a protein that comprises a free carboxyl group;
  (ii) reacting said protein with a carbodiimide;

(iii) providing a saccharide that comprises a free carboxyl group;

(iv) reacting said saccharide with a further carbodiimide; and either (v) reacting the O-acylisourea ester produced in step (ii) with a compound of the formula $H_2NHNC(O)L^1C(O)NHNH_2$; and (vi) reacting the O-acylisourea ester produced in step (iv) with the product of step (v); or (vii) reacting the O-acylisourea ester produced in step (iv) with a compound of the formula $H_2NHNC(O)L^1C(O)NHNH_2$; and (viii) reacting the O-acylisourea ester produced in step (ii) with the product of step (vii).

Typically, each carbodiimide may be of the formula RN=C=NR, wherein each substituent R is independently chosen from the group comprising $C_{1-8}$ alkyl, $C_{1-8}$ alkenyl, $C_{1-8}$alkenyl-$NR^a{}_2$; wherein each $R^a$ is selected from H and $C_{1-4}$ alkyl. Suitably, each carbodiimide may be 1-ethyl-3-(3-dimethylaminopropyl)carbodiimide (EDAC).

Alternatively, and particularly in the case where the first association is a covalent association comprising the linker —NHCH$_2$— and where the antigen is a saccharide, the second association may be a non-covalent interaction. In particular, the conjugate of the antigen associated with the second protein may be a non-covalent complex between the saccharide and a protein derivatized by converting a free carboxyl group to a group of the formula —C(O)NHNHC(O)L$^1$C(O)NHNH$_2$, wherein L$^1$ is as defined above.

Such a conjugate may be formed by a method comprising the following steps:

(i) providing a protein that comprises a free carboxyl group;

(ii) reacting said second protein with a carbodiimide;

(iii) reacting the resulting O-acylisourea ester with a compound of the formula $H_2NHNC(O)L^1C(O)NHNH_2$;

(iv) mixing the product of step (iii) with a saccharide.

In general, attachment of the saccharide antigen to the protein may be via a —NH$_2$ group e.g. in the side chain of a lysine residue in a protein, or of an arginine residue. Where a saccharide has a free aldehyde group then this can react with an amine in the protein to form a conjugate by reductive amination. Attachment to the protein may also be via a —SH group e.g. in the side chain of a cysteine residue. Alternatively the saccharide antigen may be attached to the protein via a linker group of one or more atoms.

The saccharide will typically be activated or functionalized prior to conjugation. Activation may involve, for example, cyanylating reagents such as CDAP (e.g. 1-cyano-4-dimethylamino pyridinium tetrafluoroborate [55, 56, etc.]). Other suitable techniques use carbodiimides, hydrazides, active esters, norborane, p-nitrobenzoic acid, N-hydroxysuccinimide, S-NHS, EDC, TSTU (see also the introduction to reference [57]).

Linkages via a linker group may be made using any known procedure, for example, the procedures described in references [58] and [59]. A preferred type of linker results from an adipic acid linker precursor, which may be formed by coupling a free —NH$_2$ group (possibly introduced to a saccharide by amination) with adipic acid (using, for example, diimide activation), and then coupling a protein to the resulting saccharide-adipic acid intermediate [60, 61, 62]. Another preferred type of linker is a carbonyl linker, which may be formed by reaction of a free hydroxyl group of the saccharide with carbonyldiimidazole (CDI) [63, 64] followed by reaction with a protein to form a carbamate association. Other linkers and linker precursors include β-propionamido [65], nitrophenyl-ethylamine [66], haloacyl halides [67], glycosidic associations [68], 6-aminocaproic acid [69], N-succinimidyl-3-(2-pyridyldithio)-propionate (SPDP) [70], adipic acid dihydrazide (ADH) [71], $C_4$ to $C_{12}$ moieties [72], etc. Carbodiimide condensation can also be used [73].

A process involving the introduction of amino groups into the saccharide (e.g. by replacing terminal =O groups with —NH$_2$) followed by derivatization with an adipic diester (e.g. adipic acid N-hydroxysuccinimido diester) and reaction with protein is typical.

A bifunctional linker precursor may be used to provide a first group for coupling to an amine group in the saccharide and a second group for coupling to the protein (typically for coupling to an amine in the protein).

The first group in the bifunctional linker precursor may thus be able to react with an amine group (—NH$_2$) on the saccharide. This reaction will typically involve an electrophilic substitution of the amines hydrogen. The second group in the bifunctional linker precursor is able to react with an amine group on the protein. This reaction will again typically involve an electrophilic substitution of the amine.

Where the reactions with both the saccharide and the protein involve amines then a bifunctional linker precursor may be used. For example, a homobifunctional linker precursor of the formula X-L-X may be used, where the two X groups are the same as each other and can react with the amines; and where L is a linking moiety in the linker. Similarly, a heterobifunctional linker precursor of the formula X-L-X may be used, where: the two X groups are different and can react with the amines; and where L is a linking moiety in the linker. A preferred X group is N-oxysuccinimide. L preferably has formula —C(O)-L$^1$-C(O)—. Preferred L$^1$ groups are defined herein.

A further example of a homobifunctional linker precursor is a linker precursor of the formula Y-L-Y, where each Y group comprises a primary amine group that can react with a carbonyl group, possibly activated by CDI. A typical Y group is a —NHNH$_2$ group. L typically has formula —C(O)-L$^1$-C(O)—, where L$^1$ is as defined herein, particularly —(CH$_2$)$_4$—. A typical additional linker precursor is thus adipic acid dihydrazide (ADH), and the inventors have found this compound to be particularly suitable as the linker precursor for the invention. However, shorter additional linker precursors may be used, and the inventors have found that carbodihydrazine (CDH, i.e. Y-L-Y, wherein Y is —NHNH$_2$ and L is carbonyl) is also particularly suitable as the linker precursor for the invention.

Other X groups are those which form esters when combined with HO-L$^1$-OH, such as norborane, p-nitrobenzoic acid, and sulfo-N-hydroxysuccinimide.

Further bifunctional linker precursors for use with the invention include acryloyl halides (e.g. chloride), haloacyl-halides and dihydrazides. Dihydrazides include ADH and sebacic acid dihydrazide.

The linker precursor will generally be added in molar excess to saccharide.

The resultant conjugates may have excess protein (w/w) or excess saccharide (w/w) e.g. in the ratio range of 1:5 to 5:1. Conjugates with excess protein are typical e.g. in the range 0.2:1 to 0.9:1, or equal weights. The conjugate may include small amounts of free (i.e. unconjugated) protein [74]. When a given protein is present in both free and conjugated form in a composition of the invention, the unconjugated form is preferably no more than 5% of the total amount of the protein in the composition as a whole, and more preferably present at less than 2% (by weight).

Conjugation of GBS saccharides has been widely reported e.g. see references [75], [76], [77], [78], [79], [80], [81], [82] and [83]. The typical prior art process for GBS saccharide conjugation typically involves reductive amination of a purified saccharide to a protein. The reductive amination involves an amine group on the side chain of an amino acid in the protein and an aldehyde group in the saccharide. As GBS capsular saccharides do not include an aldehyde group in their natural form then this is typically generated before conjugation by oxidation (e.g. periodate oxidation) of a portion (e.g. between 5 and 40%, particularly between 10 and 30%, preferably about 20%) of the saccharide's sialic acid residues [76,84]. Conjugate vaccines prepared in this manner have been shown to be safe and immunogenic in humans for each of GBS serotypes Ia, Ib, II, III, and V [85]. However, when the invention uses a serotype V capsular saccharide that is desialylated, then an aldehyde group may be generated in this saccharide before conjugation by oxidation (e.g. periodate oxidation) of a portion (e.g. between 5 and 40%, particularly between 10 and 30%, preferably about 20%) of the galactose residues of the saccharide [86]. An alternative conjugation process involves the use of —$NH_2$ groups in the saccharide (either from de-N-acetylation, or after introduction of amines) in conjunction with bifunctional linkers, as described in ref. [87]. A further alternative process is described in refs. [88] and [89]. In this process, the free aldehyde groups of terminal 2,5-anhydro-D-mannose residues (produced by depolymerization of type II or type III capsular saccharides by mild deaminative cleavage) are used for conjugation by reductive amination.

The Antibody

In the first and second aspects of the invention, the antibody is suitably an immunoglobulin A (IgA) or immunoglobulin G (IgG) antibody, particularly an IgG antibody. Suitable IgG antibodies include IgG1, IgG2, IgG3 and IgG4. Suitable IgA antibodies include IgA1 and IgA2. Typically the antibody will be a plurality of antibodies in the sample that bind to the conjugate, e.g. when the sample is serum from a subject who has been immunized with the conjugate. The plurality of antibodies may bind to the antigen in the conjugate with different specificities and/or affinities. The method will typically involve detection in the sample of the plurality of antibodies to the conjugate. In this way, it is possible to measure the overall antibody response of a subject to the conjugate; the different antibodies that are raised to the antigen during the response are detected in the method.

In the third aspect of the invention, the antibody is preferably a monoclonal antibody. The antibody binds to the conjugate of an antigen associated with a first carrier by a first association, in particular to the antigen within the conjugate. The epitope or epitopes to which the antibody binds are also present in the conjugate of the antigen associated with a second carrier by a second association, such that binding to the antigen associated with the second carrier is inhibited by the presence of the antigen associated with the first carrier in the vaccine batch. The antibody may be obtained from any source. Suitably, when the antigen is bacterial, the antibody is a bactericidal antibody. For the purposes of this disclosure, bactericidal antibodies include any antibody that binds to an epitope bound by bactericidal antibodies. Therefore, bactericidal antibodies include natural and synthetic antibodies (e.g. engineered antibodies such as chimeric antibodies, humanized antibodies, complementarity determining region (CDR)-grafted antibodies, veneered antibodies, phage-display isolated antibodies, minibodies, other engineered scaffold proteins, etc.). Typically, the bactericidal antibodies will not cross-react (i.e. they will only bind to the antigen of interest and do not bind to any other antigens that may be present in the vaccine. One of skill in the art can readily screen for bactericidal antibodies that do not cross react. Monoclonal antibodies are preferred, but polyclonal antibodies may be used. One of skill in the art could readily remove cross-reacting antibodies in a polyclonal antibody sample including, by way of example, by running the polyclonal antibody sample through a chromatography column with immobilized antigens from the other components in the vaccine.

One of skill in the art would understand that antigens of interest in any form may be used to generate antibodies, in particular, bactericidal antibodies, that may be used in the invention. Any method that can be used to generate antibodies may be used, such as immunization of an animal with a humoral immune system, antibody phage display screened against the antigen of interest, etc. In certain embodiments, the bactericidal antibody may be in the form of an antibody containing serum sample, polyclonal antibodies, antigen-purified polyclonal antibodies or monoclonal antibodies.

When the antigen in the third aspect of the invention is a GBS type III capsular saccharide the antibody may in particular be an antibody comprising at least one variable region comprising an amino acid sequence with at least about 95% sequence identity, more preferably at least about 99% sequence identity, and typically about 100% sequence identity, to a variable region within SEQ ID NO. 2 or a variable region within SEQ ID NO. 4. In particular, the antibody may comprise a light chain variable region ($V_L$) comprising an amino acid sequence with at least about 95% sequence identity, more preferably at least about 99% sequence identity, and typically about 100% sequence identity, to a variable region within SEQ ID NO: 2 and a heavy chain variable region ($V_H$) comprising an amino acid sequence with at least about 95% sequence identity, more preferably at least about 99% sequence identity, and typically about 100% sequence identity, to a variable region within SEQ ID NO: 4. In particular, the variable region within SEQ ID NO. 2 may be the amino acid sequence as set out in SEQ ID NO. 13. Similarly, the variable region within SEQ ID NO. 4 may be the amino acid sequence as set out in SEQ ID NO. 14.

In these embodiments when the antigen in the third aspect is a GBS type III capsular saccharide, the antibody may in particular be an antibody comprising a light chain third CDR (LC-CDR3) comprising the amino acid sequence set out in SEQ ID NO. 33 and/or a heavy chain third CDR (HC-CDR3) comprising the amino acid sequence set out in SEQ ID NO. 24. Typically, the antibody comprises both of these CDR3s. When the antibody comprises an LC-CDR3 comprising the amino acid sequence set out in SEQ ID NO. 33, the antibody typically also comprises the light chain first CDR (LC-CDR1) and light chain second CDR (LC-CDR2) set out in SEQ ID NOs. 31 and 32 respectively. Similarly, when the antibody comprises an HC-CDR3 comprising the amino acid sequence set out in SEQ ID NO. 24, the antibody typically also comprises the heavy chain first CDR (HC-CDR1) and heavy chain second CDR (HC-CDR2) set out in SEQ ID NOs. 22 and 23 respectively. Typically, the antibody comprises all six of these CDRs. Each CDR may comprise one or more conservative amino acid substitutions, although typically no such mutations are present.

In the embodiments of the two paragraphs above, the antibody specifically binds to GBS type III capsular saccharide, typically with an affinity ($K_D$) of ≤10 nM, preferably ≤5 nM and, more preferably, ≤2.5 nM. The affinity may be measured by surface plasmon resonance, for example, according to the protocol of example 13a. Preferably, the antibody shows functional activity, e.g. as measured by GBS killing in opsonophagocytic assay (OPA) according to the protocol of Example 13b. Preferably, the antibody shows an OPA titre (antibody dilution mediating 50% of killing) of ≥50, more preferably ≥150 and more preferably, ≥500.

When the antigen in the third aspect of the invention is a GBS type Ib capsular saccharide the antibody may in particular be an antibody comprising at least one variable region comprising an amino acid sequence with at least about 95% sequence identity, more preferably at least about 99% sequence identity, and typically about 100% sequence identity, to a variable region within SEQ ID NO. 6 or a variable region within SEQ ID NO. 8. In particular, the antibody may comprise a light chain variable region ($V_L$) comprising an amino acid sequence with at least about 95% sequence identity, more preferably at least about 99% sequence identity, and typically about 100% sequence identity, to a variable region within SEQ ID NO: 6 and a heavy chain variable region ($V_H$) comprising an amino acid sequence with at least about 95% sequence identity, more preferably at least about 99% sequence identity, and typically about 100% sequence identity, to a variable region within SEQ ID NO: 8. In particular, the variable region within SEQ ID NO. 6 may be the amino acid sequence as set out in SEQ ID NO. 15. Similarly, the variable region within SEQ ID NO. 8 may be the amino acid sequence as set out in SEQ ID NO. 16.

In these embodiments when the antigen in the third aspect is a GBS type Ib capsular saccharide, the antibody may in particular be an antibody comprising a light chain third CDR (LC-CDR3) comprising the amino acid sequence set out in SEQ ID NO. 27 and/or a heavy chain third CDR (HC-CDR3) comprising the amino acid sequence set out in SEQ ID NO. 30. Typically, the antibody comprises both of these CDR3s. When the antibody comprises an LC-CDR3 comprising the amino acid sequence set out in SEQ ID NO. 27, the antibody typically also comprises the light chain first CDR (LC-CDR1) and light chain second CDR (LC-CDR2) set out in SEQ ID NOs. 25 and 26 respectively. Similarly, when the antibody comprises an HC-CDR3 comprising the amino acid sequence set out in SEQ ID NO. 30, the antibody typically also comprises the heavy chain first CDR (HC-CDR1) and heavy chain second CDR (HC-CDR2) set out in SEQ ID NOs. 28 and 29 respectively. Typically, the antibody comprises all six of these CDRs. Each CDR may comprise one or more conservative amino acid substitutions, although typically no such mutations are present.

In the embodiments of the two paragraphs above, the antibody specifically binds to GBS type Ib capsular saccharide, typically with an affinity ($K_D$) of ≤1 nM, preferably ≤0.5 nM and, more preferably, ≤0.1 nM. The affinity may be measured by surface plasmon resonance, for example, according to the protocol of Example 13a. Preferably, the antibody shows functional activity, e.g. as measured by GBS killing in an OPA assay according to the protocol of Example 13b. Preferably, the antibody shows an OPA titre of ≥100, more preferably ≥500 and more preferably, ≥900.

When the antigen in the third aspect of the invention is a GBS type Ia capsular saccharide the antibody may in particular be an antibody comprising at least one variable region comprising an amino acid sequence with at least about 95% sequence identity, more preferably at least about 99% sequence identity, and typically about 100% sequence identity, to a variable region within SEQ ID NO. 10 or a variable region within SEQ ID NO. 12. In particular, the antibody may comprise a light chain variable region ($V_L$) comprising an amino acid sequence with at least about 95% sequence identity, more preferably at least about 99% sequence identity, and typically about 100% sequence identity, to a variable region within SEQ ID NO: 10 and a heavy chain variable region ($V_H$) comprising an amino acid sequence with at least about 95% sequence identity, more preferably at least about 99% sequence identity, and typically about 100% sequence identity, to a variable region within SEQ ID NO: 12.

In these embodiments when the antigen in the third aspect is a GBS type Ia capsular saccharide, the antibody may in particular be an antibody comprising a light chain third CDR (LC-CDR3) comprising the amino acid sequence set out in SEQ ID NO. 21 and/or a heavy chain third CDR (HC-CDR3) comprising the amino acid sequence set out in SEQ ID NO. 36. Typically, the antibody comprises both of these CDR3s. When the antibody comprises an LC-CDR3 comprising the amino acid sequence set out in SEQ ID NO. 21, the antibody typically also comprises the light chain first CDR (LC-CDR1) and light chain second CDR (LC-CDR2) set out in SEQ ID NOs. 19 and 20 respectively. Similarly, when the antibody comprises an HC-CDR3 comprising the amino acid sequence set out in SEQ ID NO. 36, the antibody typically also comprises the heavy chain first CDR (HC-CDR1) and heavy chain second CDR (HC-CDR2) set out in SEQ ID NOs. 34 and 35 respectively. Typically, the antibody comprises all six of these CDRs. Each CDR may comprise one or more conservative amino acid substitutions, although typically no such mutations are present.

In the embodiments of the two paragraphs above, the antibody specifically binds to GBS type Ia capsular saccharide, typically with an affinity ($K_D$) of ≤5 nM, preferably ≤2.5 nM and, more preferably, ≤0.75 nM. The affinity may be measured by surface plasmon resonance, for example, according to the protocol of example 13a. Preferably, the antibody shows functional activity, e.g. as measured by GBS killing in an OPA assay according to the protocol of example 13b. Preferably, the antibody shows an OPA titre of ≥60, more preferably ≥150 and more preferably, ≥500. In particular, the variable region within SEQ ID NO. 10 may be the amino acid sequence as set out in SEQ ID NO. 17. Similarly, the variable region within SEQ ID NO. 12 may be the amino acid sequence as set out in SEQ ID NO. 18.

The antibody preferably binds to an epitope in the GBS capsular saccharide that comprises sialic acid. The ability of an antibody to bind to an epitope in the GBS capsular saccharide that comprises sialic acid can be assessed by epitope mapping, for example, as in Example 13d. The presence of sialic acid in the lateral chain of the repeating unit of the GBS polysaccharide is thought to affect the potency of GBS conjugate vaccines, in particular, the potency of GBS III conjugate vaccines. Specifically, interaction of sialic acid with the GBS backbone is thought to be important for defining the immunodominant conformational epitope of native GBS. Therefore, degradation of the chemically labile glycosidic bond of sialic acid can result in vaccine batches with reduced potency. Preferably, antibodies of the present invention bind to an epitope that comprises sialic acid and, as a result, can be used to discriminate such sub-potent vaccine batches from those in which sialic acid is not degraded. In this way, the method of the third aspect of the invention can be applied to assays to discriminate sub-potent vaccine batches, that is, vaccine batches with low sialic acid content.

The invention also provides isolated antibodies as described herein. These antibodies are suitable for use, for example, as research tools. Specific antibody molecules may carry a detectable label, or may be conjugated to an enzyme (e.g. via a peptidyl bond or linker). Such antibody molecule compositions form an additional aspect of the present invention.

Fragments of an antibody that retain the ability to bind to the relevant antigen may be inserted into various frameworks, see, for example, Ref. 90 which discusses various scaffolds which may be used to display antibody loops previously selected on the basis of antigen binding. In addition, genes encoding for $V_L$ and $V_H$ can be joined, using recombinant methods, for example using a synthetic linker that enables them to be made as a single protein chain in which the $V_L$ and $V_H$ regions pair to form monovalent molecules, otherwise known as single chain Fvs (ScFvs) [91,92].

In specific embodiments, a variable heavy domain is paired with a variable light domain to provide an antigen binding site. Alternatively, independent regions (e.g. a variable heavy domain alone) may be used to bind antigen. The skilled person is also aware that two domains of an Fv fragment, $V_L$ and $V_H$, while perhaps coded by separate genes, may be joined, using recombinant methods, by a synthetic linker that enables them to be made as a single protein chain in which the $V_L$ and $V_H$ regions pair to form monovalent molecules (scFvs).

Manipulation of monoclonal and other antibodies to produce other antibodies or chimeric molecules which retain the specificity of the original antibody is also known to the skilled person. Specific immunoglobulins, into which the disclosed sequences may be inserted or, in the alternative, form the essential part of, include but are not limited to the following antibody molecules which form particular embodiments of the present invention: a Fab (monovalent fragment with $V_L$, $V_H$, constant light ($C_L$) and constant heavy 1 ($C_{H1}$) domains), a F(ab')$_2$ (bivalent fragment comprising two Fab fragments linked by a disulfide bridge or alternative at the hinge region), a Fd ($V_H$ and $C_{H1}$ domains), a Fv ($V_L$ and $V_H$ domains), a scFv (a single chain Fv where $V_L$ and $V_H$ are joined by a linker, e.g. a peptide linker [91,92], IgG, IgG1, IgG2, IgG3, IgG4, IgM, IgD, IgA, IgE, or any derivatives thereof.

Specific antibodies of the present invention are monoclonal antibodies and, in particular embodiments, are in one of the following antibody formats: IgD, IgA, IgE, IgM, IgG1, IgG2, IgG3, IgG4 or any derivative thereof. In particular, the antibody may be an IgG antibody or a derivative. The language "derivatives thereof" or "derivatives" includes, inter alia, (i) antibodies and antibody molecules with modifications in the framework or CDR regions of one or both variable regions (i.e. $V_H$ and/or $V_L$), (ii) antibodies and antibody molecules with manipulations in the constant regions of the heavy and/or light chains, and (iii) antibodies and antibody molecules that contain additional chemical moieties which are not normally a part of the immunoglobulin molecule (e.g. pegylation). Available techniques exist to recombinantly produce other antibody molecules which retain the specificity of an original antibody. A specific example of this is where DNA encoding the immunoglobulin variable region or the CDRs is introduced into the constant regions, or constant regions and framework regions, of another antibody molecule [93,94,95]. Cloning and expression of antibody molecules, including chimeric antibodies, are described in the literature [96,97].

Also provided is an isolated nucleic acid encoding at least one antibody or variable region as defined above or a component thereof. The isolated nucleic acid encoding the variable regions can be provided within any desired antibody molecule format including, but not limited to, the following: F(ab')$_2$, a Fab, a Fv, a scFv, IgG, IgG1, IgG2, IgG3, IgG4, IgM, IgD, IgA, IgE or any derivatives thereof.

Preferably, the nucleic acid encodes at least one amino acid sequence selected from SEQ ID NO. 13, 14, 15, 16, 17 or 18, for example, a nucleic acid comprising a nucleic acid sequence selected from SEQ ID NO. 1, 3, 5, 7, 9 or 11. In particular, the nucleic acid may encode (a) SEQ ID NO. 13 and SEQ ID NO. 14; (b) SEQ ID NO. 15 ng SEQ ID NO. 16; or (c) SEQ ID NO. 17 and SEQ ID NO. 18. For example, the nucleic acid may comprise (a) SEQ ID NO. 1 and SEQ ID NO. 3; (b) SEQ ID NO. 5 and SEQ ID NO. 7; or (c) SEQ ID NO. 9 and SEQ ID NO. 11. Alternatively, the amino acid sequences may be encoded by separate nucleic acids, and the invention provides these nucleic acids in combination. For example, the invention provides (a) a nucleic acid that encodes SEQ ID NO. 13 and a nucleic acid that encodes SEQ ID NO. 14; (b) a nucleic acid that encodes SEQ ID NO. 15 and a nucleic acid that encodes SEQ ID NO. 16; and (c) a nucleic acid that encodes SEQ ID NO. 17 and a nucleic acid that encodes SEQ ID NO. 18. Also included within the present invention are nucleic acids including nucleotide sequences which are at least about 90% identical and more preferably at least about 95% identical to the nucleotide sequences described herein, and which nucleotide sequences encode antibodies or variable domains of the present invention.

In another aspect, the present invention provides vectors including said nucleic acid(s). Vectors in accordance with the present invention include, but are not limited to, plasmids and other expression constructs (e.g. phage or phagemid, as appropriate) suitable for the expression of the desired antibody molecule at the appropriate level for the intended purpose; see, for example, ref. [98]. The antibody light chain gene and the antibody heavy chain gene can be inserted into separate vectors or, more typically, both genes are inserted into the same expression vector. The antibody genes are inserted into the expression vector by standard methods (e.g. ligation of complementary restriction sites on the antibody gene fragment and vector, or blunt-end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e. a signal peptide from a non-immunoglobulin protein). Any technique available to the skilled peron may be employed to introduce the nucleic acid into the host cell, for example, those described in ref. [99].

In another aspect, the present invention provides a host cell transformed with said nucleic acid(s) or vector(s). A variety of different cell lines can be used for recombinant production of antibody molecules, including but not limited to those from prokaryotic organisms (e.g. *E. coli, Bacillus*, and *Streptomyces*) and from eukaryotic (e.g. yeast, Baculovirus, and mammalian) [100].

In another aspect, the present invention provides isolated cell(s) comprising a polypeptide of the present invention.

In another aspect, the present invention provides a method of making an antibody molecule of the present invention, which involves incubating a host cell of the invention under conditions that allow the expression and assembly of said heavy and/or light chains into an antibody molecule, and isolating said antibody molecule from the cell.

Further Features of the Invention

Suitably the conjugate of the antigen associated with a second carrier is immobilized on a surface, particularly a multiwell plate.

The agent to detect the presence of the antibody may be a labelled antibody to the antibody. For example, the antibody to the antibody may be labelled with a moiety, such as an enzyme, that interacts with an indicator to give a detectable spectrophotometric, colorimetric, fluorimetric, luminescent, electrochemical or radioactive signal. Suitably, the agent is an antibody to the antibody that is conjugated to an enzyme selected from the group consisting of laccase (CotA enzyme), alkaline phosphatase, p-galactosidase, acetylcholinesterase, green fluorescent proteins, luciferases or horseradish peroxidases. Suitably, the agent is an alkaline phosphatase-conjugated antibody to the antibody.

Suitably, the method of the first aspect of the invention is for measuring the concentration of the antibody in the sample, e.g. as an antibody titre. The concentration may be compared with a standard criterion for seroprotection for the antigen. For example, the standard criterion may be a concentration suitable to prevent infection resulting in symptomatic disease. The concentration may be measured after administration of the conjugate to a subject and collection of a sample from the subject, e.g. in order to verify the effect of the conjugate. The method may also be used to test subjects for existing antibody levels to identify those that may require vaccination with the conjugate.

In an alternative example, the standard criterion may be a concentration suitable to prevent neonatal infection during childbirth. The methods, kits and conjugates of the present invention are useful in methods of providing for use by physicians a vaccine comprising a conjugate of an antigen associated with a first carrier by a first association, comprising the steps of: (a) administering the vaccine to a plurality of subjects; (b) collecting samples from the subjects; (c) measuring the concentration of antibody to the conjugate in each sample using a method according to the first aspect of the invention; (d) comparing the concentration with a standard criterion for seroprotection for the antigen; and, if the comparison in step (d) indicates a concentration equal or superior to the criterion for seroprotection for a predetermined proportion of subjects, (e) providing the vaccine for use by physicians.

The criterion for seroprotection for an antigen is typically an associated antibody titre above which a host is considered to be seroconverted against the antigen. Such titres are well known and are published by organisations such as WHO. For example, studies have identified in maternal blood particular anti-GBS immunoglobulin G concentrations that account for a decreased probability of neonatal infection with serotypes Ia or III [101, 102]. Therefore, a subject who has a serum level of immunoglobulin G against a given GBS antigen of $\geq 0.5$ µg/ml or $\geq 2$ µg/ml, or particularly $\geq 5$ µg/ml, or more particularly $\geq 10$ µg/ml may be considered to be seroconverted against that antigen. Preferably, more than 80% of a statistically significant sample of subjects is seroconverted, more preferably more than 90%, still more preferably more than 93% and most preferably 96-100%.

The methods, kits and conjugates of the present invention are useful in methods of testing a subject's immune response to a conjugate of an antigen associated with a first carrier by a first association. Such methods may comprise the steps of
(i) administering to said subject said conjugate of an antigen associated with a first carrier by a first association;
(ii) obtaining a sample from said subject;
(iii) contacting a conjugate of the antigen associated with a second carrier by a second association with said sample under conditions that allow binding of the antibody to the antigen, wherein said conjugate is immobilized on a surface; and
(iv) introducing an agent to detect the presence of the antibody bound to said antigen;
wherein the first association is different from the second association.

The third aspect of the invention involves release of a batch of a vaccine that comprises a conjugate of an antigen associated with a first carrier by a first association. "Release" within this context includes release for use in patients, i.e. providing the batch for medical use. Any form of release is envisaged, both commercial and non-commercial. Accordingly, the concept of "release" includes putting the batch onto the market for purchase by healthcare providers and/or private individuals, and also donating the batch for charitable use. The batch is typically the stock of vaccine made from a single run of the vaccine's manufacturing process. The method involves a portion of this batch, which is selected to be representative of the batch as a whole.

In order to be released, the batch may be required to meet regulatory requirements for release. The regulatory requirements may comprise a minimum potency (e.g. immunogenicity) requirement and a measurement reliability requirement. The measurement reliability requirement may be the variation of the measurements being less than a maximum value, for example, 15%. The regulatory requirements may be those determined by, for example, the U.S. Food and Drug Administration or the European Medicines Agency. The method uses binding of the antibody to the vaccine batch as a proxy to assess potency (e.g. immunogenicity). This binding is measured indirectly by assessing the extent to which the batch can compete with the antigen associated with a second carrier by a second association for binding to the antibody. This competition is compared to the competition observed with a reference vaccine instead of the vaccine batch. The reference vaccine comprises the conjugate of an antigen associated with a first carrier by a first association and may be known to meet the regulatory requirements for release. The reference vaccine may comprise other antigens in addition to the conjugate. For example, it may contain one or more other conjugates of an antigen associated with a carrier by an association as defined above. In particular, it may be a multivalent GBS conjugate vaccine as described in ref. [103], especially the multivalent GBS vaccines described in the claims and examples of that document.

Methods according to the third aspect of the invention may further comprise steps wherein step (a) to (c) are repeated with serial dilutions of the reference vaccine and/or portion of the vaccine batch. Typically, such methods include at least two, at least three, at least four or at least five serial dilutions of the reference vaccine and/or the portion of the vaccine batch. This facilitates the comparison in step (e).

In vitro methods according to the third aspect of the invention may measure vaccine potency with high reproducibility, specificity and sensitivity. For example, the methods show greater reproducibility and sensitivity than commonly used animal immunogenicity tests. The high specificity means that the assay allows the precise amount of either GBS Ia, GBS Ib or GBS III present in a sample of a trivalent GBS vaccine (i.e. one containing conjugates of GBS Ia, GBS Ib and GBS III, and $CRM_{197}$).

General

The practice of the present invention will employ, unless otherwise indicated, conventional methods of chemistry, biochemistry, molecular biology, immunology and pharmacology, within the skill of the art. Such techniques are explained fully in the literature. See, e.g., references 104-111, etc.

Where the invention concerns an "epitope", this epitope may be a B-cell epitope and/or a T-cell epitope. Such epitopes can be identified empirically (e.g. using PEPSCAN [112,113] or similar methods), or they can be predicted (e.g. using the Jameson-Wolf antigenic index [114], matrix-based approaches [115], MAPITOPE [116], TEPITOPE [117,118], neural networks [119], OptiMer & EpiMer [120, 121], ADEPT [122], Tsites [123], hydrophilicity [124], antigenic index [125] or the methods disclosed in references 126-130, etc.). Epitopes are the parts of an antigen that are recognized by and bind to the antigen binding sites of antibodies or T-cell receptors, and they may also be referred to as "antigenic determinants".

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 131. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 132. One method by which one skilled in the art could obtain an antibody having variable sequences having high (i.e. 95% or greater) homology to the variable sequences described herein is by mutagenesis (e.g. site-directed or random mutagenesis) of nucleic acid molecules encoding SEQ ID NOs: 2, 4 and 6 and/or SEQ ID NOs: 8, 10 and 12, followed by testing the encoded altered antibody for retained function using the functional assays described herein. Alternatively, homologous antibodies may be obtained through other antibody isolation approaches.

A "conservative amino acid substitution" is a substitution that replaces an amino acid residue with one imparting similar or better (for the intended purpose) functional and/or chemical characteristics. For example, conservative amino acid substitutions are often ones in which the amino acid residue is replaced with an amino acid residue having a similar side chain. Families of amino acid residues having similar side chains are known in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Such modifications in antibody CDRs may not significantly reduce or alter the binding or functional characteristics of the antibody containing the amino acid sequence and may sometimes improve such properties. Such modifications may be introduced by standard techniques known in the art, such as site-directed mutagenesis and PCR-mediated mutagenesis. One specific means by which the skilled person can accomplish conservative amino acid substitutions is alanine scanning mutagenesis. The altered antibody molecules are tested for retained or better function using functional assays, particularly those described herein.

Unless specifically defined elsewhere, the chemical groups discussed herein have the following meaning when used in present specification:

The term "alkyl" includes saturated hydrocarbon residues including:
  linear groups up to 10 atoms ($C_1$-$C_{10}$), or of up to 6 atoms ($C_1$-$C_6$), or of up to 4 atoms ($C_1$-$C_4$). Examples of such alkyl groups include, but are not limited, to $C_1$-methyl, $C_2$-ethyl, $C_3$-propyl and $C_4$-n-butyl.
  branched groups of between 3 and 10 atoms ($C_3$-$C_{10}$), or of up to 7 atoms ($C_3$-$C_7$), or of up to 4 atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

The term "alkylene" refers to the divalent hydrocarbon radical derived from an alkyl group, and shall be construed in accordance with the definition above.

The term "cycloalkyl" refers to a saturated monocyclic, bicyclic, or tricyclic hydrocarbon ring system having three to fourteen carbon atoms and zero heteroatoms.

The term "cycloalkylene" refers to the divalent hydrocarbon radical derived from a cycloalkyl group, and shall be construed in accordance with the definition above.

The term "alkenyl" includes monounsaturated hydrocarbon residues including:
  linear groups of between 2 and 6 atoms ($C_2$-$C_6$). Examples of such alkenyl groups include, but are not limited to, $C_2$-vinyl, $C_3$-1-propenyl, $C_3$-allyl, $C_4$-2-butenyl
  branched groups of between 3 and 8 atoms ($C_3$-$C_8$). Examples of such alkenyl groups include, but are not limited to, $C_4$-2-methyl-2-propenyl and $C_6$-2,3-dimethyl-2-butenyl.

The term alkenylene refers to the divalent hydrocarbon radical derived from an alkenyl group, and shall be construed in accordance with the definition above.

The term "cycloalkenyl," refers to a non-aromatic, partially unsaturated monocyclic, bicyclic, or tricyclic ring system having three to fourteen carbon atoms and zero heteroatoms.

The term "cycloalkenylene" refers to the divalent hydrocarbon radical derived from an cycloalkenyl group, and shall be construed in accordance with the definition abo.

The term "aryl" includes a single or fused aromatic ring system containing 6 or 10 carbon atoms; wherein, unless otherwise stated, each occurrence of aryl may be optionally substituted with up to 5 substituents independently selected from ($C_1$-$C_6$)alkyl, ($C_1$-$C_6$)alkoxy, OH, halo, CN, $COOR^{14}$, $CF_3$ and $NR^{14}R^{15}$; as defined above. Typically, aryl will be optionally substituted with 1, 2 or 3 substituents. Optional substituents are selected from those stated above. Examples of suitable aryl groups include phenyl and naphthyl (each optionally substituted as stated above). Arylene refers the divalent radical derived from an aryl group, and shall be construed in accordance with the definition above.

The term "heteroaryl" includes a 5, 6, 9 or 10 membered mono- or bi-cyclic aromatic ring, containing 1 or 2 N atoms and, optionally, an $NR^{14}$ atom, or one $NR^{14}$ atom and an S or an O atom, or one S atom, or one O atom; wherein, unless otherwise stated, said heteroaryl may be optionally substituted with 1, 2 or 3 substituents independently selected from $(C_1-C_6)$alkyl, $(C_1-C_6)$alkoxy, OH, halo, CN, $COOR^{14}$, $CF_3$ and $NR^{14}R^{15}$; as defined below. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Heteroarylene refers the divalent radical derived from heteroaryl, and shall be construed in accordance with the definition above.

The term "arylalkyl" refers to an alkyl group substituted with one, two, or three aryl groups.

The term "arylalkylene" refers to a divalent arylalkyl group, where one point of attachment to the parent molecular moiety is on the aryl portion and the other is on the alkyl portion.

The term "alkaryl" refers to an aryl group substituted with one, two, or three alkyl groups.

The term "alkarylene" refers to a divalent alkaryl group, where one point of attachment to the parent molecular moiety is on the alkyl portion and the other is on the aryl portion.

The term "alkylarylalkyl" refers to an alkylaryl group attached to the parent molecular moiety through an alkyl group.

The term "alkylarylalkylene" refers to a divalent alkylarylalkyl group, where one point of attachment to the parent molecular moiety is on one alkyl portion and the other is on the other alkyl portion.

In the above definitions $R^{14}$ and $R^{15}$ are independently selected from H and $(C_1-C_6)$alkyl.

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. The different steps can be performed at very different times by different people in different places (e.g. in different countries).

It will be appreciated that sugar rings can exist in open and closed form and that both forms are encompassed by the invention. Similarly, it will be appreciated that sugars can exist in pyranose and furanose forms and that both forms are also encompassed. Different anomeric forms of sugars are also encompassed.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

BRIEF DESCRIPTION OF DRAWINGS

FIG. 8 shows Western blot analysis of conjugates of GBS Ib-HSA-ADH using anti-GBS Ib CRM197.

FIG. 10a shows in schematic the production of $CRM_{197}$-GBS Ia conjugate vaccine (free polysaccharide<10%).

FIG. 10b shows in schematic the production of HSA-GBS Ia ELISA coating reagent. (free polysaccharide<10%).

FIG. 11 shows inhibition by pre-incubation of the native polysaccharide of the immunoglobulin G (IgG) responses obtained by ELISA analysis of sera from animals immunized with $CRM_{197}$-conjugated Ia (FIGS. 11a and 11b), Ib (FIG. 11c) and III (FIG. 11d) polysaccharides, expressed as a percentage of the response obtained without the inhibitor.

MODES FOR CARRYING OUT THE INVENTION

EXAMPLE 1

Production of Polysaccharide Derivatized with ADH

Figure 1A:
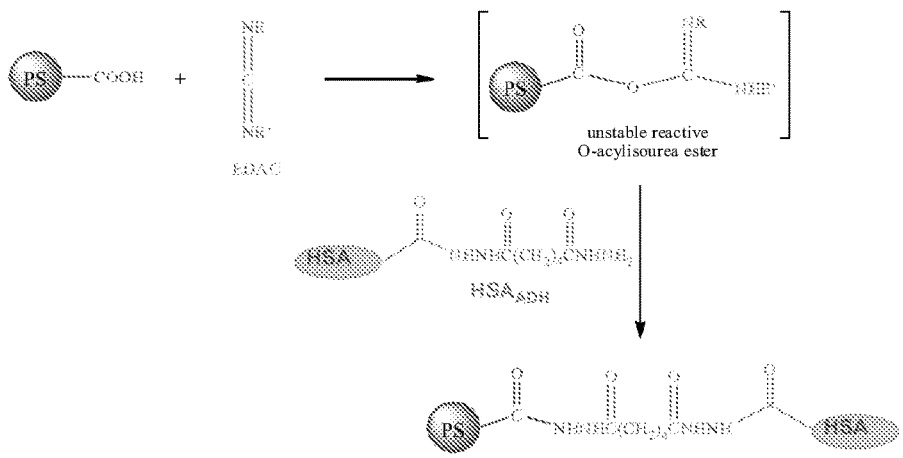
FIG. 1 shows synthetic routes to (a) a polysaccharide-HSA conjugate linked by ADH, (b) a polysaccharide derivatized with ADH and (c) human serum albumin derivatized with ADH.
Figure 1B:
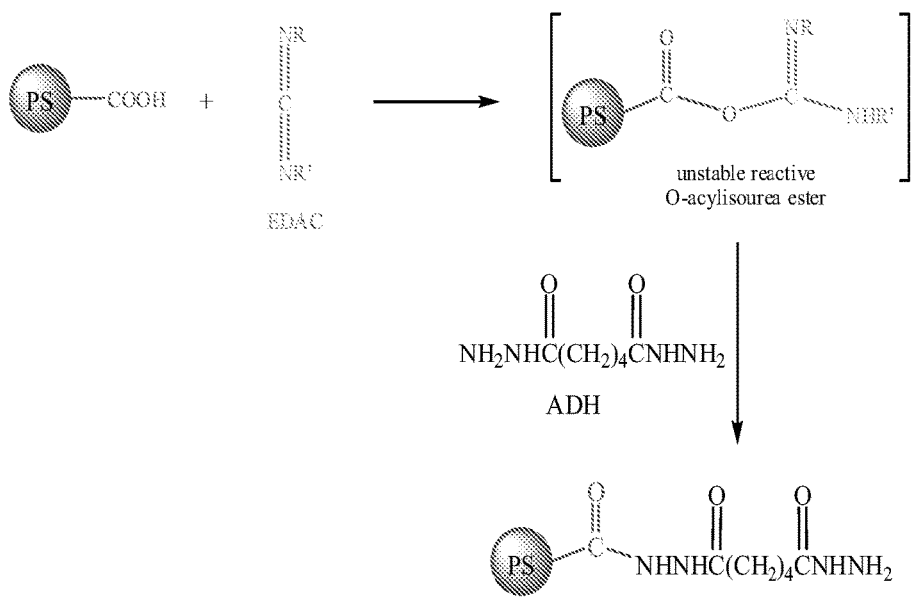

GBS polysaccharide was derivatized with ADH according to scheme in FIG. 1b.

GBS saccharide Ib Lot TR19 (liquid, K$^+$) and Lot TR8 (solid, Ca$^{2+}$) was mixed with ADH (Sigma; molar ratio of ADH to polysaccharide repeating unit of 20:1), EDAC (Sigma; molar ratio of EDAC to polysaccharide repeating unit of 3:10 or 1:1) in MES 100 mM/NaCl 250 mM pH 5.0 and stirred for 1 h at room temperature. Purification was by PD10 column in H$_2$O. The percentage derivatization with ADH was determined and is shown in Table 1.

TABLE 1

| Amine group analysis using ADH for the standard curve | |
|---|---|
| Sample | % Derivatization ADH |
| PS Ib Lot TR19 (EDAC 30%) | 4.26 |
| PS Ib Lot TR19 (EDAC 100%) | 6.26 |
| PS Ib Lot TR8 (EDAC 100%) | 6.51 |

EXAMPLE 2

Production of HSA-ADH

Figure 1C:
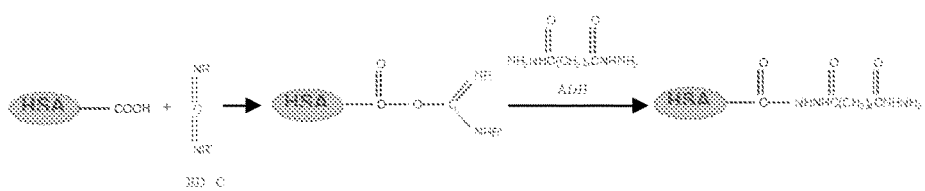

HSA was derivatized with ADH according to the scheme in FIG. 1c under conditions to introduce different numbers of moles of ADH.

EXAMPLE 2a

Production of HSA-ADH by Introduction of 10-12 mol of ADH

Figure 2A:
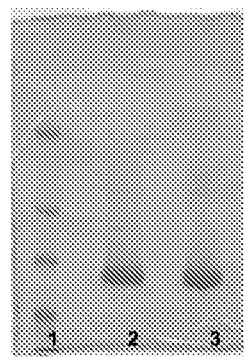
FIG. 2 shows SDS-PAGE analysis of HSA derivatized by introduction of (a) 10-12 mol or (b) 26-28 mol of ADH.

HSA (10-12 mg/ml), ADH (molADH:molCOOH$_{TOT}$HSA=13.4:1) and EDAC (Sigma; molEDAC:molCOOH$_{TOT}$HSA=1:2) in 100 mM MES buffer at pH 6.0 were mixed for 1 hour at room temperature. Purification was by dialysis with 6-8 kDa membrane against MES 10 mM/NaCl 150 mM pH 6.0 and then against MES 5 mM pH 7.0 at 4° C. with slow stirring. The resultant conjugates were analysed by SDS-PAGE (FIG. 2a).

EXAMPLE 2b

Production of HSA-ADH by Introduction of 26-28 mol of ADH

Figure 2B:
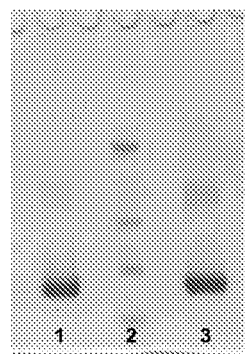

HSA (10-12 mg/ml), ADH (molADH:molCOOH$_{TOT}$HSA=13.4:1) and EDAC (molEDAC:molCOOH$_{TOT}$HSA=2:1) in 100 mM MES buffer at pH 5.0 were mixed for 3 hours at room temperature. Purification was by dialysis with 6-8 kDa membrane against MES 5 mM/NaCl 150 mM pH 7.2 and then against MES 5 mM pH 7.0 at 4° C. with slow stirring. The resultant conjugates were analysed by SDS-PAGE (FIG. 2b).

EXAMPLE 2c

Characterization of HSA-ADH Conjugates

Figure 3A:
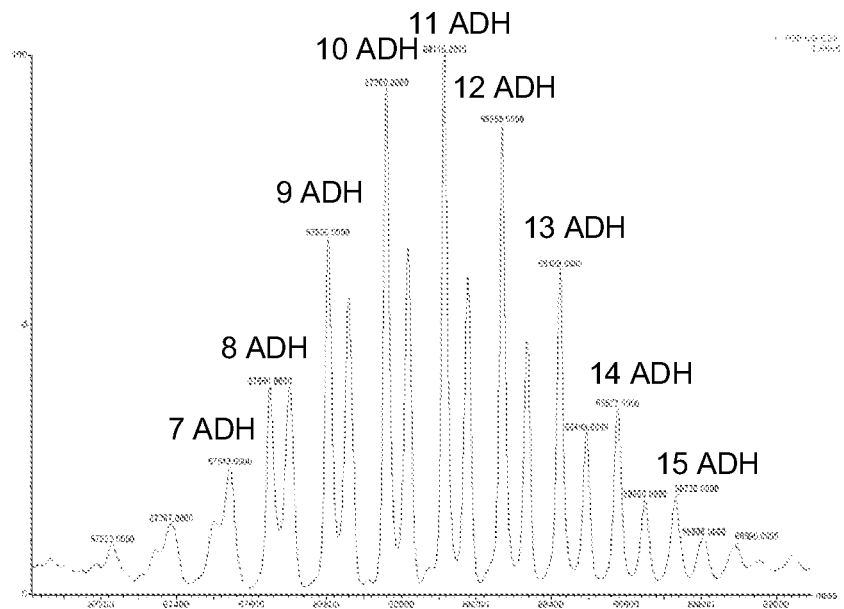
FIG. 3 shows characterization by mass spectrometry (MS) of HSA derivatized by introduction of (a) 10-12 mol or (b) 26-28 mol of ADH and (c) HSA as supplied by Sigma.
Figure 3B:
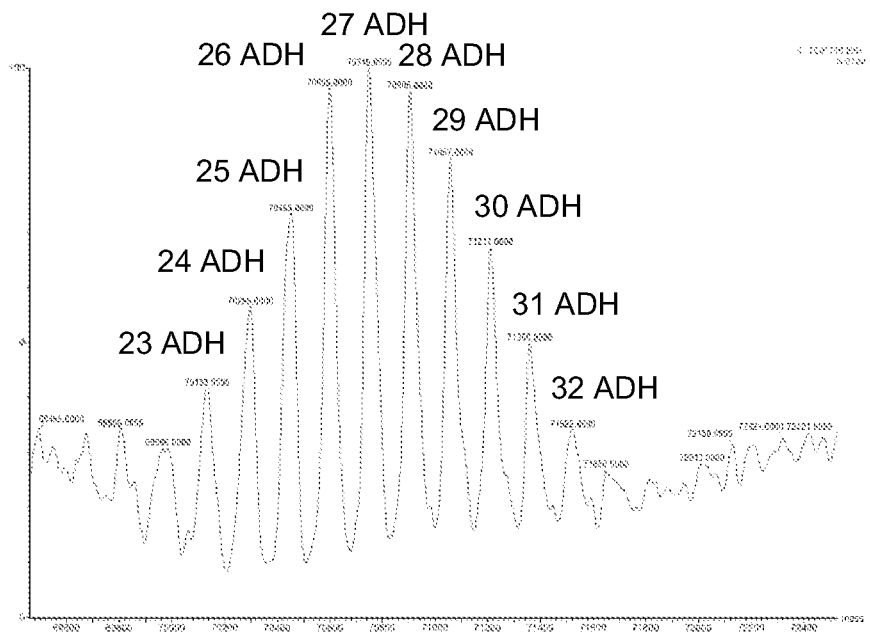
Figure 3C:
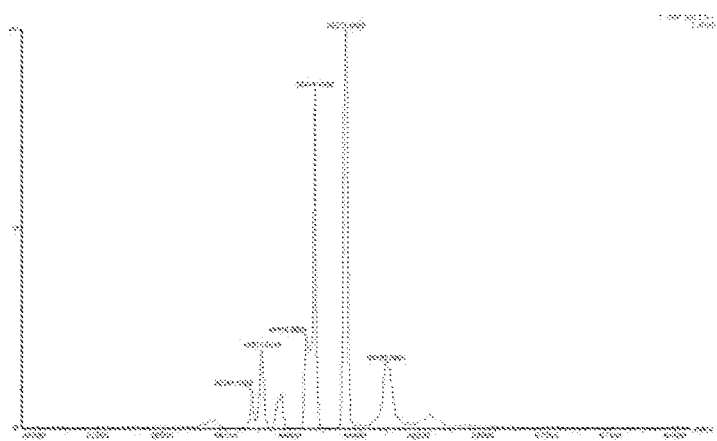

The HSA-ADH conjugates were characterized by MS. ESI+ Capillary 3 kV Sample cone 30V Direct infusion 10 μl/min sample in 25% MeCN+0.1% HCOOH+75% AcNH$_4$ (1 mg/ml). FIG. 3a shows the product of example 2a; FIG. 3b shows the product of example 2b; FIG. 3c shows HSA as obtained from Sigma for comparison.

EXAMPLE 3

Production of GBS-ADH-HSA

EXAMPLE 3a

Figure 4A:
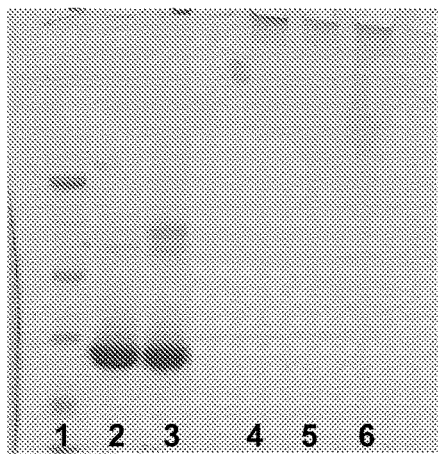
FIG. 4 shows SDS-PAGE analysis of purification of GBS-ADH-HSA conjugates by (a) HA column, and (b) Sepharyl S400 column.

GBS polysaccharide Ia, Ib or III (2 mg/ml), HSA-ADH in an amount such that the molar ratio of polysaccharide to ADH residues introduced on HSA was 2:1, and EDAC at a 1:1 molar ratio with polysaccharide were mixed in 100 mM MES buffer at pH 5.0 for 3 hours at room temperature. Purification was by dialysis with 6-8 kDa membrane against H$_2$O and then against NaPi 10 mM pH 7.0 at 4° C. with slow stirring. The conjugate was then loaded in an HA column, using as elution buffer NaPi 10 mM pH 7.2 and as gradient buffer NaPi 400 mM pH 7.2. The resultant conjugates were analysed by SDS-PAGE (FIG. 4a).

EXAMPLE 3b

Figure 4B:
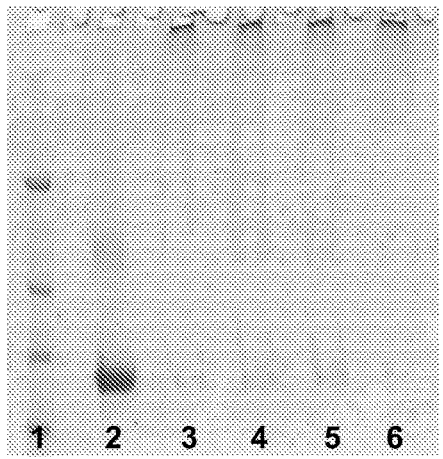

GBS polysaccharide Ib (5 mg/ml), HSA-ADH in an amount such that the molar ratio of polysaccharide to ADH residues introduced on HSA was (i) 1:0.2, (ii) 1:0.4, (iii) 1:0.8 or (iv) 1:1.6, EDAC at a 1:1 molar ratio with polysaccharide, and N-hydroxysulfosuccinimide at a 1:1 molar ratio with polysaccharide were mixed overnight in MES100 mM/NaCl 250 mM at pH 5.0 at room temperature. The reaction is quenched adding NaPi 400 mM pH 7.2 in order to neutralize pH reaction. Then the conjugate is loaded in 5400 column, using as elution buffer NaPi 10 mM/NaCl 250 mM pH 7.2. The resultant conjugates were analysed by SDS-PAGE (FIG. 4b).

EXAMPLE 4

Further Purification and Analysis of GBS-ADH-HSA

EXAMPLE 4a

Chromatography

Figure 5:
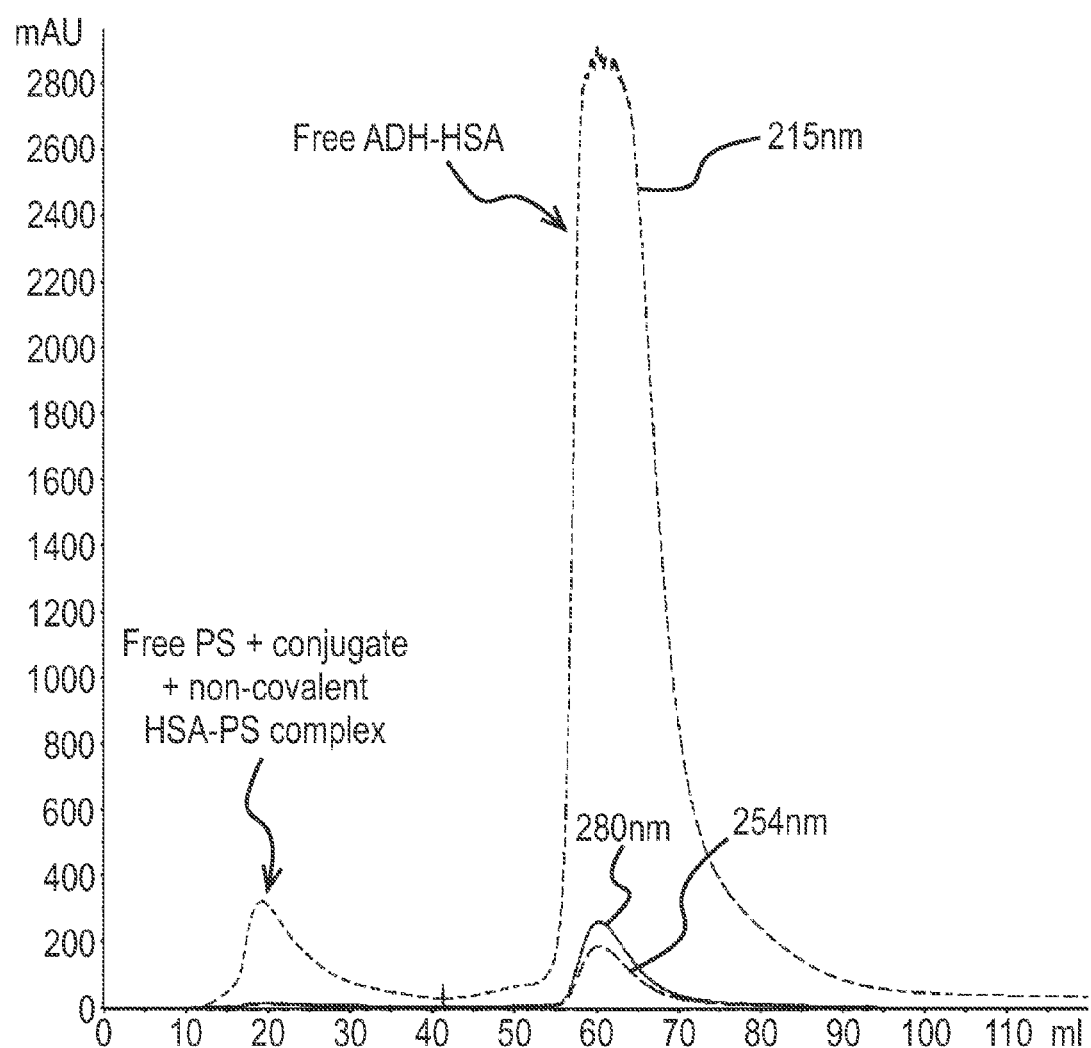
FIG. 5 shows purification of the GBS-ADH-HSA by HA column.
Figure 6:
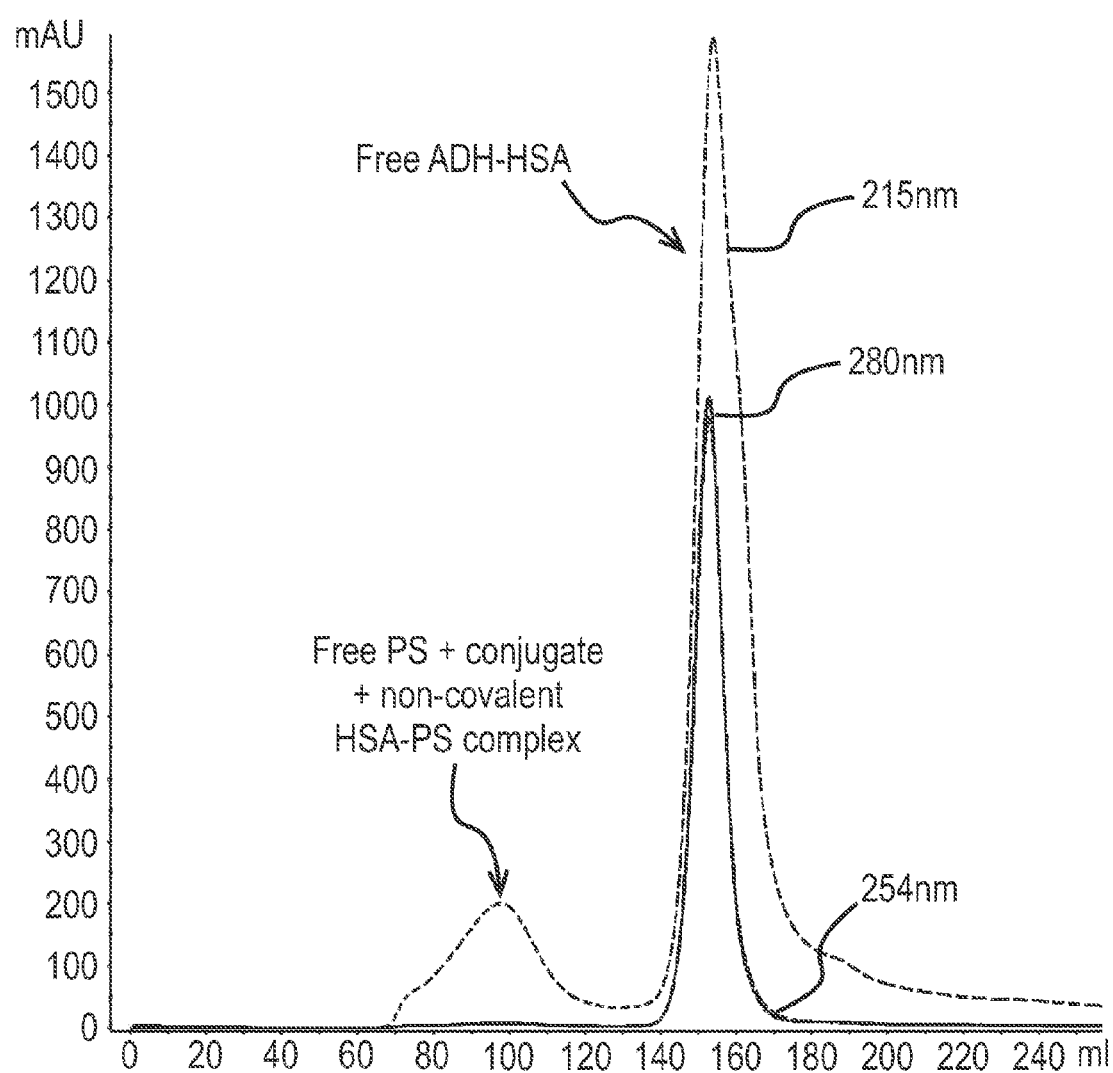
FIG. 6 shows purification of the GBS-ADH-HSA by Sephacryl S400 column.
Figure 7:
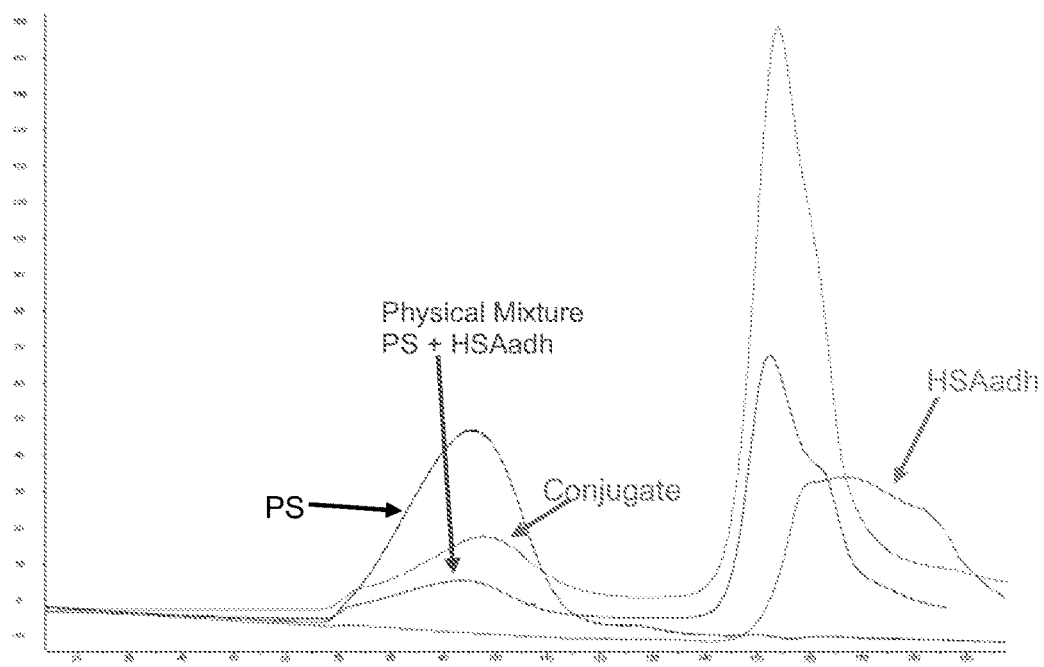
FIG. 7 shows purification of the GBS-ADH-HSA by Sephacryl S400 column.

Several methods were used to purify the GBS-ADH-HSA conjugates by chromatography: HA column 10 ml; elution buffer: NaPi 10 mM pH 7.2; gradient buffer: NaPi 400 mM pH 7.2) (FIG. 5); Sephacryl S400 column 170 ml; elution buffer: NaPi 10 mM/NaCl 250 mM pH 7.2 (FIG. 6); and Sephacryl S400 column 170 ml; elution buffer: NaPi 10 mM/NaCl 250 mM pH 7.2, 215 nm (FIG. 7).

The conjugate could not readily be separated from the mixture of the HSA-ADH and the polysaccharide. This suggests that there may be a non-covalent complex of the polysaccharide and HSA-ADH that runs at the same polarity as the conjugate.

EXAMPLE 4b

Western Blot Analysis

The products of Example 3b were analysed by Western blot (FIG. 8) using anti-GBS Ib CRM197. The blots indicate the presence of covalent conjugates.

EXAMPLE 5

The possibility of a non-covalent interaction in a physical mix of ADH-derivatized HSA and GBS saccharides was investigated further. GBS saccharide Ib (PSIb) and HSA-ADH were mixed in 1 ml NaPi 35 mM pH 7.2/Tween20 0.05%. 1 ml of $K_2HPO4$ (8.6M, saturated solution) was added. The mixture was cooled for 30 min in ice then subjected to centrifugation and the pellet separated. The pellet was dissolved in 1 ml NaPi 10 mM pH 7.2 and analysed.

The saccharide alone was shown not to precipitate when subjected to these conditions, whereas the protein alone does precipitate. The results are given in Table 2

TABLE 2

| Sample | Saccharide | Recovery | Protein (μg/mL) | Recovery (%) |
|---|---|---|---|---|
| Mix PSIb + HSA-ADH Starting | 822.1 | — | 7212.1 | — |
| Mix PSIb + HSA-ADH Pellet | 663.9 | 80.8 | 5215.7 | 72.3 |
| Mix PSIb + HSA-ADH Blank | 50.5<br>9.4 | 6.1<br>— | 237.4<br>— | 3.3<br>— |

EXAMPLE 6

The sensitivity of the two ELISA assays was compared using the same standard sera for the each methods. The optical density (OD) values for each ELISA assay, using the same increasing concentrations of serum are shown below.

| | OD average | |
|---|---|---|
| Standard serum (μg/ml IgG) | Covalently conjugated GBS Ib-ADH-HSA (saccharide 141.21 μg/ml; free saccharide 90.8%) | Physical Mixture PSIb + HSA-ADH (saccharide 153.81 μg/ml) |
| 0.0100 | 2.822 | 1.422 |
| 0.0050 | 1.341 | 0.690 |
| 0.0025 | 0.647 | 0.350 |
| 0.0013 | 0.299 | 0.299 |
| 0.0006 | 0.149 | 0.149 |

The data show that higher values are obtained for the covalently conjugated GBS Ib-HSA-ADH compared to the physical mixture of PSIb and HSA-ADH. Binding is evidenced between the two components of the physical mixture but the sensitivity is lower.

EXAMPLE 7

Characterization of GBS-HSA-ADH Samples

EXAMPLE 7a

Saccharide content was determined by colorimetric sialic acid assay. Protein content was determined by MicroBCA. Free saccharide content was determined by Capillary electrophoresis. The results are shown in Table 3 and Table 4.

TABLE 3 analysis of preparations according to Example 3a

| Sample | Saccharide (μg/ml) | Protein (μg/ml) | Free Saccharide (%) |
|---|---|---|---|
| GBS Ia HSA-ADH Lot A | 403 | 138 | 87.51 |
| GBS Ia-ADH-HSA Lot B | 159 | 40 | 66.23 |
| GBS Ia-ADH-HSA Lot C | 266 | 96 | 74.63 |
| GBS Ib-ADH-HSA Lot A | 346 | 67 | 54.9 |
| GBS Ib-ADH-HSA Lot B | 174 | 72 | 77.75 |
| GBS III-ADH-HSA LotA | 330 | 99 | 62.41 |
| GBS III-ADH-HSA Lot B | 208 | 127 | 74.84 |

TABLE 4 analysis of the preparation of example 3b

| Sample | Saccharide (μg/ml) | Protein (μg/ml) | Free Saccharide (%) |
|---|---|---|---|
| GBS Ib-ADH-HSA Lot A | 144.11 | 18.8 | 65.8 |
| GBS Ib-ADH-HSA Lot B | 166.15 | 22.5 | 84.4 |
| GBS Ib-ADH-HSA Lot C | 141.21 | 15.6 | 90.8 |
| GBS Ib-ADH-HSA Lot D | 144.11 | 18.8 | 65.8 |

EXAMPLE 7b

Capillary Electrophoresis

Figure 9A:
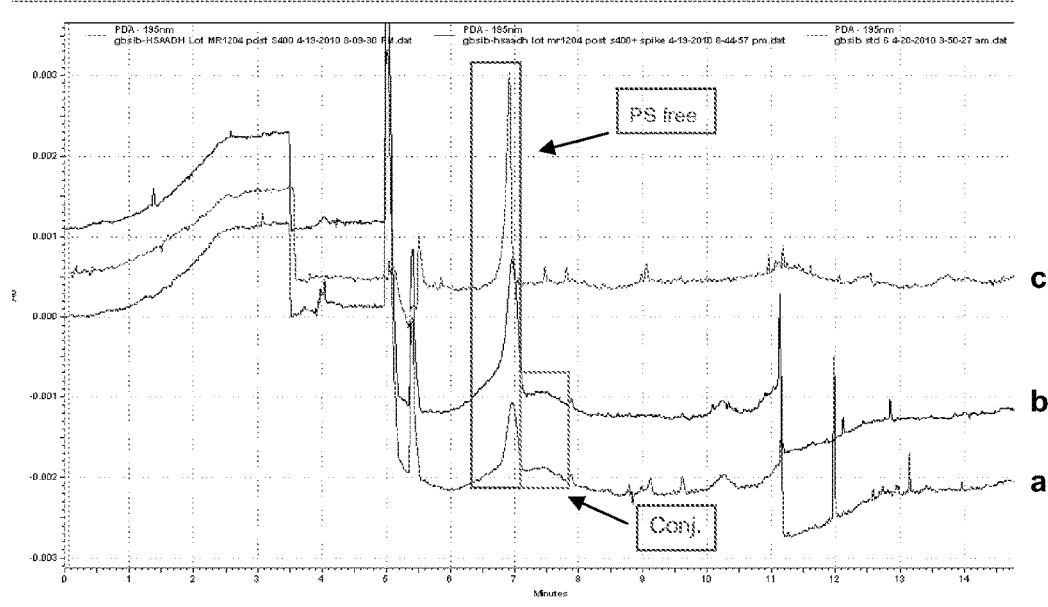
FIG. 9 shows capillary electrophoresis analysis of covalent conjugates of GBS Ib with HSA-ADH prepared in the following molar ratios: (a) 1:1; (b) 1:2; and (c) 1:4.
Figure 9B:
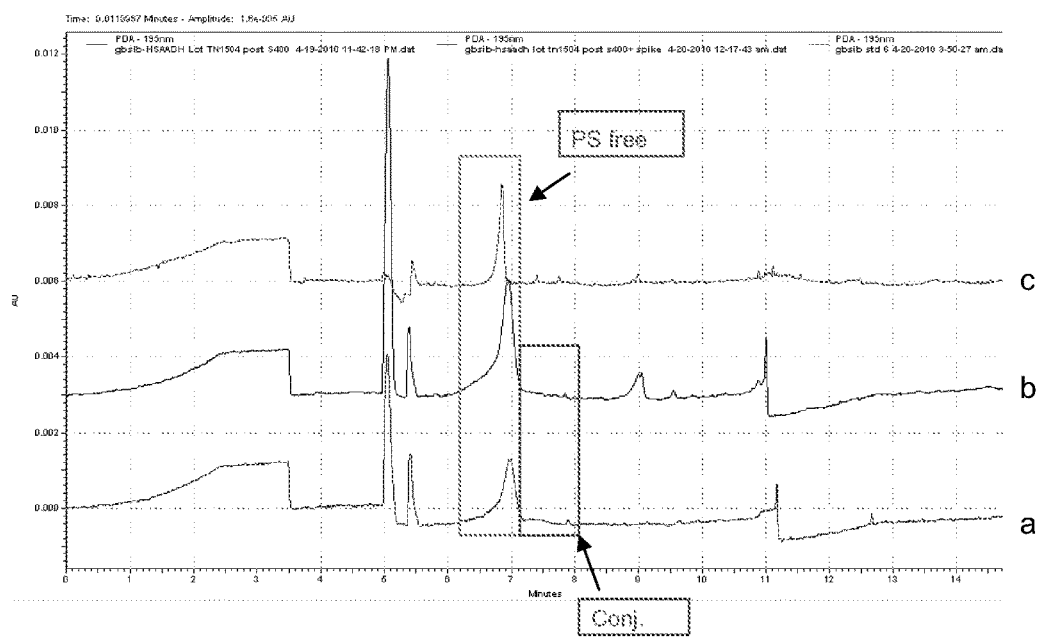
Figure 9C:
Figure 10C:
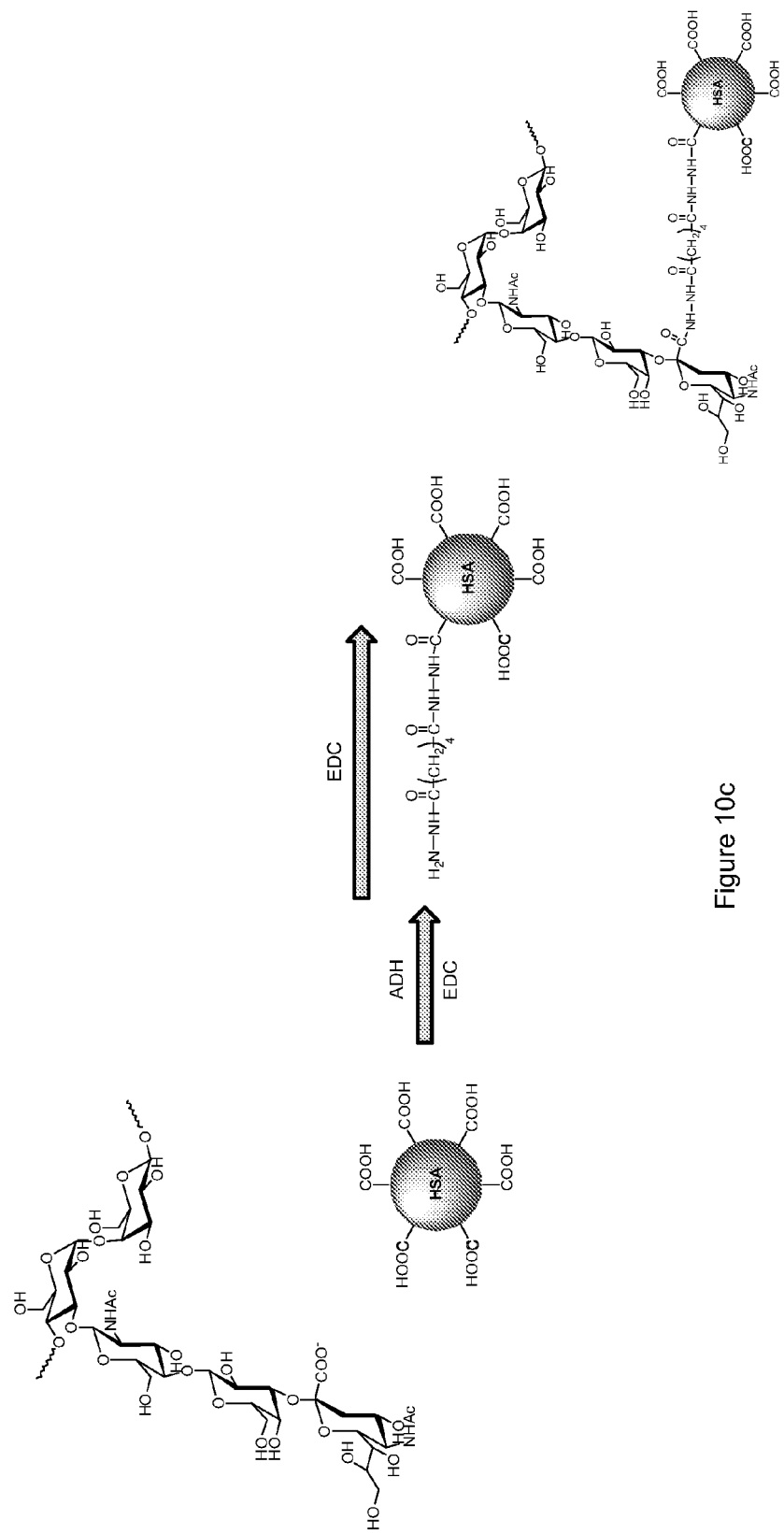
FIG. 10c shows in schematic the production of GBS Ia-ADH-HSA. ELISA coating reagent (free polysaccharide~60-90%).

GBS Ib-HSA-ADH conjugates were also analysed by capillary electrophoresis. Buffer $H_3BO3$ 100 mM; SDS pH 9.0, SDS 25 mM; Run time 15 min; Voltage 25 KVTemp. 20° C.; Capillary 50 mm, 50 cm. Conjugates in the following weight:weight ratios were analysed: GBS Ib:HSA-ADH 1:1 (FIG. 9a; percentage of free saccharide is 65.8%); GBS Ib:HSA-ADH 1:2 (FIG. 9b; percentage of free saccharide is 90.1%); and GBS Ib:HSA-ADH 1:4 (FIG. 9c; percentage of free saccharide is 81.0%).

EXAMPLE 8

Example of Assay Method

Coating of Multiwell Plates
  Ia: 100 μL of 1 μg/mL solution of HSA-ADH covalently conjugated polysaccharide in 1× Phosphate Buffered Saline (PBS) were dispensed in each well of the plate. The plate was incubated overnight at room temperature and then washed three times in washing buffer (0.05% Tween 20 in 1×PBS).
  Ib: 100 μL of 1 μg/mL solution of HSA-ADH covalently conjugated polysaccharide in 1×PBS were dispensed in each well of the plate. The plate was incubated overnight at room temperature and then washed three times in washing buffer.
  III: 100 μl of 1 μg/mL solution of HSA-ADH covalently conjugated polysaccharide in 1×PBS were dispensed in each well of the plate. The plate was incubated overnight at room temperature and then washed three times in washing buffer.
Post-Coating
  250 μL of post-coating solution (2% BSA, 0.05% Tween 20 in PBS) were dispensed in each well of the plate. The plate was incubated 90 min at 37° C. and then aspirated to remove the post-coating solution.

Serum Incubation

Mouse sera were diluted in dilution buffer (2% BSA, 0.05% Tween 20 in PBS). Standard serum (a pool of hyper-immune sera was prepared by pooling appropriate serum sample) was diluted in order to obtain an OD above 2.000 at 405 nm (for the starting dilution). The plate was incubated one hour at 37° C. and then washed three times in washing buffer (0.05% Tween 20 in 1×PBS).

Alkaline Phosphatase (AP)-Conjugated Antibody Incubation

100 μL of a solution of AP-conjugated anti-species in dilution buffer (2% BSA, 0.05% Tween 20 in PBS) were dispensed in each well of the plate. The plate was incubated 90 minutes at 37° C. and then washed three times in washing buffer (0.05% Tween 20 in 1×PBS).

Cromogenic Reaction and Calculation of Antibody Titres

100 μl of a chromogenic (p-nitrophenylphosphate) solution were added in each well. After an incubation of 25-30 minutes at room temperature, 100 μl of an EDTA solution 7.0% pH 8.0 were added to each well to stop the enzymatic reaction. The developed colour was measured using a plate reader with wavelength set at 405 nm. Total IgG titres against GBS polysaccharide antigens (Ia, Ib and III) were calculated by using the Reference Line Assay Method and results were expressed as arbitrary ELISA units/ml (EU/ml). For each of the three antigens, the standard serum IgG titre was arbitrarily assigned a value of 1.0 EU/ml. Serum titres were estimated by interpolating ODs with the titration curve (bias and slope) of the standard pool. Whenever the concentration of specific IgG of the standard serum was known, the results were expressed as μg/ml of specific IgG.

The ADH-HSA ELISA was compared with the classical HSA ELISA by a) measuring IgG responses in sera from animals immunized with $CRM_{197}$-conjugated GBS Ia, Ib and III polysaccharides and b) measuring inhibition of those IgG responses by pre-incubation with the native polysaccharide. The inhibition by native polysaccharide is shown in FIGS. 11a, 11b (GBS Ia), 11c (GBS Ib) and 11d (GBSIII) as a percentage of the response obtained in the absence of inhibitor.

Three pools of sera with high, medium and low concentrations of antibody were tested. The sera were incubated for 30 minutes at 37° C. with increasing concentrations of polysaccharide: 0.5 μg/ml; 1.0 μg/ml; 2.0 μg/ml and 4.0 μg/ml.

Immunoglobulin responses measured both for Ia and III were lower using plates coated in the saccharide covalently linked to ADH-HSA than those coated in the saccharide covalently linked to HSA, suggesting that the classical HSA method detects additional epitopes that are possibly present in the $CRM_{197}$ conjugates and not in the native polysaccharide.

The antibodies that are found to bind in the method of the present invention can be completely inhibited by pre-incubation with native Ia, Ib or III polysaccharide whereas the antibodies detected in the method of the prior art (using a mixture of HSA and saccharide) can only be partially inhibited. This suggests that the method of the prior art is indeed detecting antibodies not specific to the native saccharide, whereas the method of the present invention is not.

Inhibition of immunoglobulin responses with the native polysaccharide was higher using ADH-HSA compared with classical HSA. This was demonstrated with multiple sera and again indicates that the classical HSA method detects additional epitopes that may be present in the CRM197 conjugates and not in the native polysaccharide. This is particularly clear for Ia (observed with all 3 sera, particularly the "medium", which attains 100% with ADH and remains 50% with HSA). Better inhibition by free saccharide in the ADH plate in the case of Ib also. For III, the difference between ADH and HSA can be seen with the "low" serum, while 100% inhibition is quickly reached for the other sera. The procedure for III may therefore be optimized further. More generally it seems that there is a tendency for ADH to bind a smaller amount of antibodies for the III antigen than for Ia antigen, suggesting it is more selective and specific.

EXAMPLE 9

Further Comparison with the Method of the Prior Art

Figure 12:
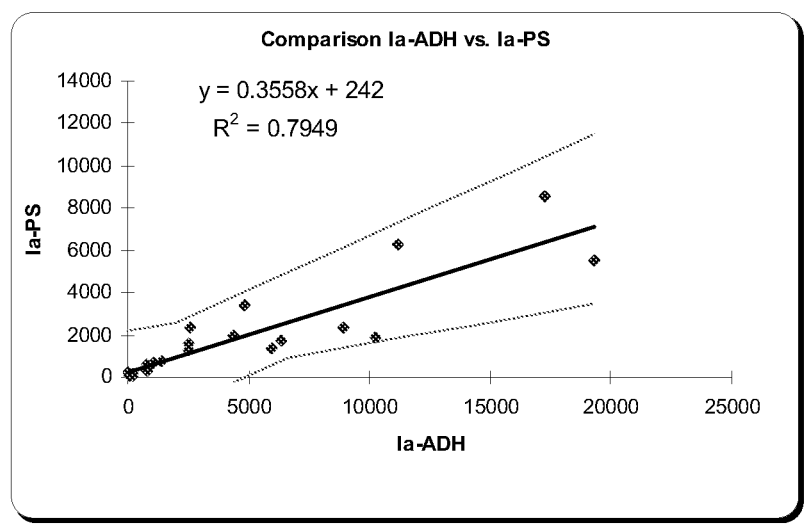
FIG. 12 shows comparison between the performances of ELISA assays using free GBS saccharide Ia for coating and those using Ia conjugated to ADH.

A method of the invention was compared with that of the prior art based on free capsular polysaccharide. The method of the invention allowed use of a lower concentration of polysaccharide and reduced incubation time with clearly better results in terms of precision, accuracy, linearity and coating stability for each GBS polysaccharide (Table 5). As shown in FIG. 12, the comparison study shows an acceptable agreement between the two different approaches as all data falls within the confidence limits p<0.05 (outer lines); therefore, the method with free polysaccharide can be substituted with that of the invention.

TABLE 5

Parameters of the ELISA method developed using saccharide-ADH-HSA conjugate for coating.

|  | Ia | Ib | III | V | Range of Acceptability |
|---|---|---|---|---|---|
| Repeatability | 3.4 | 4.7 | 5.7 | 4.6 | <15% |
| Reproducibility | 3.6 | 4.5 | 4.4 | 5.1 | <20% |
| Accuracy | 91 | 99 | 104 | 103 | 80-120% |
| Linearity | 0.9966 | 0.9972 | 0.9924 | 0.9982 | $R^2 > 0.9$ |
| Plate stability | 12 | 12 | 12 | 12 | days |

EXAMPLE 10

Linearity Assays

Figure 13A:
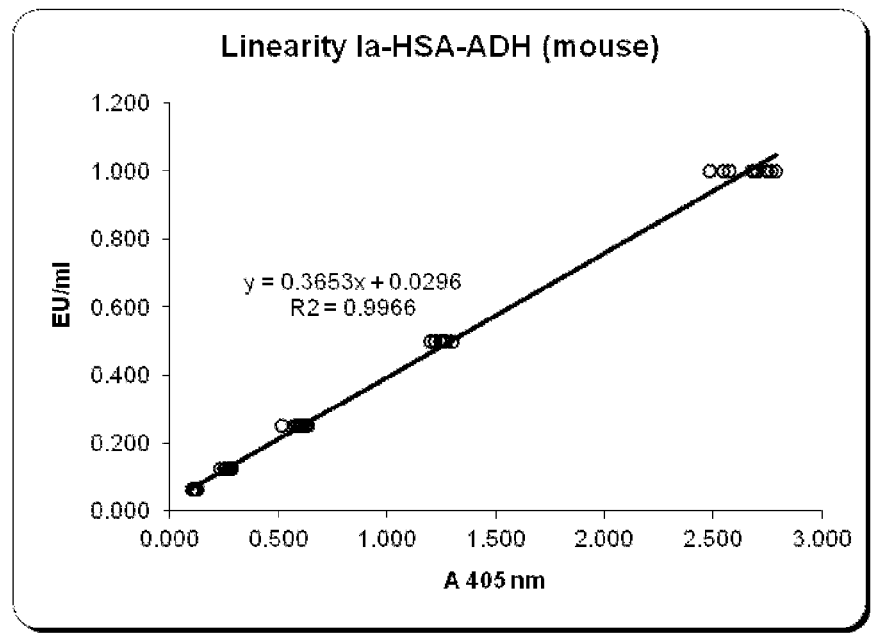
FIG. 13 shows the reproducibility and the linearity of the assay of the present invention for GBS Ia, Ib and III polysaccharides, investigated using mouse and human sera. As shown the assay is highly reproducible and shows good linearity for all three polysaccharides.
Figure 13B:
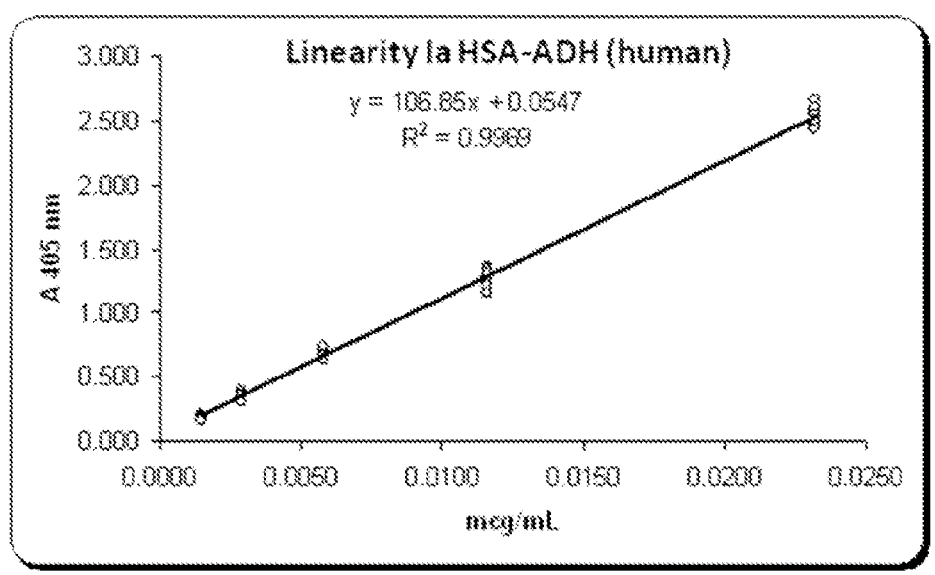
Figure 13C:
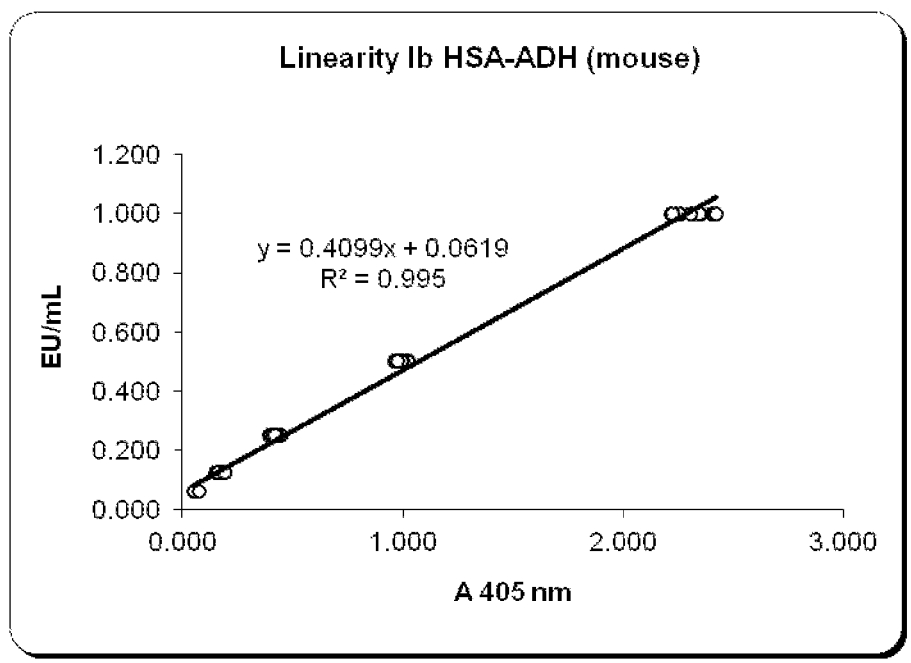
Figure 13D:
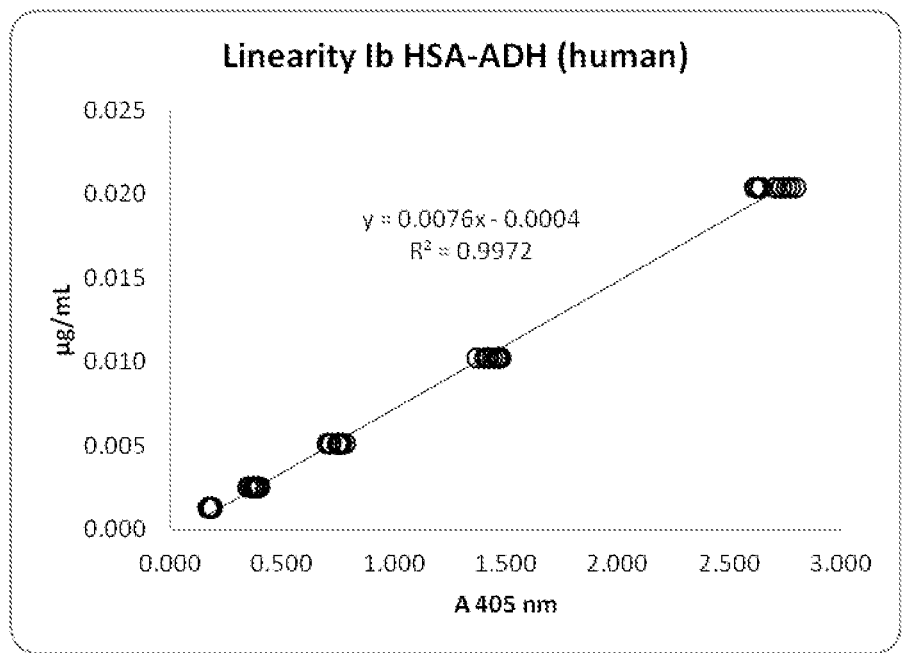
Figure 13E:
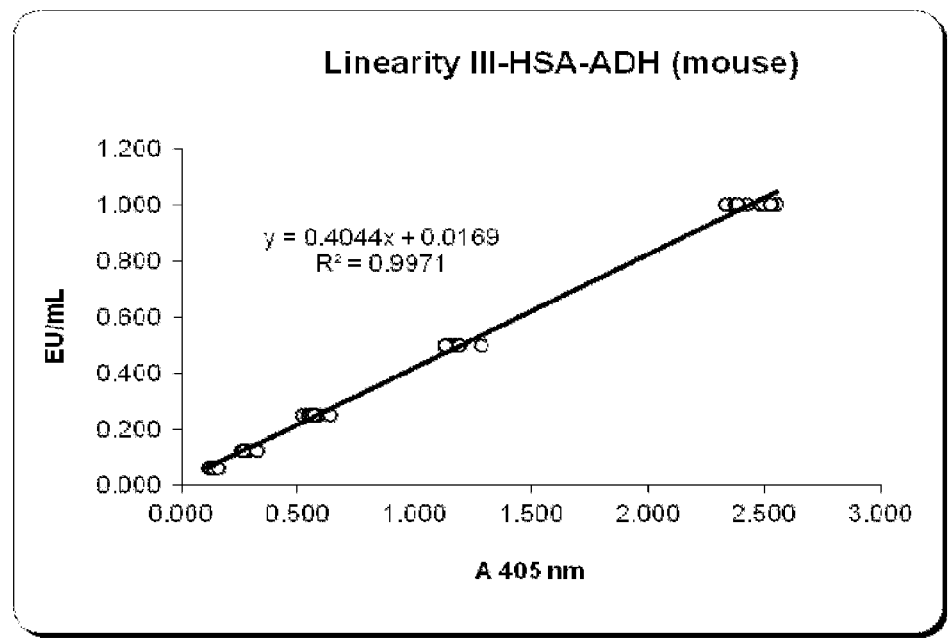
Figure 13F:
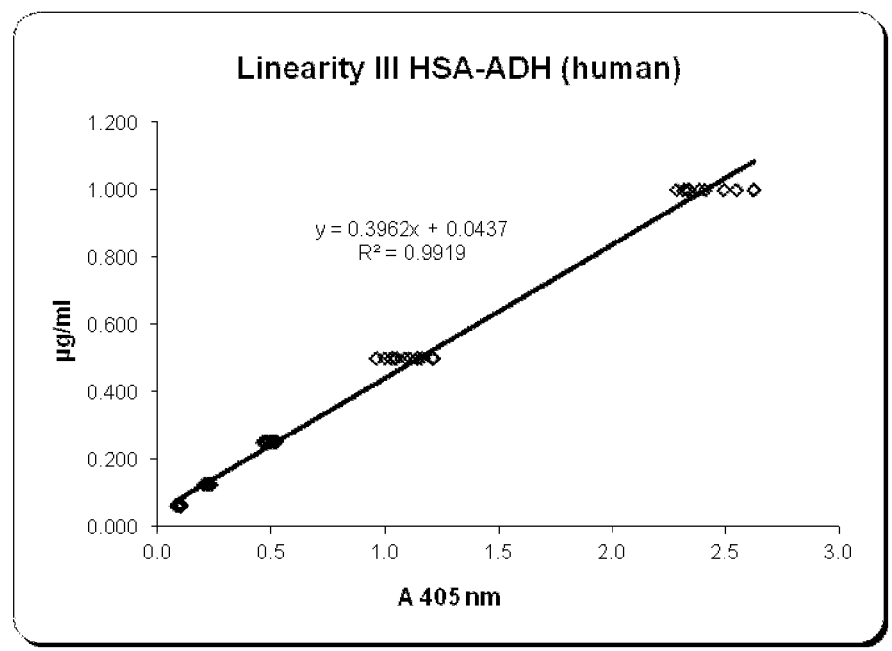
Figure 13G:
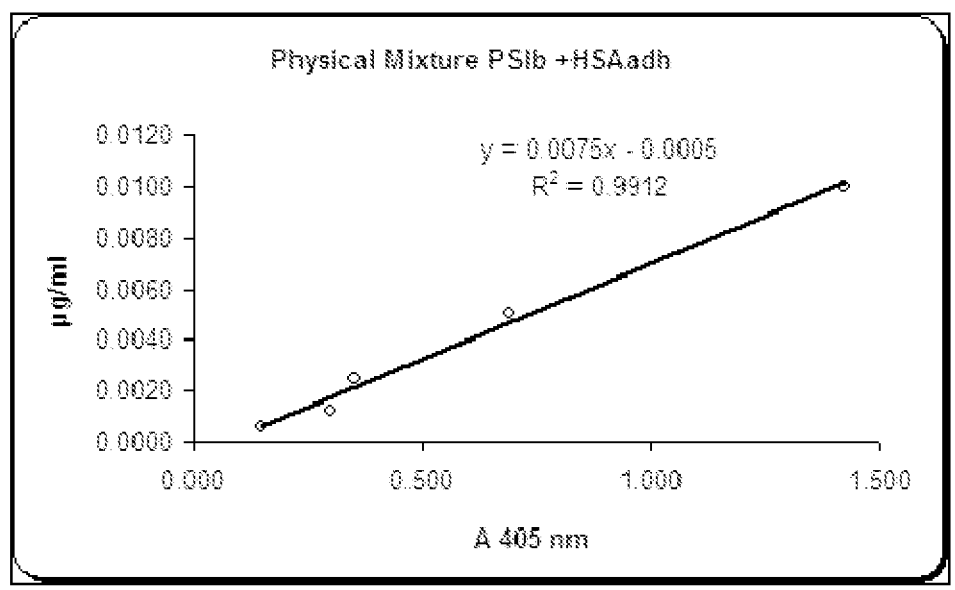

Linearity evaluation was performed with 11 replicates of the standard curve for GBS Ia-ADH-HSA (mouse, FIG. 13a; human, FIG. 13b), GBS Ib-ADH-HSA (mouse, FIG. 13c; human, FIG. 13d), GBS Ia-ADH-HSA (mouse, FIG. 13e; human, FIG. 13f) and for the physical mixture of GBS Ib with ADH-derivatized HSA.

EXAMPLE 11

Potency Assay

Figure 14:
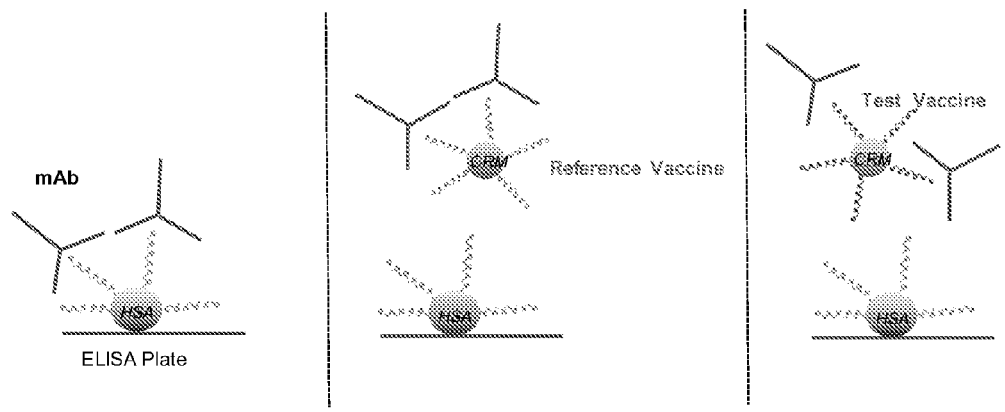
FIG. 14 illustrates the concept of the third aspect of the present invention.

An example of the third aspect of the invention is a method to evaluate the potency of a GBS capsular saccharide conjugate vaccine. An example of this method is outlined in FIG. 14. Briefly, the method compares the results of two competition ELISAs, in which (a) a reference GBS capsular saccharide conjugate vaccine of known potency and (b) a batch of the GBS capsular saccharide conjugate vaccine of unknown potency separately compete with a conjugate of the saccharide associated with ADH-HSA for binding to a monoclonal antibody to the saccharide. It is envisaged that the method may be carried out in the following way.

Microtitre plates are coated, at a known final concentration in PBS pH 7.4, with a covalent conjugate of ADH-HSA and the saccharide that is comprised in the vaccine to be tested. Plates are sealed, incubated overnight at 2°-8° C., then washed and saturated with a PBS pH 7.4 solution containing 1% porcine gelatin, as a blocking reagent, for a two-hour incubation at 37° C. Then plates are fixed with a saline solution, containing 4% polyvinyl-pyrrolidone and 10% sucrose, and incubated at room temperature for two hours. After incubating, the fixing solution is aspired and plates are left to dry overnight on the bench.

In a different polypropylene microtitre plate the specific competitors (for example, a reference vaccine tested in human clinical trials and a portion of a test vaccine batch) are diluted appropriately with buffer solution (1% bovine serum albumin in PBS pH 7.4 with 0.01% TWEEN 20 (TM)). The same volume of a monoclonal antibody to the saccharide, at a fixed dilution, is then added to the wells and allowed to interact directly with the competitor at room temperature. After this step the mixture is transferred to the coated and saturated plates and incubated for two hours at 37° C. Plates are then washed and a goat-anti-mouse IgG antibody conjugated to alkaline phosphatase is added. The secondary antibody is incubated for 1.5 hours at 37 C and, after washing, plates are left for 30 min at room temperature with a chromogenic substrate solution. Plates are blocked with a NaOH solution and then absorbance values are read at a wavelength of 405-620 nm.

Figure 15:
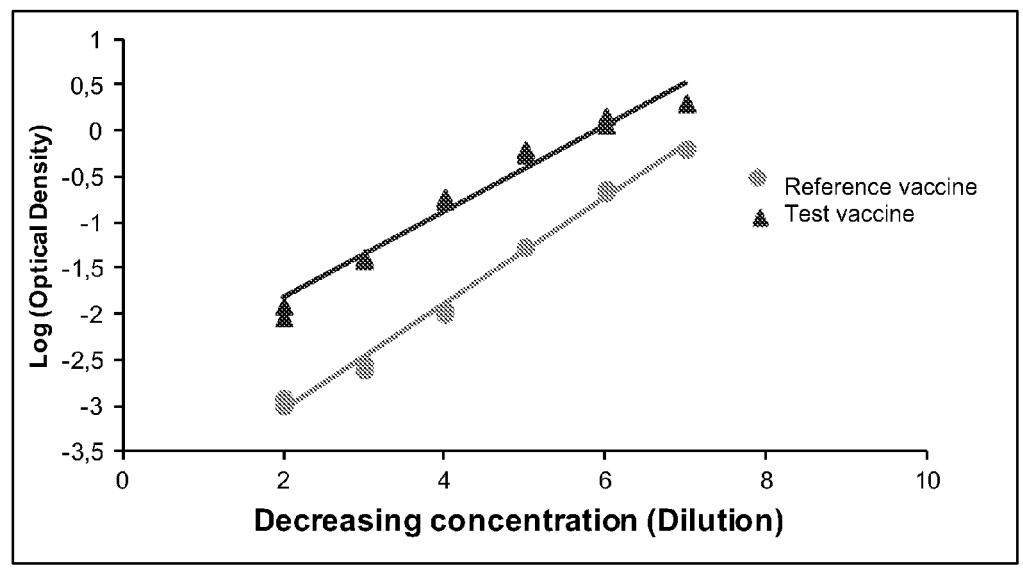
FIG. 15 shows an inhibition curve of monoclonal antibody binding to the test vaccine and the reference vaccine in the third aspect of the present invention.

The response curve of the vaccine batch is determined by a relative potency evaluation with respect to the reference vaccine, using the Parallel-Line Model, as described in the European Pharmacopoeia 6.0. According to this model, the relationship between the logarithmic transformation of the dose and the response (OD or a transformation) can be represented as a straight line over the range of doses used; the model is based on the parallelism assumption between the unknown and the reference vaccine. The horizontal distance between the two lines indicates the potency and immunogenicity of the unknown batch relative to the reference batch. An example of a plot used to assess this value (produced by a protocol similar to that outlined in this example) is shown in FIG. 15.

EXAMPLE 12

Generation of Antibodies

Mouse monoclonal antibodies (mAbs) were generated following standard procedures. B-cell hybridoma clones were isolated from spleen cells of immunized mice with the specific glyco-conjugate. Positive clones were first selected by ELISA and then culture supernatants were screened for binding to the surface of GBS strains, expressing the homologous capsular polysaccharide, by flow cytometry and by OPA assay in order to select bactericidal antibodies. Positive primary hybridoma clones were then subjected to single cell cloning and sub-cloning by limiting dilution. The sequences of the antibodies and the nucleic acids encoding them were determined by standard methods. The CDRs were predicted using the program described in ref. [133]. The SEQ ID NO for each sequence is set out in Table 6, and refers to the accompanying sequence listing.

TABLE 6

| GBS serotype specificity | Chain | Amino acid sequence comprising variable region | Nucleotide sequence | CDR1 | CDR2 | CDR3 |
|---|---|---|---|---|---|---|
| III | Light | 2 | 1 | 31 | 32 | 33 |
|  | Heavy | 4 | 3 | 22 | 23 | 24 |
| Ib | Light | 6 | 5 | 25 | 26 | 27 |
|  | Heavy | 8 | 7 | 28 | 29 | 30 |
| Ia | Light | 10 | 9 | 19 | 20 | 21 |
|  | Heavy | 12 | 11 | 34 | 35 | 36 |

EXAMPLE 13

Characterization of Antibodies

EXAMPLE 13a

The affinity of the antibodies for the relevant antigen was measured by surface plasmon resonance (SPR) using a Biacore X100 instrument (GE Healthcare).

GBS capsular polysaccharide Ia-HSA (10 µg/ml), GBS capsular polysaccharide Ib-HSA (2 µg/ml) and GBS capsular polysaccharide III-HSA (2 µg/ml), in 10 mM sodium acetate pH 4.5, were immobilized on CM5 biosensor chips (GE Healthcare). Optimum pH for immobilization of each glycoconjugate in the range of pH 4-5 was determined by a preliminary pH scouting test. Immobilization was carried out for 9 min at a flow rate of 10 µl/min in flow cell 2, using standard primary amine coupling (Amine Coupling Kit, GE Healthcare) in which the carboxymethylated CM5 dextran layers were activated at 10 µL/min for 7 min, by mixing equal volumes of 0.4 M N-ethyl-N'-(3-dimethylaminopropyl)carbodiimide (EDC) and 0.1 M N-hydroxysuccinimide (NHS). Unreacted NHS-ester groups were blocked with three injections (4 min each) of 1.0 M ethanolamine hydrochloride, at pH 8.5. The immobilization procedure allowed obtaining CM5-HSA-PSIa, CM5-HSA-PSIb and CM5-HSA-PSIII biosensors of ~2300 RU, ~550 RU and ~1100 RU, respectively. Untreated flow cell 1 was used as reference. HBS-EP with 0.005% (v/v) Tween 20 pH 7.2-7.4 was used as running buffer for conjugate immobilization.

The three mAbs of Example 12 were investigated for their binding capacity to GBS capsular polysaccharide Ia, Ib and III, respectively, in SPR kinetic experiments. Interaction parameters in terms of association ($k_a$) and dissociation ($k_d$) rate constants, and binding affinity ($K_D = k_d/k_a$) were determined.

Five two-fold serial dilutions of mAbs in running buffer (starting from 20 nM for the GBS capsular polysaccharide Ia and Ib specific mAbs and 50 nM for GBS capsular polysaccharide III specific mAb) were injected over the respective coated biosensor for 2 min at 45 µL/min followed by 10 min dissociation time. Biosensor regeneration was performed after each concentration cycle using 3.5 M $MgCl_2$ (2 min, 10 µl/min). This treatment did not damage the biosensor surface as shown by equivalent signals of binding ligand in different runs. Each kinetic experiment was performed in triplicate and preceded by an identical binding-regeneration cycle of buffer as analyte. This cycle was used as blank and subtracted from all the active curves to correct background effects.

The association, dissociation and affinity constants were determined by a simultaneous fitting of the kinetic curves with a model of equimolar stoichiometry (1:1) using the BIAevaluation X100 software version 1.0 (GE Healthcare). Kinetic constants were determined as the average results of three independent kinetic experiments. For the GBS capsular polysaccharide Ia and Ib specific mAbs, HBS-EP with 0.005% (v/v) Tween 20 pH 7.2 was used as running buffer for the kinetic experiments, while for the GBS capsular polysaccharide III specific mAb PBS buffer pH 7.2 with 0.005% (v/v) Tween 20 was used.

The results (average of three experiments) are shown in Table 7. The tested antibodies all showed high affinity.

TABLE 7

| Polysaccharide | α-Ia (23H6D2) | α-Ib (30G1B5) | α-III (27C6C10) |
|---|---|---|---|
| $K_D$ (M) | $5.8 \pm 1.5 \times 10^{-10}$ | $9.2 \pm 3.7 \times 10^{-11}$ | $2.0 \pm 1.3 \times 10^{-9}$ |

EXAMPLE 13b

The functional activity of these antibodies was measured by GBS killing in an OPA assay. Briefly, GBS samples were incubated with prediluted sera from immunized mice (heated at 56° C. for 30 minutes prior to testing to inactivate endogenous complement activity), differentiated HL-60 cells in DMF (0.8%) and complement (C3b) for 1 hour with shaking. The mixtures were sampled, diluted and plated at T0 (after mixing) and at T60 (after shaking). Plates were stored overnight, then the number of colony-forming units for each dilution was quantified. Based on these data, the OPA titre (antibody dilution mediating 50% of killing) was determined.

The results are shown in Table 8. The tested antibodies all showed high functional activity.

TABLE 8

| Polysaccharide | α-Ia (23H6D2) | α-Ib (30G1B5) | α-III (27C6C10) |
|---|---|---|---|
| OPA titre | 519 | 960 | 516 |

EXAMPLE 13c

The specificity of the antibodies for a conjugate of GBS polysaccharide and $CRM_{197}$ over the corresponding HSA conjugate was assessed by ELISA competition assays as described in Example 11. All 3 antibodies were IgG1. The concentrations were as follows: α-Ia, 0.20 μg/ml; α-Ib, 0.16 μg/ml; α-III, 0.56 μg/ml.

Figure 16:
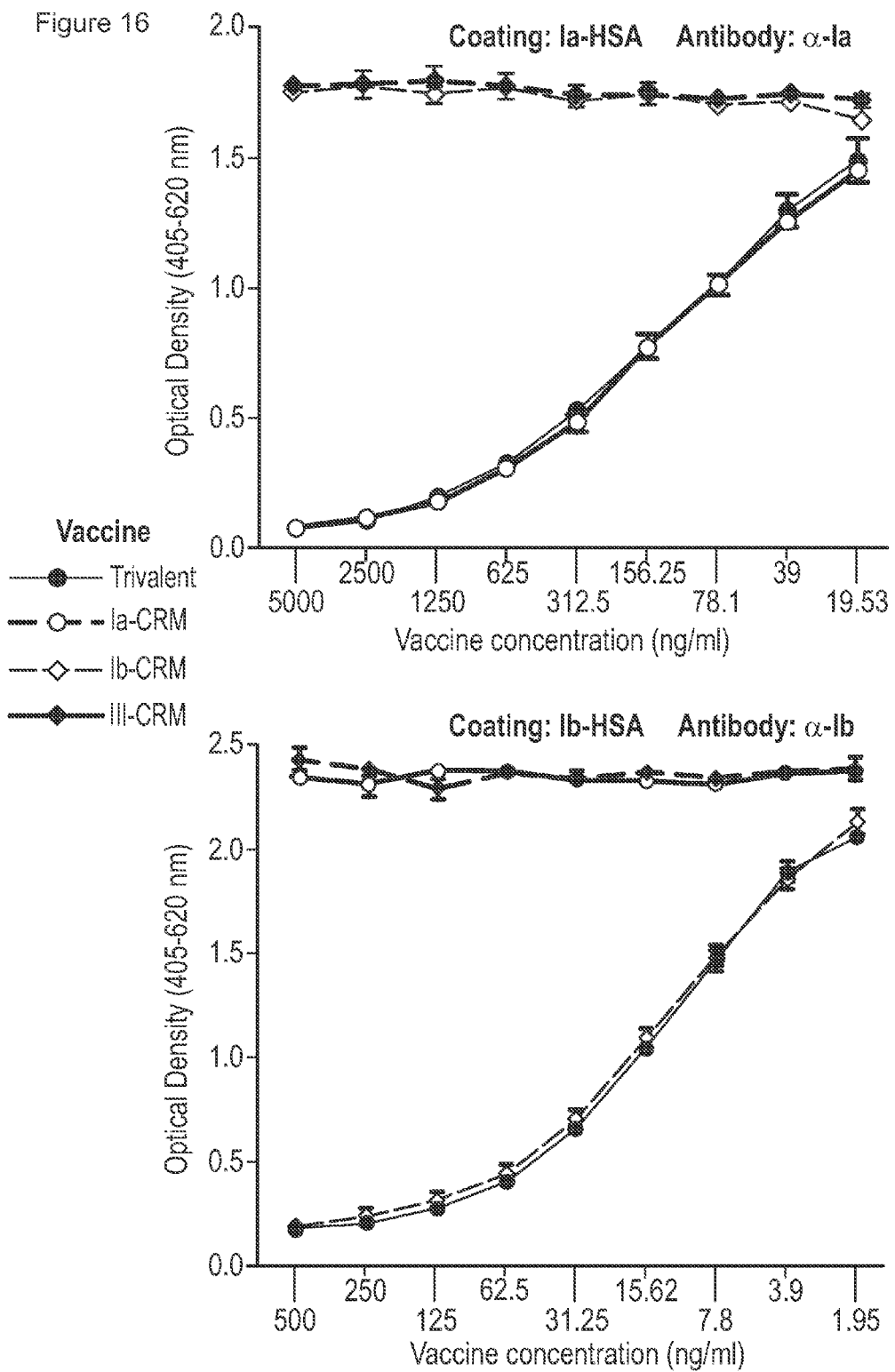
FIG. 16 shows binding of antibodies of the present invention to polysaccharide-HSA conjugates in the presence of conjugates of $CRM_{197}$ to different GBS polysaccharides.

Each $CRM_{197}$ conjugate inhibited binding of its specific antibody to the corresponding HSA conjugate in a dose dependent, reproducible manner. A trivalent vaccine comprising $CRM_{197}$ conjugates of GBS polysaccharides from each serotype also inhibited binding in a dose dependent, reproducible manner. Binding was not inhibited by $CRM_{197}$ conjugates of other serotypes. The results are shown in FIG. 16.

EXAMPLE 13d

Figure 17:
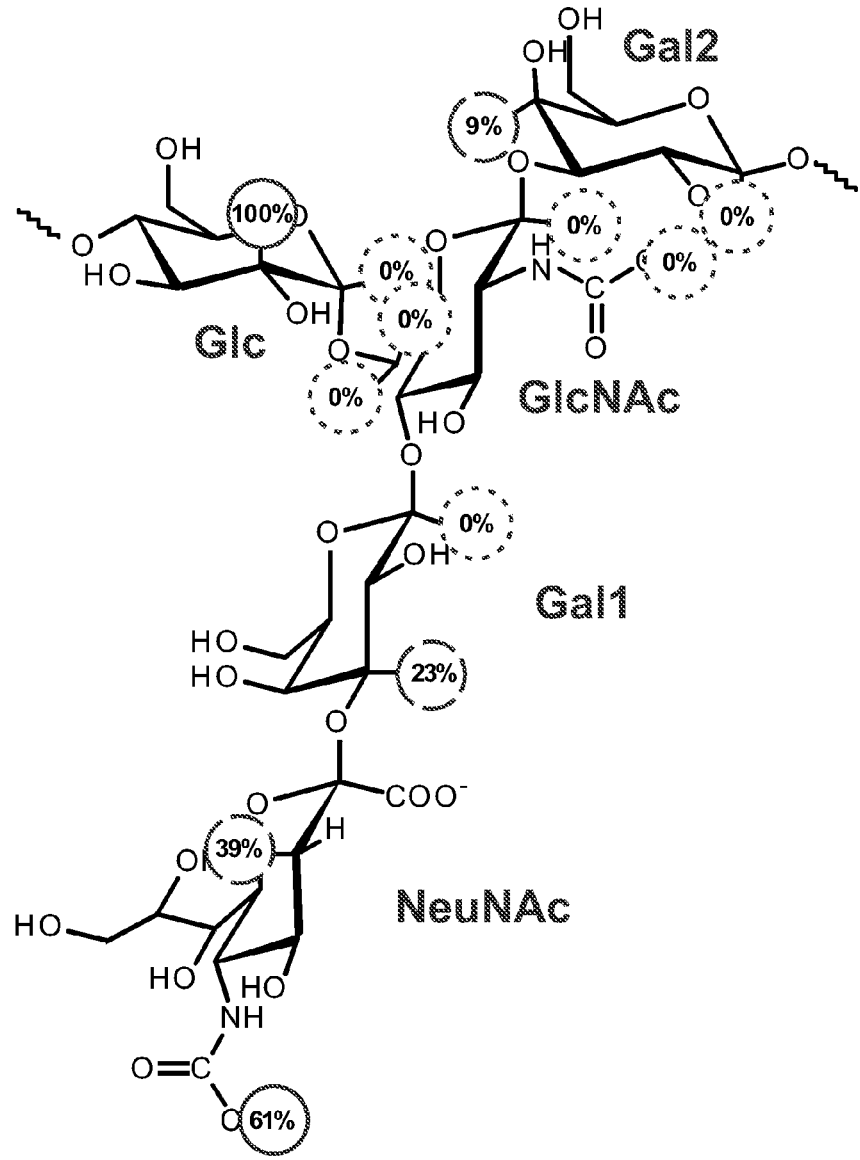
FIG. 17 maps binding of antibodies of the present invention to GBS polysaccharides.

Epitope mapping was carried out by saturation transfer difference NMR using antibodies according to the invention. It was demonstrated that NeuNAc residues, in addition to other residues constituting the repeating units, are involved in the antibody binding for all the GBS polysaccharides. Results are shown in FIG. 17.

EXAMPLE 14

Discrimination of Sub-Potent Vaccine Batches

Figure 18:
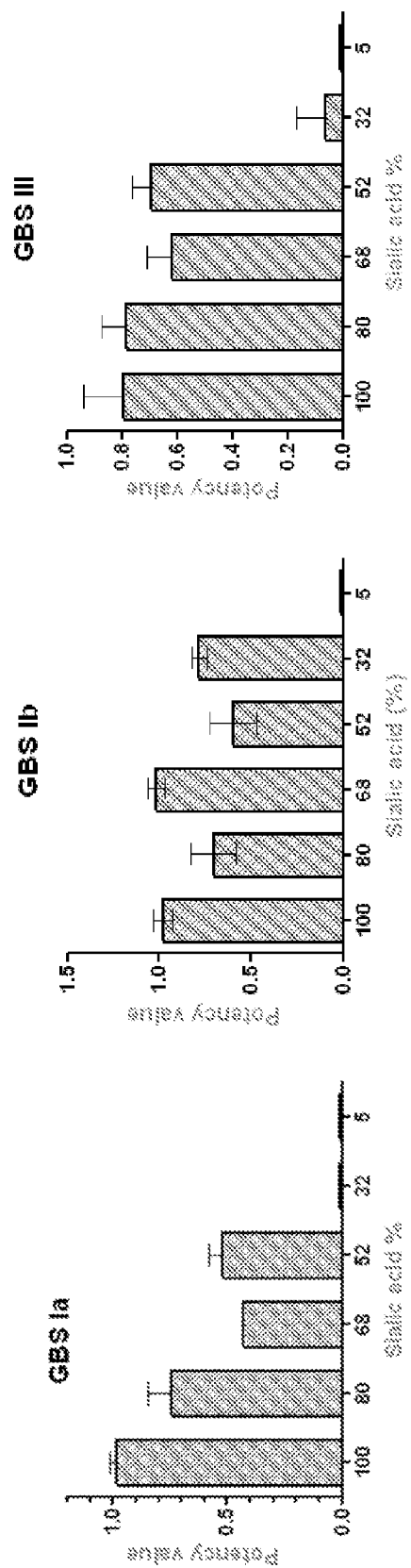
FIG. 18 shows results of assays according to the third aspect of the invention using polysaccharide batches with decreasing sialic acid content.

Batches of GBS Ia, Ib and III polysaccharide conjugates were prepared with sialic acid content decreasing from 100 to <5% (50 mM NaAc, pH 4.75, 80° C.; filtration with 30 kDa MWCO, 10 mM NaPi pH 7.2; dialysis). Sialic acid content was determined by NMR. Representative results of assays according to Example 11 using these batches are shown in FIG. 18. These indicate that sialic acid concentrations lower than 32% (GBS Ia and III) and 5% (GBS Ib) result in absence of potency according to this assay. OPA titres and survival after lethal challenge in mice decrease when sialic acid concentrations are below 24%, whereas ELISA titres are higher at lower sialic acid concentration.

EXAMPLE 15

Characterization of Assay According to Example 11

EXAMPLE 15a

Figure 19:
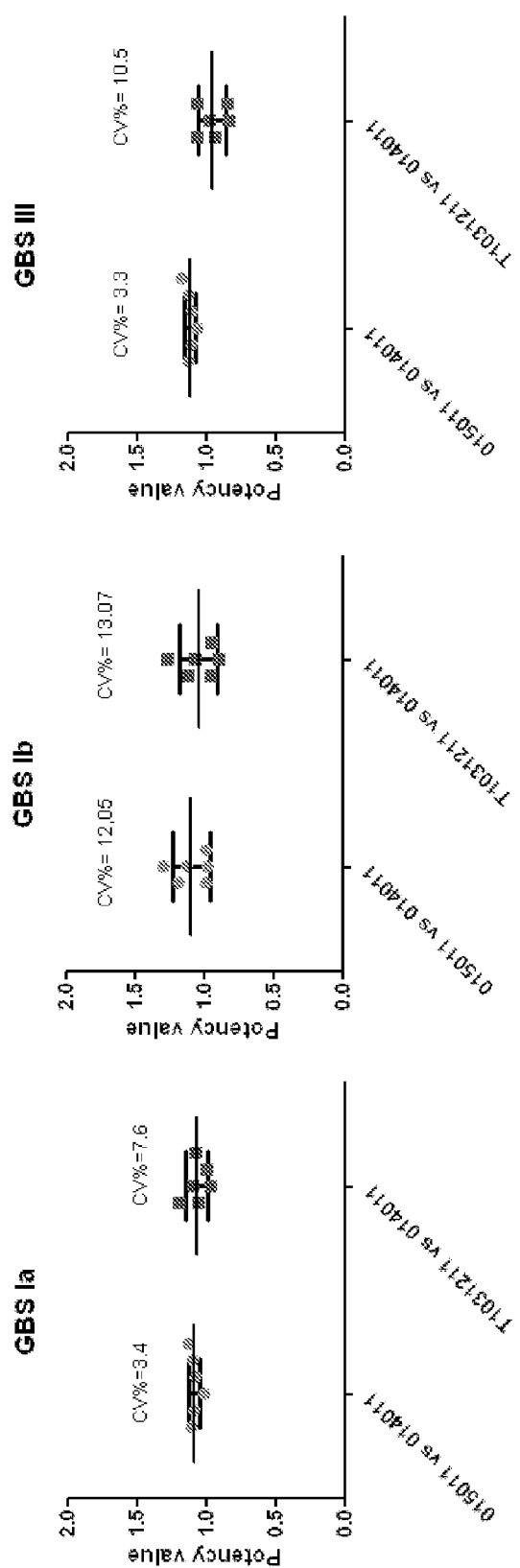
FIG. 19 shows reproducibility of an assay according to the third aspect of the invention, as tested by determining potency values for two vaccine batches.

Assay reproducibility was tested by determining potency values for two vaccine batches. The results are shown in FIG. 19. The assay shows CV % of potency values of lower than 15% for two different vaccine batches in the case of GBS Ia, Ib and III.

EXAMPLE 15b

Figure 20:
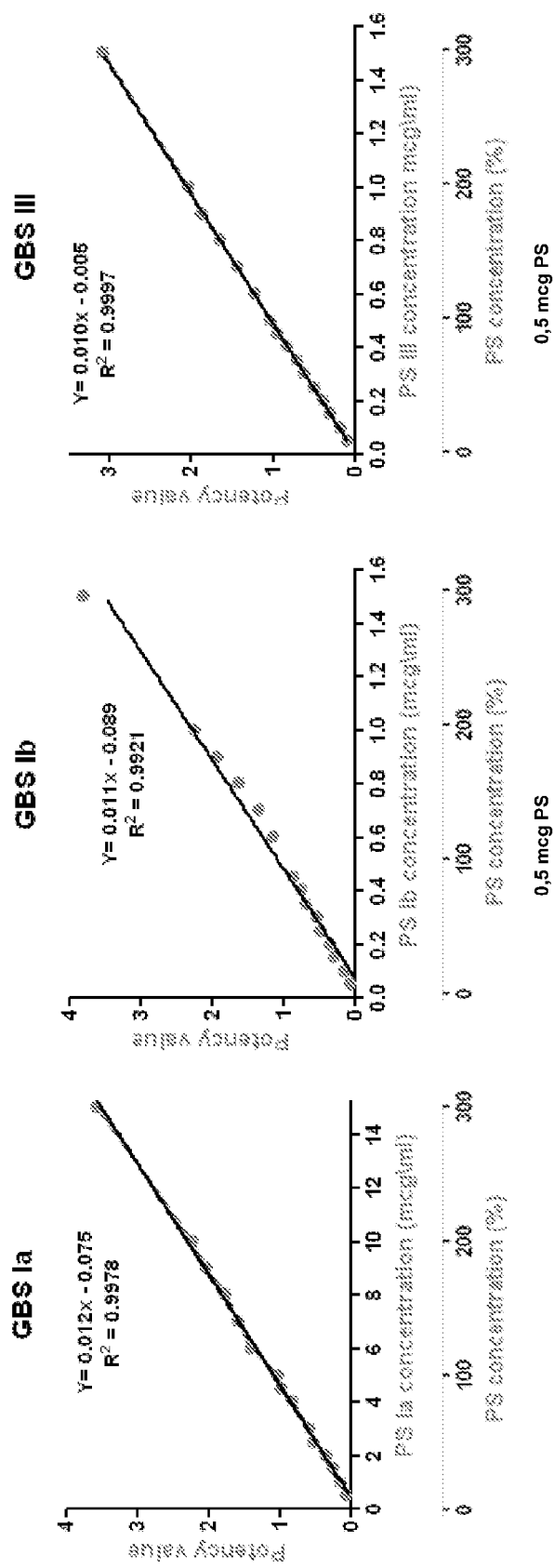
FIG. 20 shows results of assaying increasing concentrations of GBS trivalent vaccine.

The assay was used to determine the relative potency values of increasing concentrations of GBS trivalent vaccine. The results showed linearity over a high dynamic range (analysed for concentrations from 0.25 to 1.6 μg/ml of each of GBS Ia, Ib and III) as shown in FIG. 20. The assay therefore allows determination of the precise amount of each single antigen component in the trivalent vaccine.

EXAMPLE 15c

Figure 21:
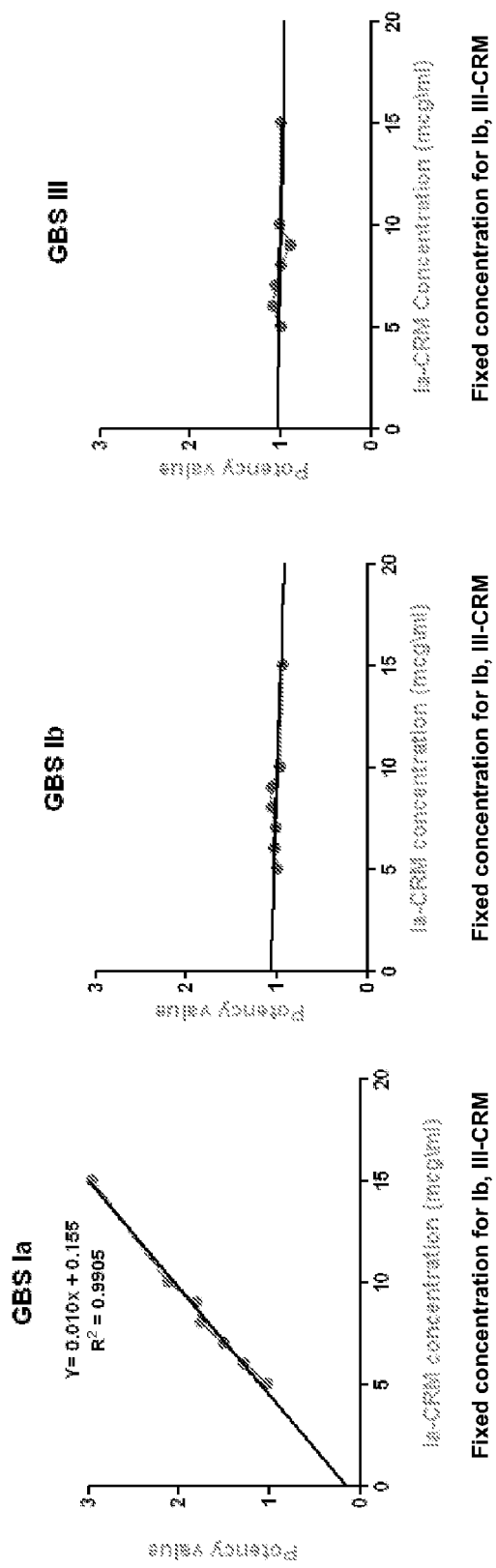
FIG. 21 shows the results of the assay for changing concentrations of GBS in a GBS trivalent vaccine.

Specificity and selectivity of the assay was assessed by measuring the spike recovery effect. The composition of the trivalent GBS vaccine was changed by adding increasing amounts of a single component: GBS Ia-$CRM_{197}$ conjugate. The results are shown in FIG. 21 and demonstrate the selectivity and specificity of the assay for a single GBS polysaccharide antigen (in this case GBS Ia polysaccharide).

It will be understood that the invention has been described by way of example only and modifications may be made whilst remaining within the scope and spirit of the invention.

REFERENCES

[1] Jameson, B A et al. 1988, *CABIOS* 4(1):181-186.
[2] Bushan et al. 1998 *Infect. Immun.* 66(12):5848-5853.
[3] Kasper et al. 1999 *Infect. Immun.* 67(8): 4303-4305.
[4] Wessels et al. (1990) *J Clin Invest* 86:1428-33.
[5] Wessels et al. (1989) *Infect Immun* 57:1089-94.
[6] WO2006/082527.
[7] WO 2009/081276.
[8] Ichiman and Yoshida (1981) *J. Appl. Bacteriol.* 51:229.

[9] U.S. Pat. No. 4,197,290
[10] Ichiman et al. (1991) *J. Appl. Bacteriol.* 71:176.
[11] WO2005/000346
[12] Anonymous (January 2002) *Research Disclosure*, 453077.
[13] Anderson (1983) *Infect Immun* 39(1):233-238.
[14] Anderson et al. (1985) *J Clin Invest* 76(1):52-59.
[15] EP-A-0372501.
[16] EP-A-0378881.
[17] EP-A-0427347.
[18] WO93/17712
[19] WO94/03208.
[20] WO98/58668.
[21] EP-A-0471177.
[22] WO91/01146
[23] Falugi et al. (2001) *Eur J Immunol* 31:3816-24.
[24] Baraldo et al. (2004) *Infect Immun* 72:4884-87.
[25] EP-A-0594610.
[26] WO00/56360.
[27] WO02/091998.
[28] Kuo et al. (1995) *Infect Immun* 63:2706-13.
[29] WO01/72337
[30] WO00/61761.
[31] WO00/33882
[32] WO2004/041157
[33] EP-A-0372501.
[34] EP-A-0378881.
[35] EP-A-0427347.
[36] WO93/17712
[37] WO94/03208.
[38] WO98/58668.
[39] EP-A-0471177.
[40] WO91/01146
[41] Falugi et al. (2001) *Eur J Immunol* 31:3816-3824.
[42] Baraldo et al. (2004) *Infect Immun* 72(8):4884-7.
[43] EP-A-0594610.
[44] Ruan et al. (1990) *J Immunol* 145:3379-3384.
[45] WO00/56360.
[46] Kuo et al. (1995) *Infect Immun* 63:2706-13.
[47] Michon et al. (1998) *Vaccine.* 16:1732-41.
[48] WO02/091998.
[49] WO01/72337
[50] WO00/61761.
[51] WO00/33882
[52] WO99/42130
[53] U.S. Pat. No. 4,761,283
[54] U.S. Pat. No. 4,356,170
[55] Lees et al. (1996) *Vaccine* 14:190-198.
[56] WO95/08348.
[57] WO98/42721
[58] U.S. Pat. No. 4,882,317
[59] U.S. Pat. No. 4,695,624
[60] EP-B-0 477 508
[61] *Mol. Immunol.*, 1985, 22, 907-919
[62] EP-A-0208375
[63] Bethell G. S. et al., *J. Biol. Chem.*, 1979, 254, 2572-4
[64] Hearn M. T. W., *J. Chromatogr.*, 1981, 218, 509-18
[65] WO00/10599
[66] Gever et al., Med. Microbiol. Immunol, 165: 171-288 (1979).
[67] U.S. Pat. No. 4,057,685.
[68] U.S. Pat. Nos. 4,673,574; 4,761,283; 4,808,700.
[69] U.S. Pat. No. 4,459,286.
[70] U.S. Pat. No. 5,204,098
[71] U.S. Pat. No. 4,965,338
[72] U.S. Pat. No. 4,663,160.
[73] WO2007/000343.
[74] WO96/40242
[75] Paoletti et al. (1990) J Biol Chem 265:18278-83
[76] Wessels et al. (1990) J Clin Invest 86:1428-33.
[77] Paoletti et al. (1992) Infect Immun 60:4009-14.
[78] Paoletti et al. (1992) J Clin Invest 89:203-9.
[79] Wessels et al. (1987) Proc Natl Acad Sci USA 84:9170-4.
[80] Wang et al. (2003) Vaccine 21:1112-7.
[81] Wessels et al. (1993) Infect Immun 61:4760-6
[82] Wessels et al. (1995) J Infect Dis 171:879-84.
[83] Baker et al. (2004) J Infect Dis 189:1103-12.
[84] U.S. Pat. No. 4,356,170.
[85] Paoletti & Kasper (2003) *Expert Opin Biol Ther* 3:975-984.
[86] Guttormsen et al. (2008) Proc Natl Acad Sci USA. 105(15):5903-5908. Epub 2008 March 31.
[87] WO2006/082530.
[88] WO96/40795
[89] Michon et al. (2006) Clin Vaccine Immunol 2006 August; 13(8)936-43.
[90] U.S. Pat. No. 6,818,418
[91] Bird et al., 1988 *Science* 242: 423-426
[92] Huston et al., 1988 *Proc. Natl. Acad. Sci. USA* 85:5879-5883
[93] EP-184,187
[94] GB 2188638
[95] EP-239400
[96] EP 0120694
[97] EP 0125023
[98] Sambrook & Russell, *Molecular Cloning: A Laboratory Manual:* $3^{rd}$ *Edition*, Cold Spring Harbor Laboratory Press
[99] Morrison, 1985 *Science,* 229:1202
[100] Breitling et al., Recombinant antibodies, John Wiley & Sons, Inc. and Spektrum Akademischer Verlag, 1999
[101] Lin, F. C The Journal of Infectious Diseases 2001; 184:1022-8
[102] Lin, F. C. et al The Journal of Infectious Diseases 2004; 190:928-34
[103] PCT/IB2011/054069
[104] Gennaro (2000) *Remington: The Science and Practice of Pharmacy.* 20th edition, ISBN: 0683306472.
[105] *Methods In Enzymology* (S. Colowick and N. Kaplan, eds., Academic Press, Inc.)
[106] *Handbook of Experimental Immunology*, Vols. I-IV (D. M. Weir and C. C. Blackwell, eds, 1986, Blackwell Scientific Publications)
[107] Sambrook et al. (2001) *Molecular Cloning: A Laboratory Manual,* 3rd edition (Cold Spring Harbor Laboratory Press).
[108] *Handbook of Surface and Colloidal Chemistry* (Birdi, K. S. ed., CRC Press, 1997)
[109] Ausubel et al. (eds) (2002) *Short protocols in molecular biology,* 5th edition (Current Protocols).
[110] *Molecular Biology Techniques: An Intensive Laboratory Course*, (Ream et al., eds., 1998, Academic Press)
[111] *PCR (Introduction to Biotechniques Series),* 2nd ed. (Newton & Graham eds., 1997, Springer Verlag)
[112] Geysen et al. (1984) *PNAS USA* 81:3998-4002.
[113] Carter (1994) *Methods Mol Biol* 36:207-23.
[114] Jameson, B A et al. 1988, *CABIOS* 4(1):181-186.
[115] Raddrizzani & Hammer (2000) *Brief Bioinform* 1(2): 179-89.
[116] Bublil et al. (2007) *Proteins* 68(1):294-304.
[117] De Lalla et al. (1999) *J. Immunol.* 163:1725-29.
[118] Kwok et al. (2001) *Trends Immunol* 22:583-88.
[119] Brusic et al. (1998) *Bioinformatics* 14(2):121-30

[120] Meister et al. (1995) *Vaccine* 13(6):581-91.
[121] Roberts et al. (1996) *AIDS Res Hum Retroviruses* 12(7):593-610.
[122] Maksyutov & Zagrebelnaya (1993) *Comput Appl Biosci* 9(3):291-7.
[123] Feller & de la Cruz (1991) *Nature* 349(6311):720-1.
[124] Hopp (1993) *Peptide Research* 6:183-190.
[125] Welling et al. (1985) *FEBS Lett.* 188:215-218.
[126] Davenport et al. (1995) *Immunogenetics* 42:392-297.
[127] Tsurui & Takahashi (2007) *J Pharmacol Sci.* 105(4): 299-316.
[128] Tong et al. (2007) *Brief Bioinform.* 8(2):96-108.
[129] Schirle et al. (2001) *J Immunol Methods.* 257(1-2):1-16.
[130] Chen et al. (2007) *Amino Acids* 33(3):423-8.
[131] *Current Protocols in Molecular Biology* (F. M. Ausubel et al., eds., 1987) Supplement 30
[132] Smith & Waterman (1981) *Adv. Appl. Math.* 2: 482-489.
[133] Abhinandan, K. R. and Martin, A. C. R. (2008) *Molecular Immunology*, 45, 3832-3839.

---

The invention claimed is:

1. A method for detecting in a sample the presence of an antibody against a first conjugate, wherein the first conjugate comprises an antigen associated with a first carrier by a first covalent association, the method comprising the steps:
   (a) contacting a second conjugate, wherein the second conjugate comprises the antigen associated with a second carrier by a second covalent association, with the sample under conditions that allow binding of the antibody to the antigen; and
   (b) contacting the antigen with an agent to detect the antibody bound to the antigen;
   wherein the first covalent association is different from the second covalent association, and wherein the second covalent association comprises a linker.

2. The method of claim 1, further comprising measuring the concentration of the antibody in the sample.

3. The method of claim 1, wherein the sample is selected from the group consisting of whole blood, serum, and plasma.

4. The method of claim 3, wherein the method further comprises a step
   (c) comprising comparing the concentration with a standard criterion for seroprotection for the antigen.

5. The method of claim 1, wherein the antibody is an immunoglobulin G antibody.

6. The method of claim 1, wherein the first carrier comprises a protein carrier.

7. The method of claim 6, wherein the protein carrier comprises a protein selected from the group consisting of diphtheria toxoid, tetanus toxoid, CRM197, and protein D.

8. The method of claim 1, wherein the second carrier comprises a protein carrier.

9. The method of claim 8, wherein the protein carrier comprises serum albumin.

10. The method of claim 1, wherein the antigen comprises a saccharide.

11. The method of claim 10, wherein the saccharide comprises a group B streptococcus capsular saccharide.

12. The method of claim 1, wherein the second conjugate is immobilized on a surface.

13. A method of claim 1, wherein the agent to detect the presence of the antibody comprises a detectably labelled antibody against the antibody.

14. The method of claim 1, wherein the first covalent association comprises the linker —NHCH$_2$—.

15. The method of claim 1, wherein the second covalent association comprises the linker —C(O)NHNHC(O)L$^1$C(O)NHNHC(O)—, wherein L$^1$ is a divalent radical selected from the group consisting of alkylene, alkenylene, cycloalkylene, cycloalkenylene, arylene, heteroarylene, arylalkylene, alkarylene, and alkylenearylalkylene.

16. A method for detecting in a sample the presence of an antibody against a first conjugate, wherein the first conjugate comprises an antigen associated with a first carrier by a first covalent association, the method comprising the steps:
(a) contacting a second conjugate, wherein the second conjugate comprises the antigen associated with a second carrier by a second covalent association, with the sample under conditions that allow binding of the antibody to the antigen; and
(b) contacting the antigen with an agent to detect the antibody bound to the antigen,
wherein:
(i) the antigen comprises a group B streptococcus capsular saccharide,
(ii) the first carrier comprises CRM 197,
(iii) the first covalent association comprises a linker, wherein the linker is —NHCH$_2$—,
(iv) the second carrier comprises a serum albumin, and
(v) the second covalent association comprises a linker, wherein the linker is —C(O)NHNHC(O)(CH$_2$)$_4$C(O)NHNHC(O)—.

17. A method of evaluating the potency of a conjugate vaccine, comprising:
(a) contacting a first sample with an antibody to form a first mixture, wherein the first sample comprises a reference conjugate vaccine, wherein the reference conjugate vaccine comprises an antigen conjugated to a first carrier and wherein the antibody binds to the antigen;
(b) contacting a second sample with the antibody to form a second mixture, wherein the second sample comprises a test conjugate vaccine, wherein the test conjugate vaccine comprises the antigen conjugated to a second carrier;
c) contacting a portion of the first mixture with a first conjugate to form a first test sample, wherein the first conjugate comprises the antigen associated with a third carrier by a covalent association which comprises a linker;
(d) contacting a portion of the second mixture with the first conjugate to form a second test sample; and
(e) contacting the first test sample and the second test sample with an agent to detect the antibody bound to the antigen,
wherein the antibody comprises at least one region selected from the group consisting of:
(a) at least one variable region comprising an amino acid sequence with at least 95% sequence identity to a variable region within SEQ ID NO:2 or a variable region within SEQ ID NO:4;
(b) a heavy chain third CDR (HC-CDR3) comprising the amino acid sequence of SEQ ID NO:24;
(c) at least one variable region comprising an amino acid sequence with at least 95% sequence identity to a variable region within SEQ ID NO:6 or a variable region within SEQ ID NO:8;
(d) a heavy chain third CDR (HC-CDR3) comprising the amino acid sequence of SEQ ID NO:30;
(e) at least one variable region comprising an amino acid sequence with at least 95% sequence identity to a variable region within SEQ ID NO:10 or a variable region within SEQ ID NO:12; and
(f) a heavy chain third CDR (HC-CDR3) comprising the amino acid sequence of SEQ ID NO:36.

18. The method of claim 17, wherein the antibody comprises a pair of light chain third CDR (LC-CDR3) and HC-CDR3 selected from the group consisting of:
(a) a light chain third CDR (LC-CDR3) comprising an amino acid sequence of SEQ ID NO:33 and a heavy chain third CDR (HC-CDR3) comprising the amino acid sequence of SEQ ID NO:24;
(b) a light chain third CDR (LC-CDR3) comprising the amino acid sequence of SEQ ID NO:27 and a heavy chain third CDR (HC-CDR3) comprising the amino acid sequence of SEQ ID NO:30;and
(c) a light chain third CDR (LC-CDR3) comprising the amino acid sequence of SEQ ID NO:21 and a heavy chain third CDR (HC-CDR3) comprising the amino acid sequence of SEQ ID NO:36.

* * * * *